(12) United States Patent  
Chen

(10) Patent No.: US 10,519,145 B2
(45) Date of Patent: Dec. 31, 2019

(54) PYRAZOLE-OXAZOLIDINONE COMPOUND FOR ANTI-HEPATITIS B VIRUS

(71) Applicant: Shanghai Zhimeng Biopharma Co., Ltd., Shanghai (CN)

(72) Inventor: Huanming Chen, Shanghai (CN)

(73) Assignee: Shanghai Zhimeng Biopharma Co., Ltd., Shanghai (CN)

( * ) Notice: Subject to any disclaimer, the term of this patent is extended or adjusted under 35 U.S.C. 154(b) by 0 days.

(21) Appl. No.: 16/091,320

(22) PCT Filed: Apr. 6, 2017

(86) PCT No.: PCT/CN2017/079552
§ 371 (c)(1),
(2) Date: Oct. 4, 2018

(87) PCT Pub. No.: WO2017/173999
PCT Pub. Date: Oct. 12, 2017

(65) Prior Publication Data
US 2019/0152963 A1    May 23, 2019

(30) Foreign Application Priority Data
Apr. 6, 2016 (CN) .......................... 2016 1 0210422

(51) Int. Cl.
| | |
|---|---|
| *C07D 413/14* | (2006.01) |
| *C07D 417/14* | (2006.01) |
| *C07D 403/04* | (2006.01) |
| *A61K 31/428* | (2006.01) |
| *C07D 413/04* | (2006.01) |
| *A61P 31/20* | (2006.01) |

(52) U.S. Cl.
CPC .......... *C07D 413/14* (2013.01); *A61K 31/428* (2013.01); *A61P 31/20* (2018.01); *C07D 403/04* (2013.01); *C07D 413/04* (2013.01); *C07D 417/14* (2013.01)

(58) Field of Classification Search
None
See application file for complete search history.

(56) References Cited

FOREIGN PATENT DOCUMENTS

| | | |
|---|---|---|
| WO | 2006/033995 A2 | 3/2006 |
| WO | 2007/014023 A1 | 2/2007 |

OTHER PUBLICATIONS

Patani et al. (Chemical Reviews, 1996, vol. 96, 3147-3176).*
Int'l Search Report dated Jul. 10, 2017 in Int'l Application No. PCT/CN2017/079552.

* cited by examiner

*Primary Examiner* — Kamal A Saeed
(74) *Attorney, Agent, or Firm* — Panitch Schwarze Belisario & Nadel LLP

(57) ABSTRACT

The present invention discloses a pyrazole-oxazolidinone compound having anti-hepatitis B virus activity, which has the structure of formula (I), wherein each variable is as defined herein.

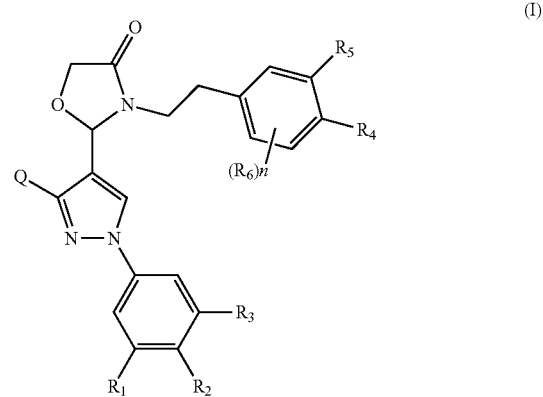

20 Claims, No Drawings

PYRAZOLE-OXAZOLIDINONE COMPOUND FOR ANTI-HEPATITIS B VIRUS

TECHNICAL FIELD

The present invention relates to a class of pyrazole-oxazolidinone compounds having anti-hepatitis B virus activity.

BACKGROUND

Virus hepatitis B is a disease that is caused by hepatitis B virus (HBV), mainly characterized with inflammatory lesions of the liver, and can cause multiple-organ damage. Hepatitis B is widely prevalent throughout the world, mainly affecting children and young adults, and a small number of which may be transformed into liver cirrhosis or liver cancer. Therefore, it has become a worldwide disease that seriously threatens human health. It is also one of the most widespread and most harmful diseases. Virus hepatitis B does not have a certain epidemic period. It can develop throughout the year, and most of it develops sporadically. In recent years, the incidence of hepatitis B has increased significantly. Studies have shown that inhibition of HBV is directly related to the therapeutic effect of hepatitis B (see, e.g., Klaus Klumpp and Thibaut Crepin, Capsid proteins of enveloped viruses as antiviral drug targets, *Current Opinion in Virology*, 2014, 5: 63-71; Timothy M. Block, Siddhartha Rawat, Carol L. Brosgart, Chronic hepatitis B: A wave of new therapies on the horizon, *Antiviral Research*, 121, 2015, 69-81).

Although there are many methods for the treatment of hepatitis B virus infection, they are greatly limited. Only in very few patients, the continuous serum HBV DNA reduction, serological conversion of e antigen and s antigen and other treatment effects can be observed.

For example, interferon alpha has been widely used for the treatment of chronic HBV infection for many years, but interferon is only effective for specific types of patients and is poorly tolerated. Similarly, lamivudine (3'-thio-2',3'-dideoxycytidine) has been used for the treatment of HBV infection because of its marked inhibitory effect on HBV replication, but due to the gradually increased resistance rates, the efficacy in a large proportion of patients is limited. Recently marketed adefovir dipivoxil (9-[2-[[bis[(pivaloyloxy)methyl]phosphinyl]methoxy]ethyl]adenine) is effective to the lamivudine-resistant patients, but the drug has the disadvantage that the sustained viral response rate is low (less than 20%) and the maximum tolerated dose and duration of treatment are often limited due to its nephrotoxicity.

Recent studies have found that a number of drugs have good anti-HBV activity and have entered clinical studies. For example, 2'-fluoro-5-methyl-β-L-uracil arabinoside (Bukwang), 2'-deoxy-5-fluoro-3'-thiocytidine (Gilead), 2'-deoxy-L-thymidine (Idenix), 2'-deoxy-L-cytidine (Idenix) and other nucleosides showed significant anti-HBV activity. In addition, cyclic nucleoside compounds such as 2-amino-1,9-dihydro-9[(1 S ,3 R,4S)-4-hydroxy-3-hydroxymethyl-2-methylenecyclopent yl]-6H-purine-6-one monohydrate (Bristol-Myers Squibb) and liver-targeting acyclic nucleoside compounds such as Ribapharm are also clinically active against HBV.

Although most of the recently discovered anti-HBV drugs exhibit good in vitro antiviral activity, low response rates and resistance limit the clinical effectiveness of these drugs. Therefore, although there are currently many drugs and methods for treating HBV, novel or improved drugs and methods of treatment are still clinically needed.

In summary, the existing therapeutic drugs for HBV have the limitations of limited therapeutic effect, easy drug resistance and high toxicity. Therefore, there is an urgent need for new drugs with high efficacy, low toxicity, and different drug resistance profiles clinically.

SUMMARY OF INVENTION

The object of the present invention is to provide a class of compounds having a function of inhibiting HBV replication.

Another object of the present invention is to provide a pharmaceutical use of the above compound.

One aspect of the invention relates to a compound of formula I or a pharmaceutically acceptable salt or enantiomer or tautomer thereof,

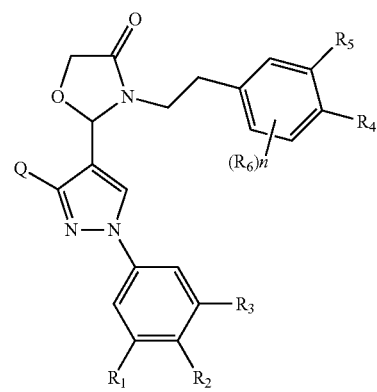

wherein, each of $R_1$, $R_2$ and $R_3$ is independently selected from hydrogen, halogen, optionally substituted alkyl, amino and hydroxyl;

one of $R_4$ and $R_5$ is amino and the other is selected from hydrogen, halogen, amino and hydroxyl; or $R_4$ and $R_5$, together with the carbon atom to which they are attached, form an optionally substituted five-membered heterocyclic or heteroaryl group containing at least one nitrogen atom, wherein —$CH_2$— in said heterocyclic group is optionally replaced by —C(=O)—, —C(=S)—, or —C(=NH)—;

$R_6$ is selected from deuterium, halogen, amino and hydroxyl;

n is 0, 1 or 2;

Q is aryl or heteroaryl optionally substituted with one or more halogens.

The chiral carbon in formula I may have R configuration or S configuration.

Another aspect of the invention relates to a compound of formula I, or a pharmaceutically acceptable salt or enantiomer or tautomer thereof, for use in the inhibition of hepatitis B virus.

Another aspect of the invention relates to a compound of formula I, or a pharmaceutically acceptable salt or enantiomer or tautomer thereof, for use in the treatment of hepatitis B virus infection in a mammal, particularly a human.

Another aspect of the invention relates to a pharmaceutical composition comprising a compound of formula I or a pharmaceutically acceptable salt or enantiomer or tautomer thereof, and a pharmaceutically acceptable carrier.

Another aspect of the invention relates to the use of a compound of formula I, or a pharmaceutically acceptable salt or enantiomer or tautomer thereof, in the manufacture of a medicament for inhibiting hepatitis B virus.

Another aspect of the invention relates to a method for inhibiting hepatitis B virus comprising administering to a subject in need thereof a therapeutically effective amount of a compound of formula I or a pharmaceutically acceptable salt or enantiomer or tautomer thereof.

DESCRIPTION OF INVENTION

One aspect of the invention relates to a compound having the following general formula I, or a pharmaceutically acceptable salt or enantiomer or tautomer thereof:

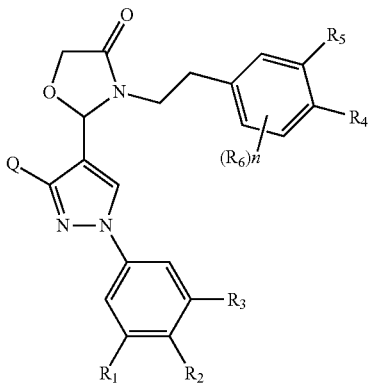

I wherein, each of $R_1$, $R_2$ and $R_3$ is independently selected from hydrogen, halogen, optionally substituted alkyl, amino and hydroxyl;

one of $R_4$ and $R_5$ is amino and the other is selected from hydrogen, halogen, amino and hydroxyl; or $R_4$ and $R_5$, together with the carbon atom to which they are attached, form an optionally substituted five-membered heterocyclic or heteroaryl group containing at least one nitrogen atom, wherein —$CH_2$- in said heterocyclic group is optionally replaced by —C(=O)—, —C(=S)—, or —C(=NH)—;

$R_6$ is selected from deuterium, halogen, amino and hydroxyl;

n is 0, 1 or 2;

Q is aryl or heteroaryl optionally substituted with one or more halogens.

The compounds of the present application may have tautomers. For example, the following two structural parts are considered as an equivalent structural part in this application.

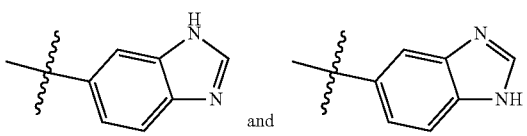 [SMILES: *c1ccc2nc[nH]c2c1 ; *c1ccc2[nH]cnc2c1]

Similarly, the following two structural parts are also considered as an equivalent structural part in this application.

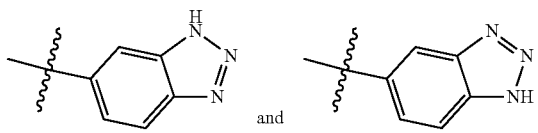 [SMILES: *c1ccc2nn[nH]c2c1 ; *c1ccc2[nH]nnc2c1]

The compounds of the present application may have one or more stereogenic centers, and each isomer may exist in R or S configuration or a combination thereof.

Thus, in one embodiment, the chiral carbon in formula I is in R configuration and the structure is shown in formula I-R:

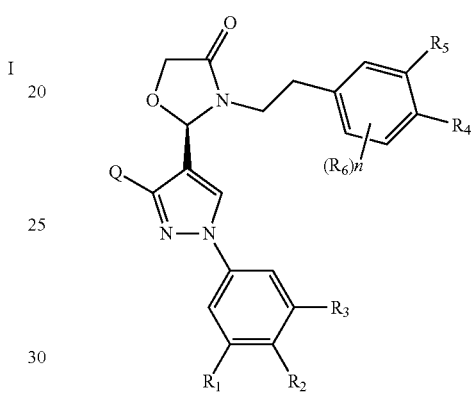

I-R

In the present application, the enantiomers and tautomers of a particular compound should be understood to include all possible isomers and mixtures thereof. Thus, the compounds of the present application include all configurationally different enantiomeric, diastereomeric, and tautomeric forms and their corresponding mixtures.

In one embodiment, in formula I and formula I-R:

each of $R_1$, $R_2$ and $R_3$ is independently hydrogen or halogen; preferably, $R_1$ and $R_3$ are both hydrogen and $R_2$ is halogen; more preferably, $R_1$ and $R_3$ are both hydrogen and $R_2$ is bromine;

$R_4$ and $R_5$, together with the carbon atom to which they are attached, form an optionally substituted five-membered heterocyclic or heteroaryl group containing at least one nitrogen atom, wherein —$CH_2$— in said heterocycle group is optionally replaced by —C (=O)—, —C(=S)—, or —C(=NH)—, preferably optionally replaced by —C(=O)— or —C(=S)—; and when the heterocyclic or heteroaryl group is optionally substituted, the substituent is selected from halogen and alkoxycarbonylamino;

$R_6$ is deuterium or halogen;

Q is aryl or heteroaryl optionally substituted with one or more halogens, especially fluorine, said aryl is phenyl, and said heteroaryl is selected from furyl, pyrrolyl and thienyl.

In one embodiment, $R_6$ in formula I and formula I-R is fluorine.

In one embodiment, Q in formula I and formula I-R is p-fluorophenyl.

In another embodiment, Q in formula I and formula I-R is thienyl or furyl, preferably furan-2-yl.

In one embodiment, the moieties in formula I and formula I-R:

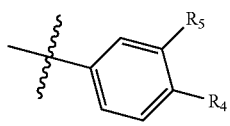
Selected from:
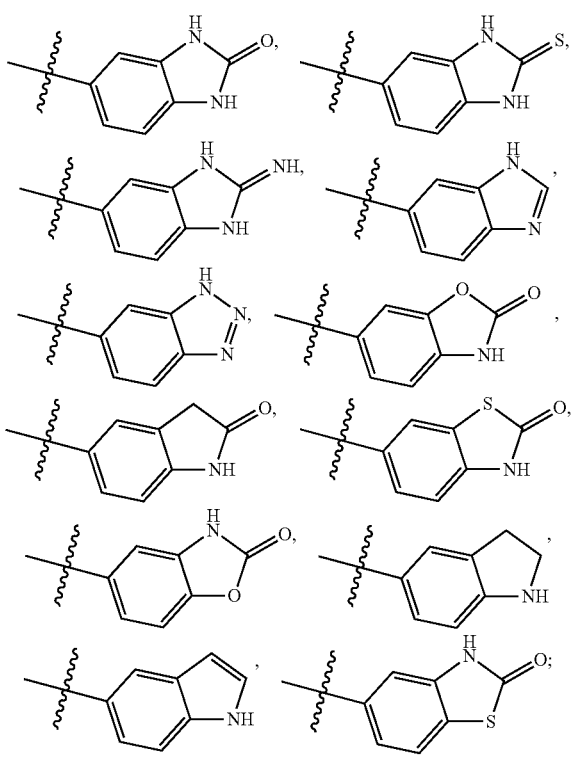
Preferably:
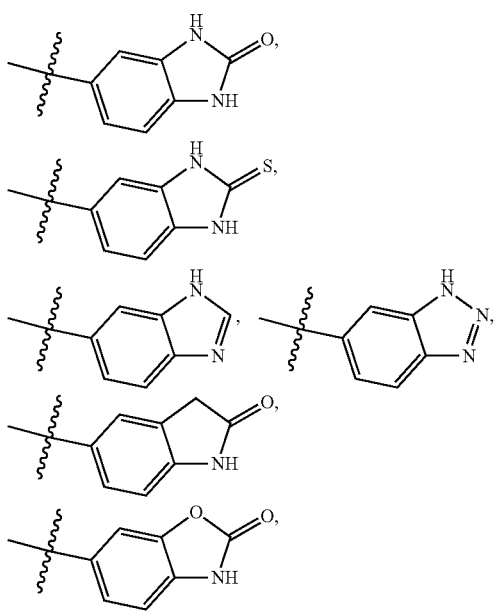
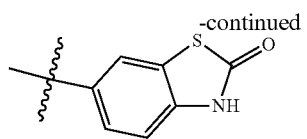
More preferably:
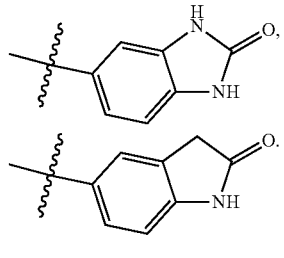
In one embodiment, the compound of formula I is selected from:
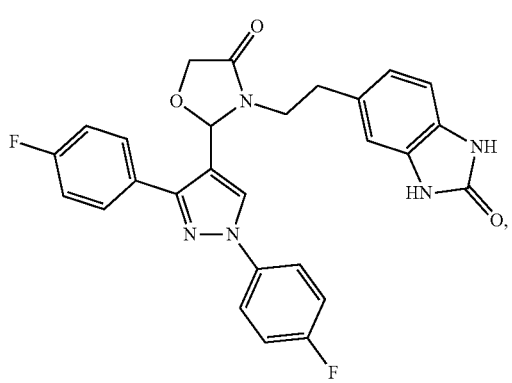
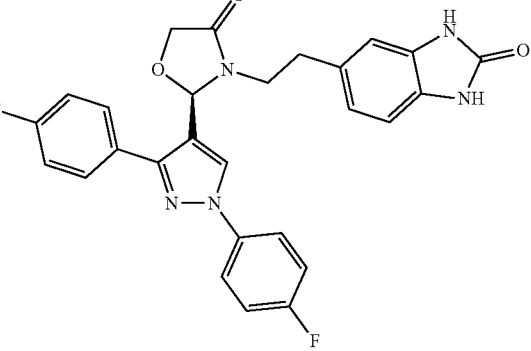
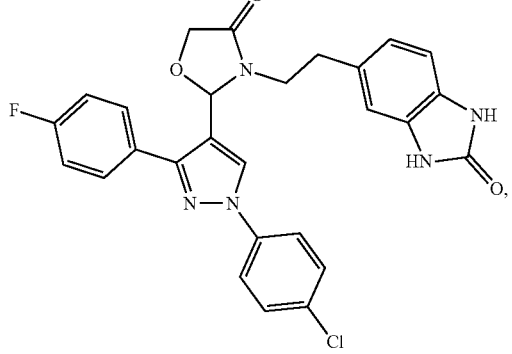

-continued
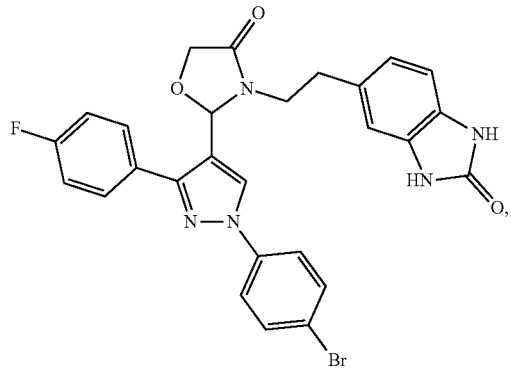
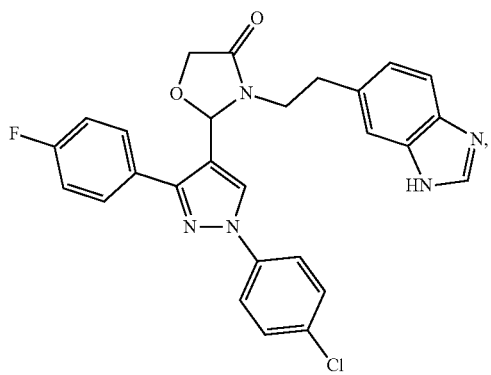
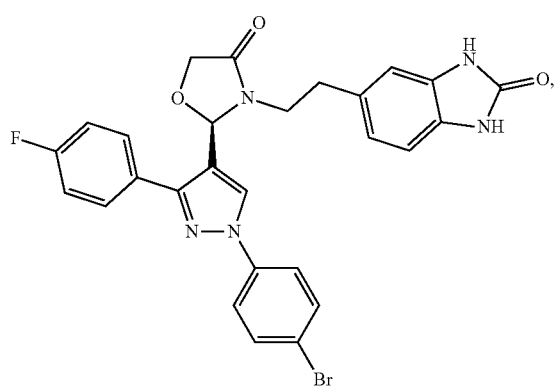
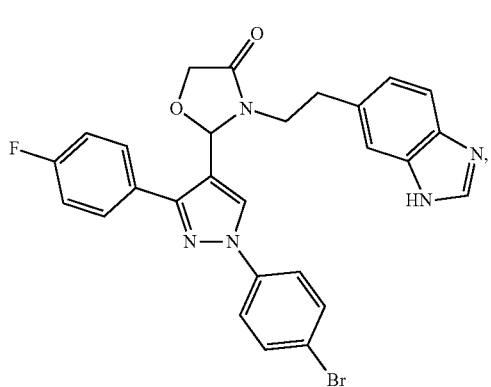
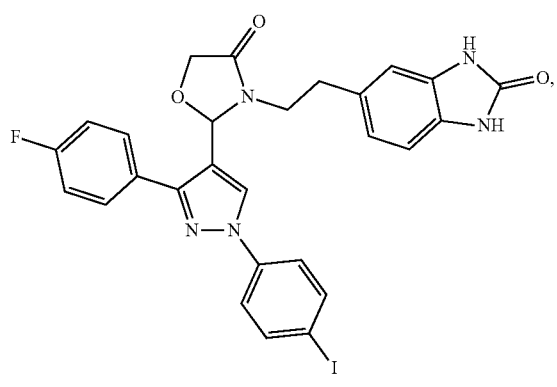
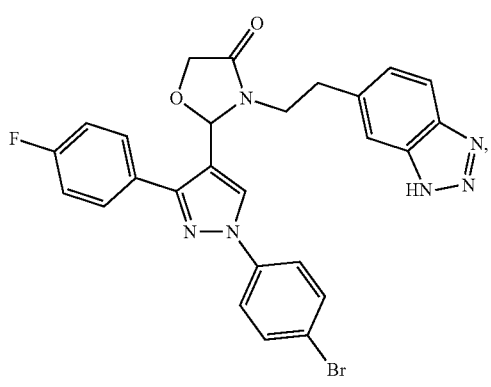
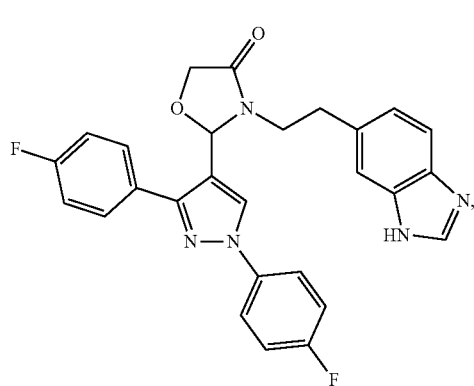
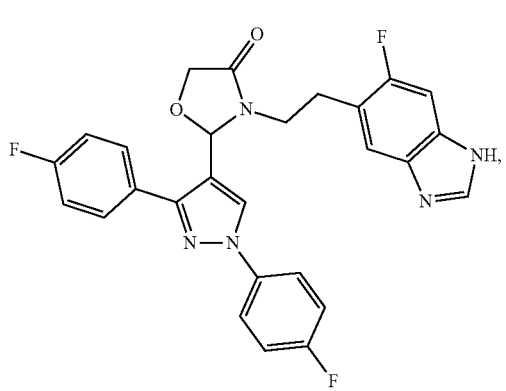

9
-continued
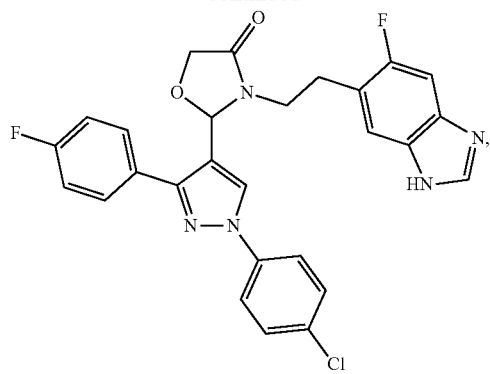
10
-continued
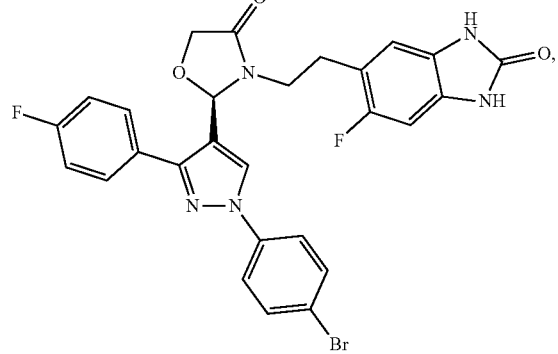
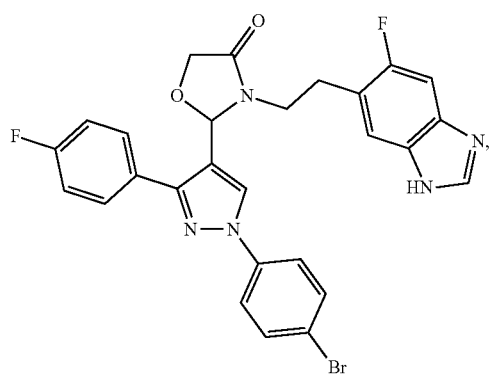
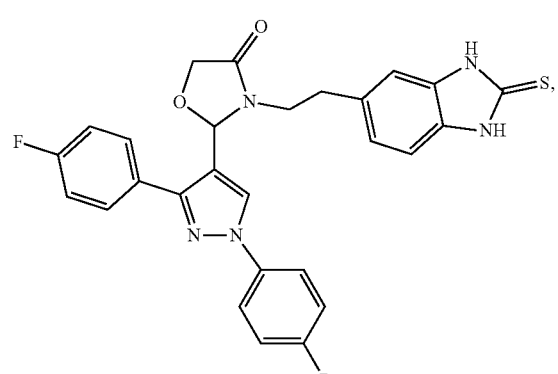
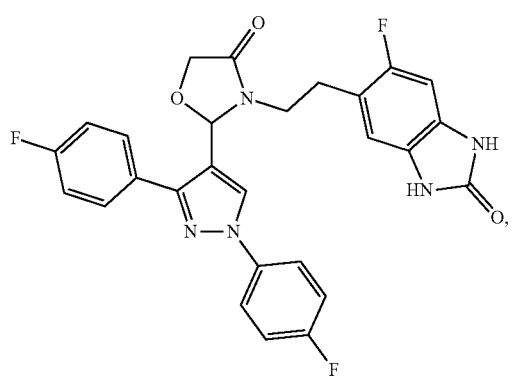
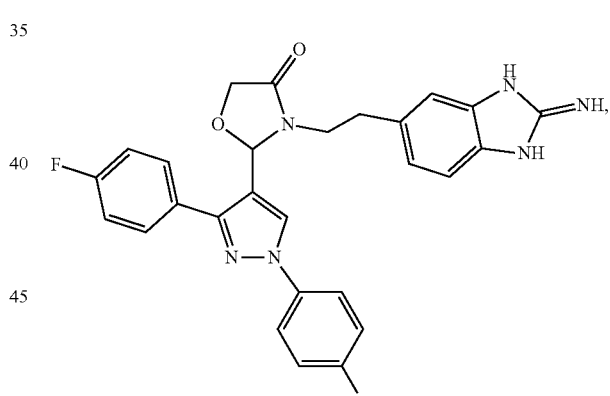
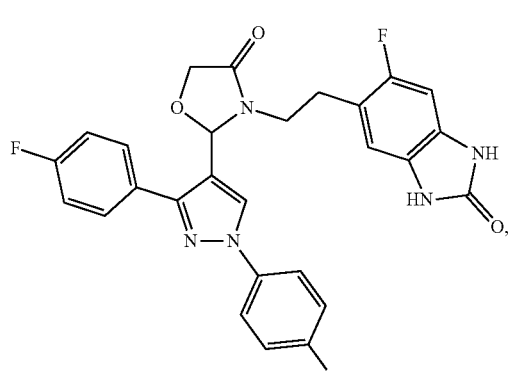
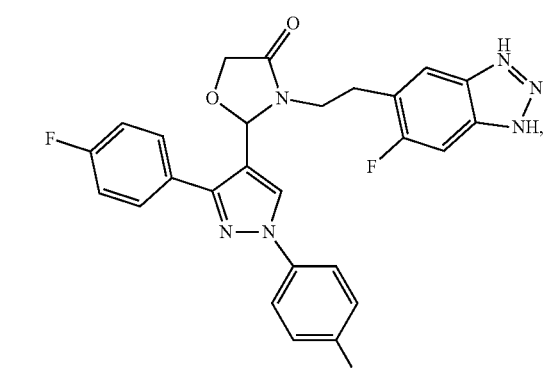

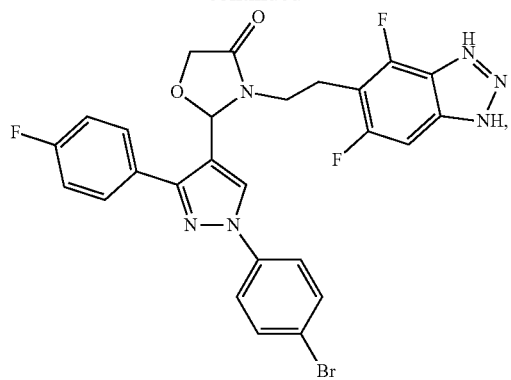
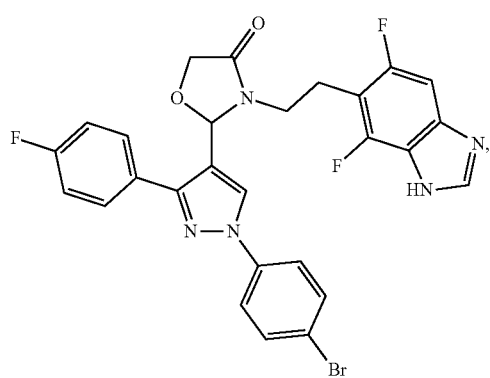
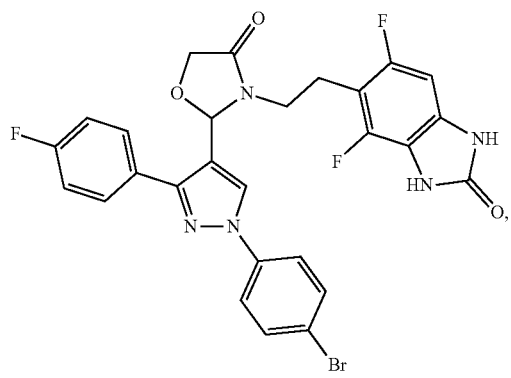
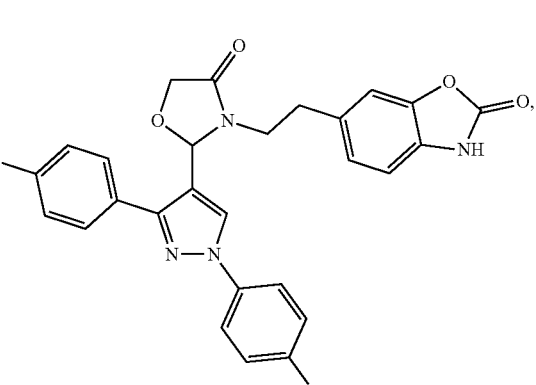
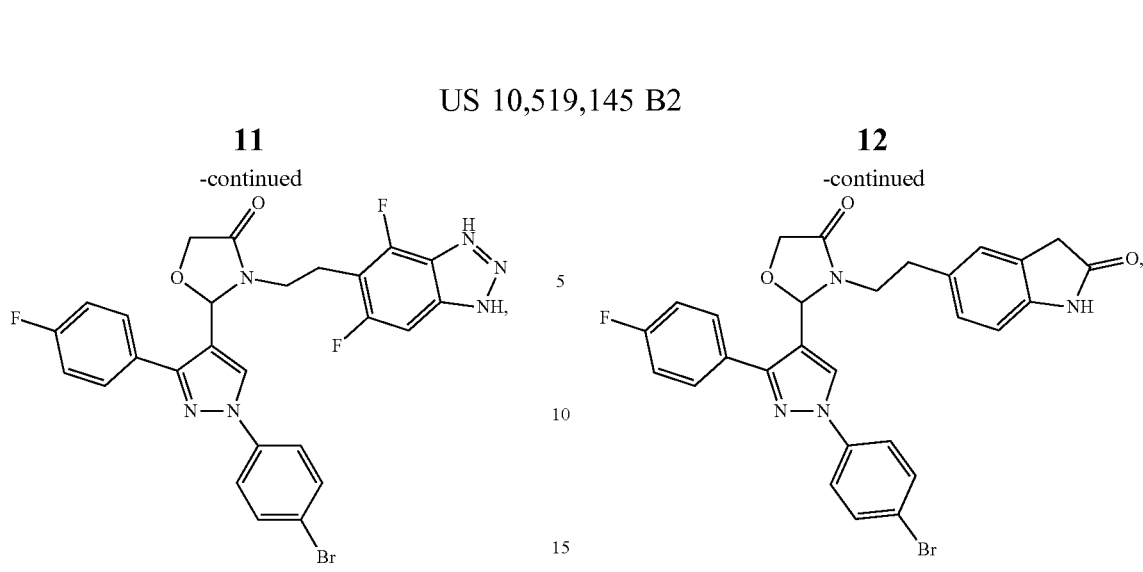
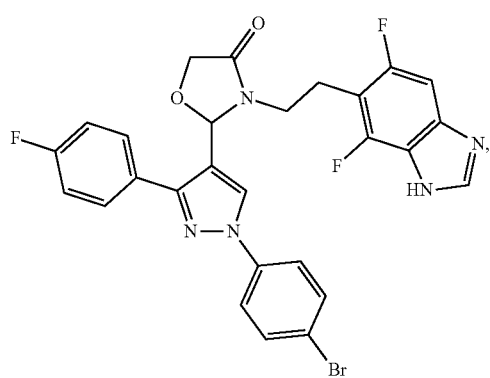
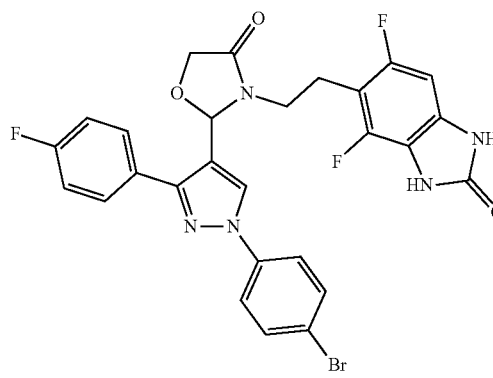
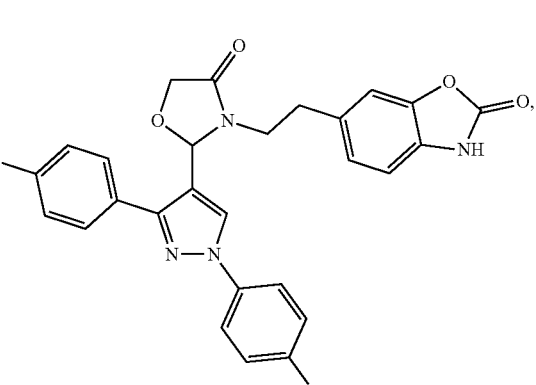

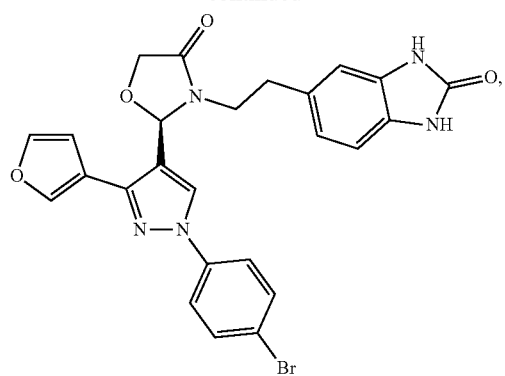
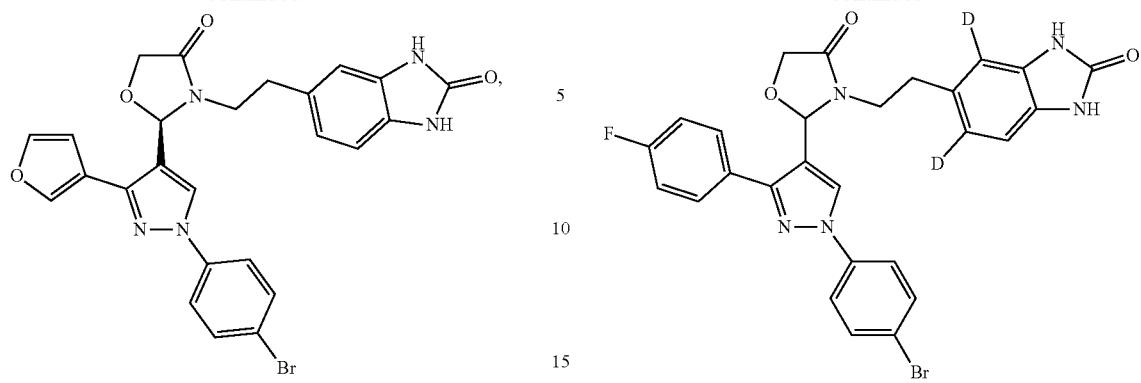
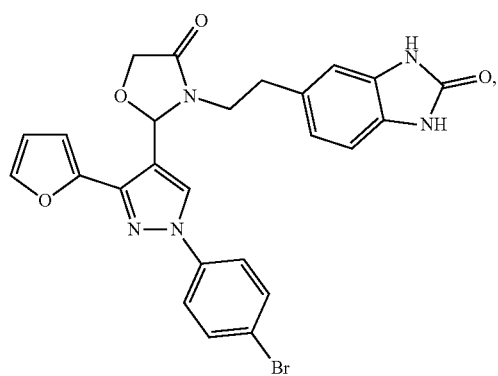
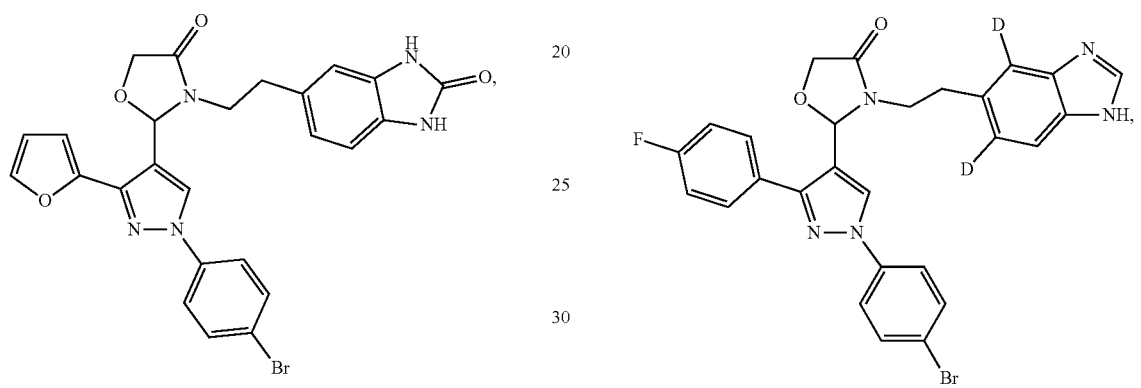
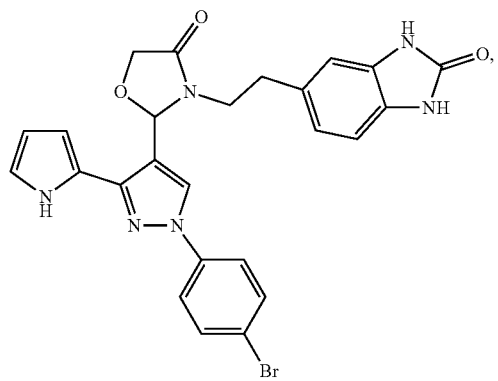
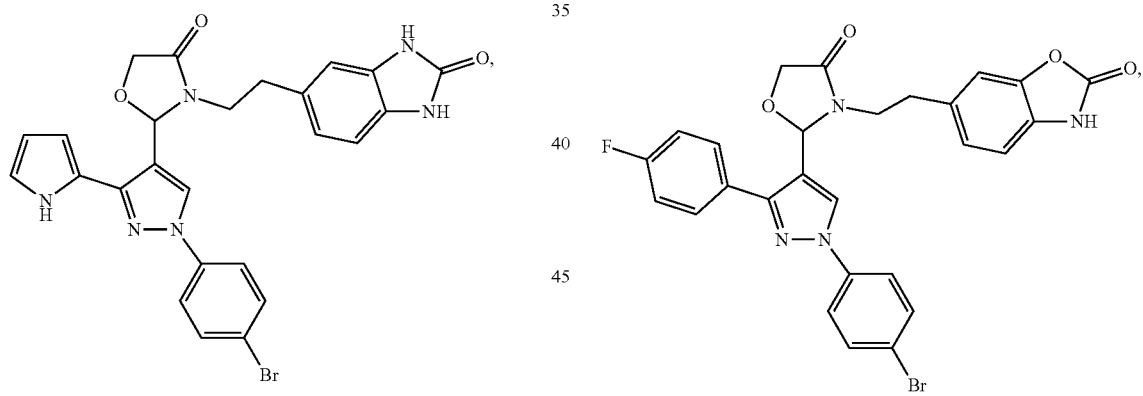
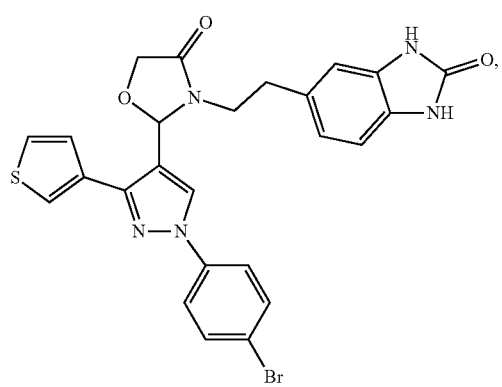
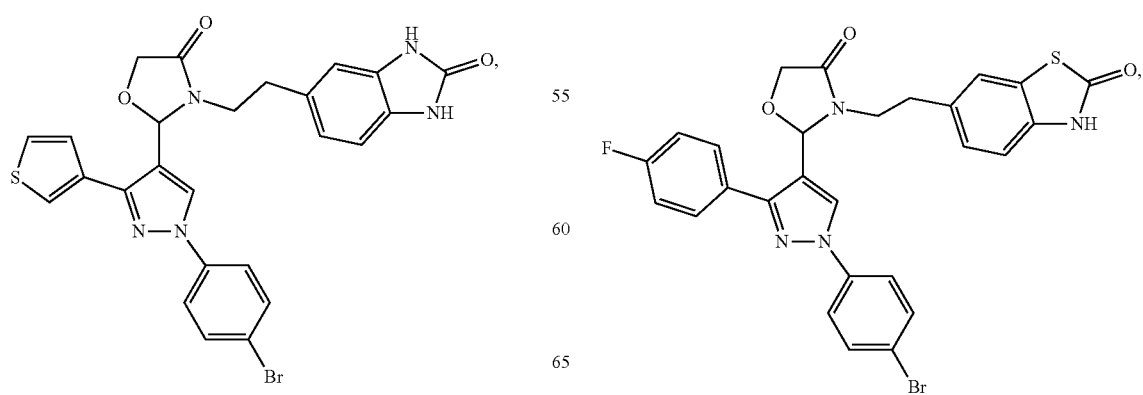

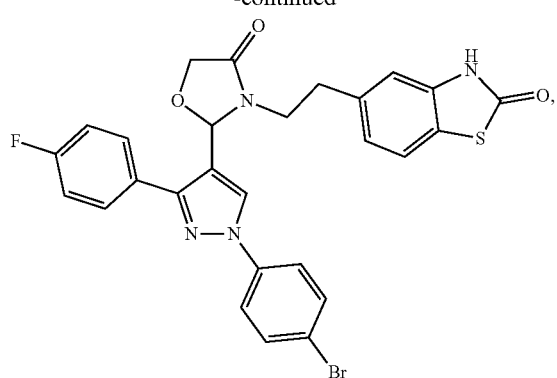
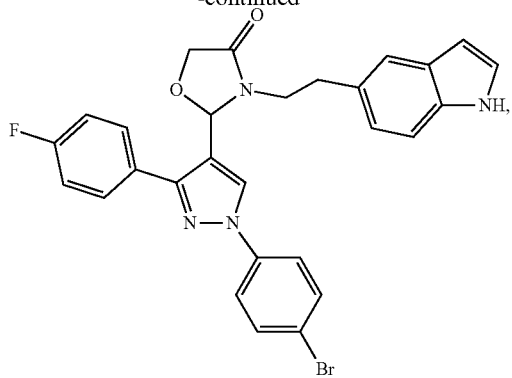
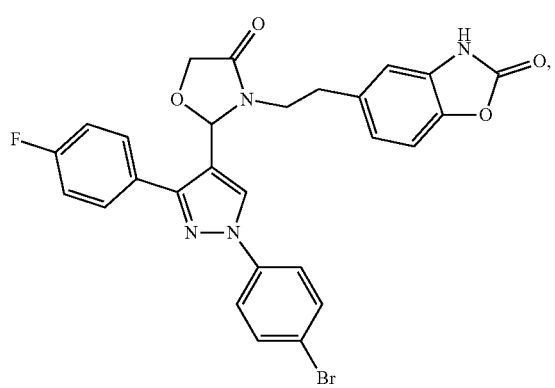
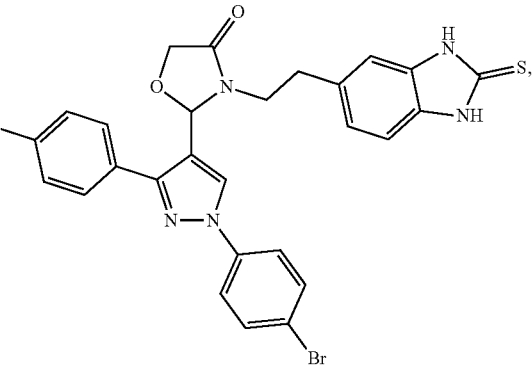
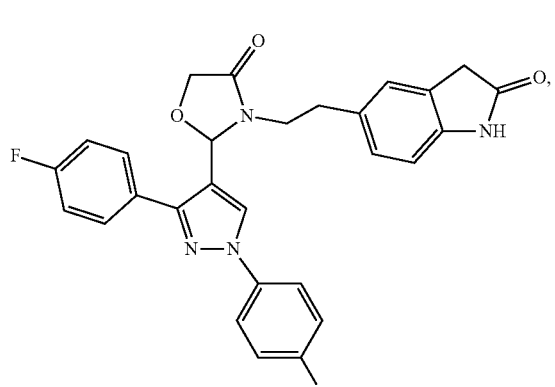
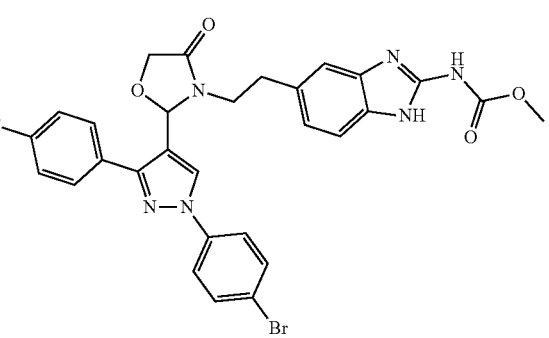
In a preferred embodiment, the compound of formula I is selected from:
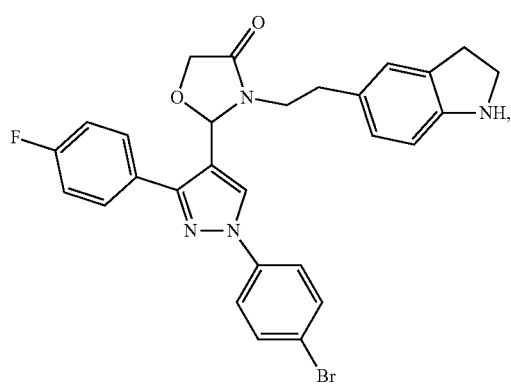
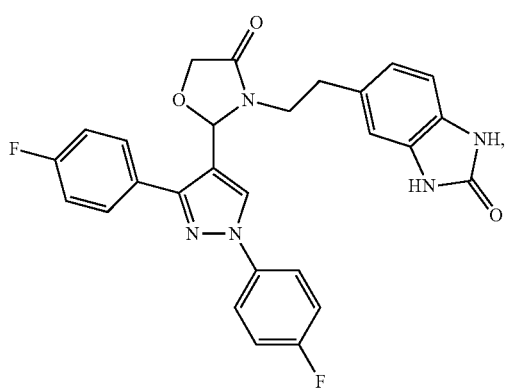

-continued
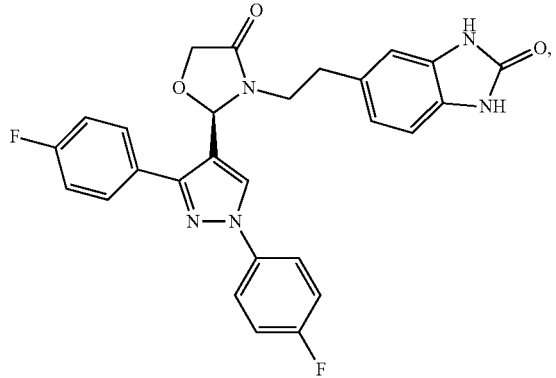
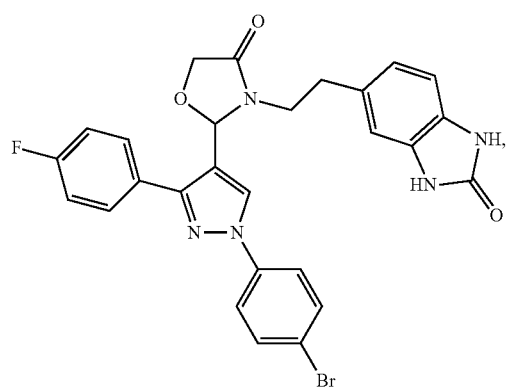
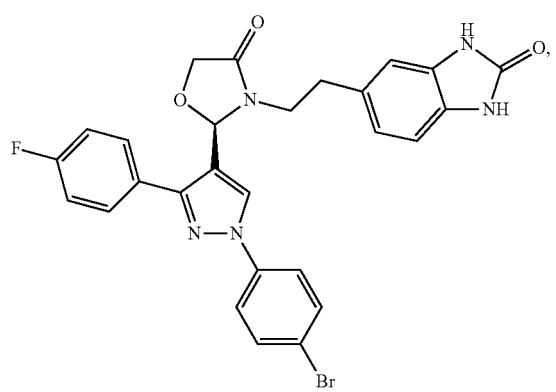
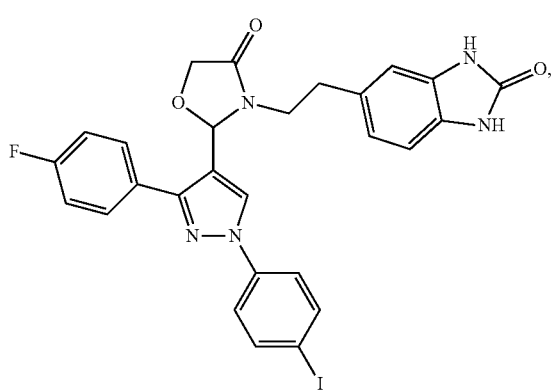
-continued
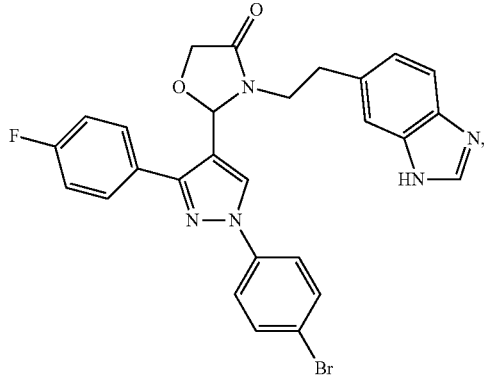
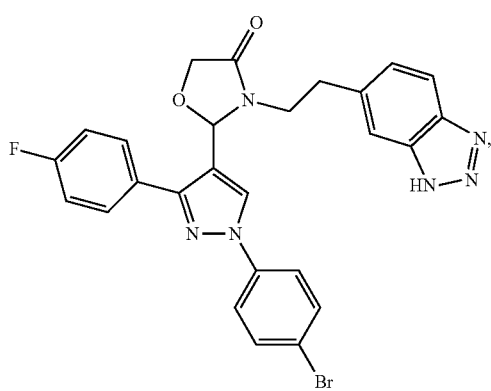
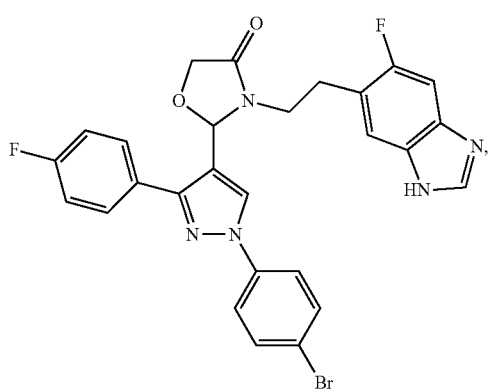
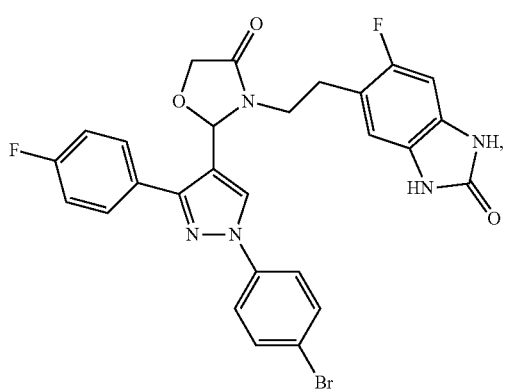

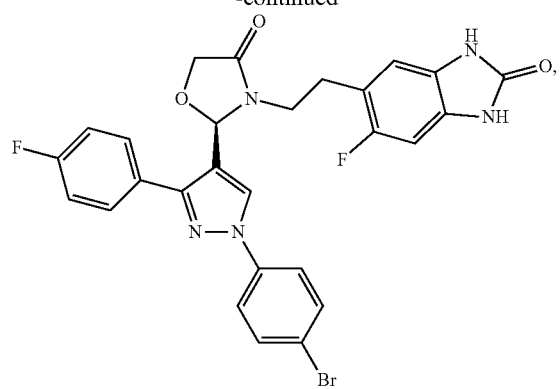
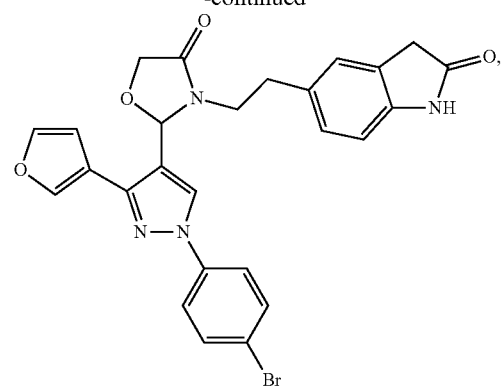
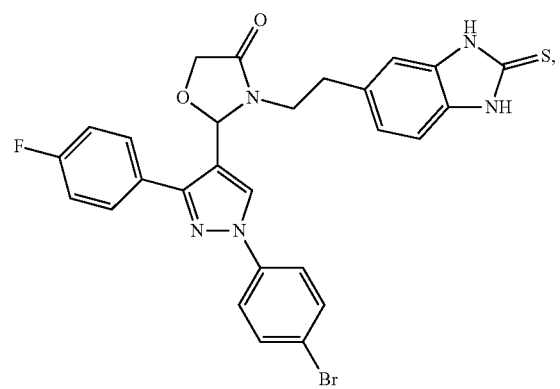
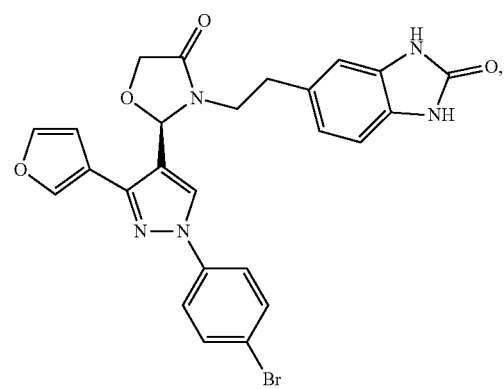
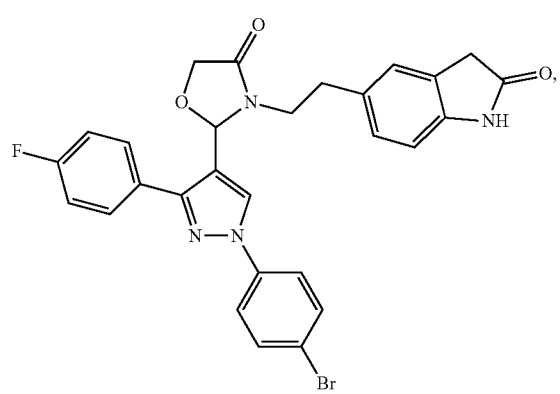
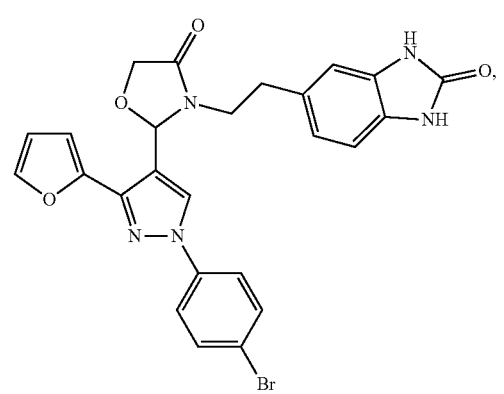
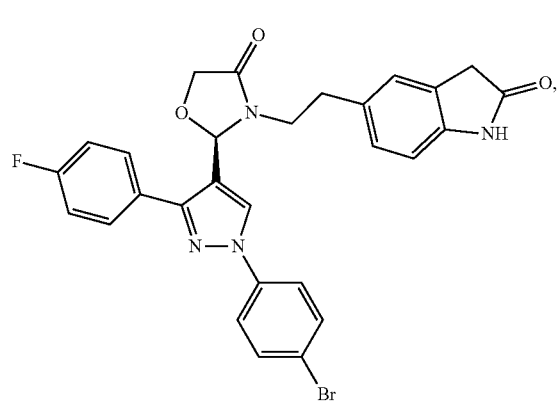
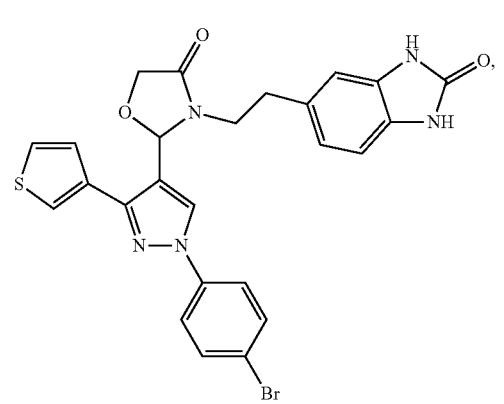

-continued

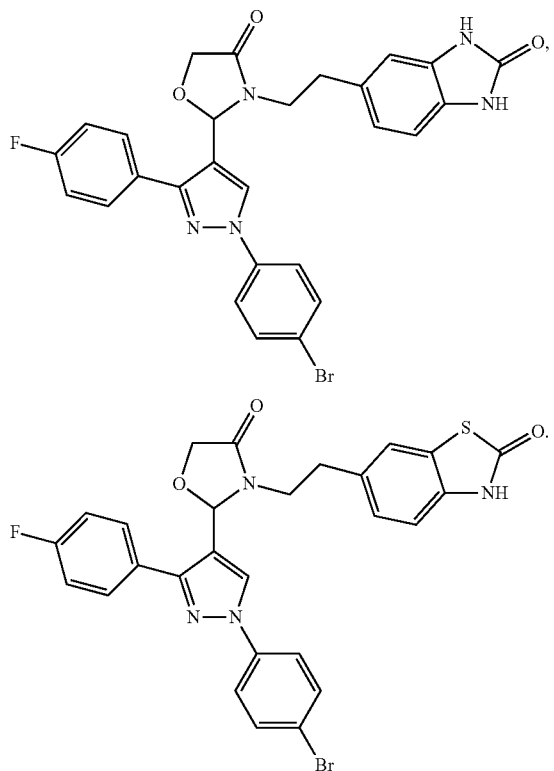

In a more preferred embodiment, the compound of formula I is selected from:

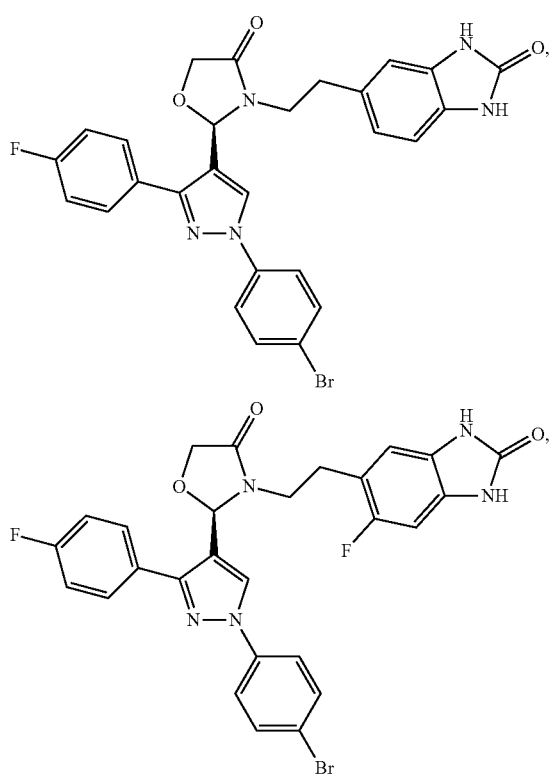

-continued

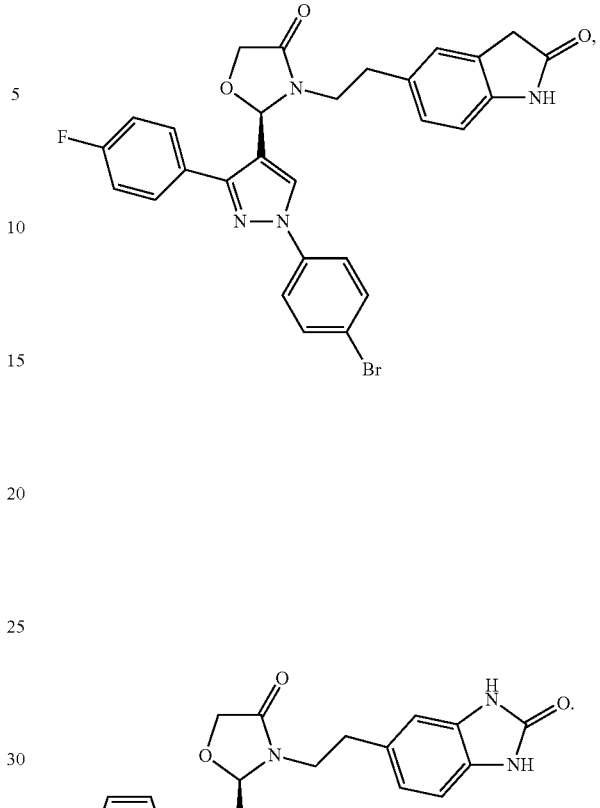

In one embodiment, in formula I and formula I-R:

each of $R_1$, $R_2$, and $R_3$ is independently selected from hydrogen, $C_1$-$C_3$ alkyl, halogen;

one of $R_4$ and $R_5$ is amino, and the other is selected from hydrogen, halogen, especially fluorine, and amino;

$R_6$ is halogen, especially fluorine;

Q is aryl or heteroaryl optionally substituted with one or more halogens, especially fluorine, the aryl group is phenyl, and the heteroaryl is selected from furyl, pyrrolyl, thienyl and pyridyl.

In one embodiment, in formula I and formula I-R, the alkyl group as $R_1$, $R_2$, or $R_3$ is methyl.

In one embodiment, in formula I and formula I-R, the halogen as $R_4$ or $R_5$ is fluorine.

In one embodiment, in formula I and formula I-R, the halogen as $R_6$ is fluorine.

In one embodiment, Q in formula I and formula I-R is p-fluorophenyl.

In one embodiment, $R_4$ in formula I and formula I-R is amino, $R_5$ is hydrogen, and n is 0.

In one embodiment, the compound of formula I is selected from:

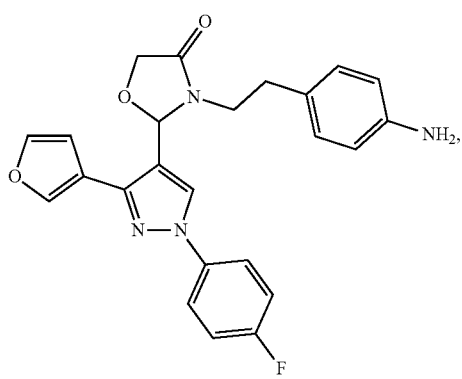
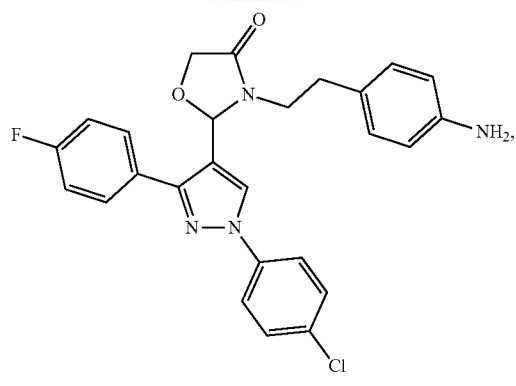
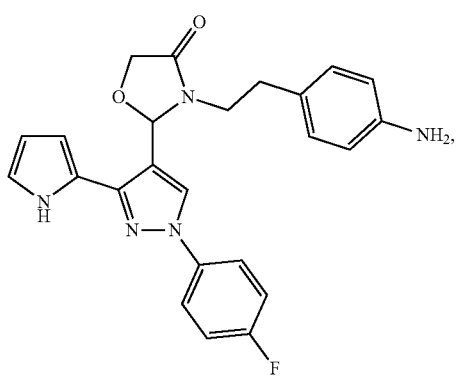
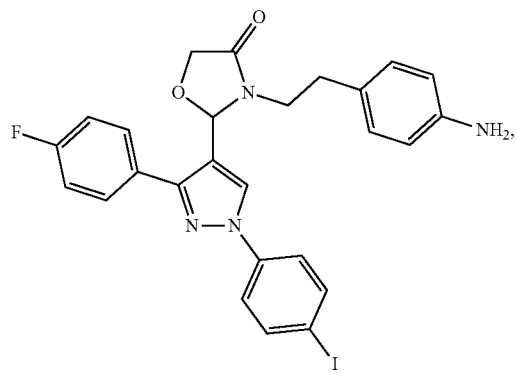
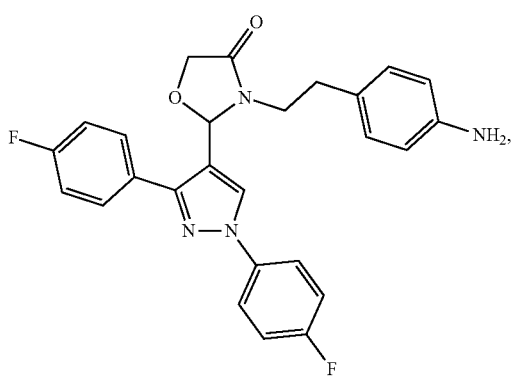
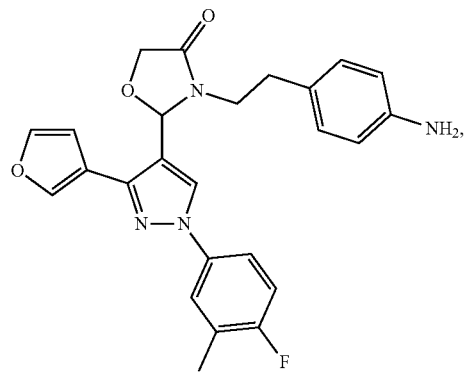
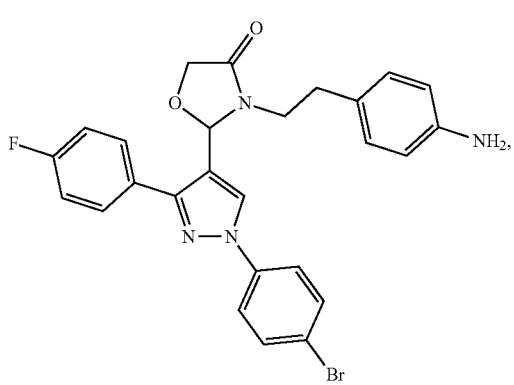
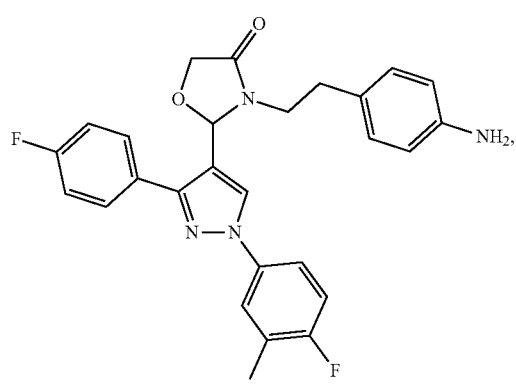

25
-continued
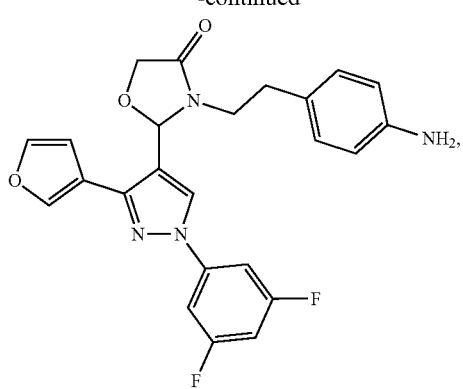
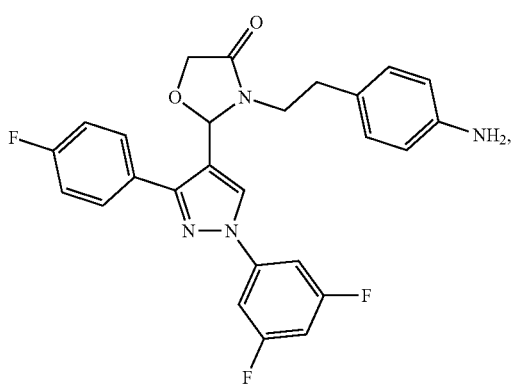
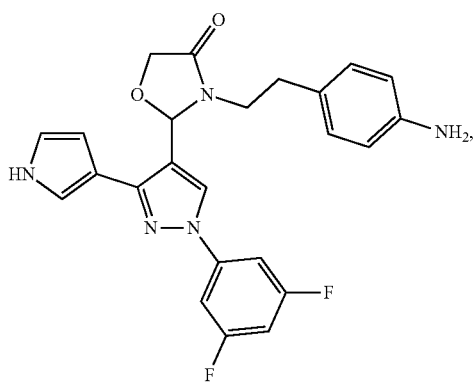
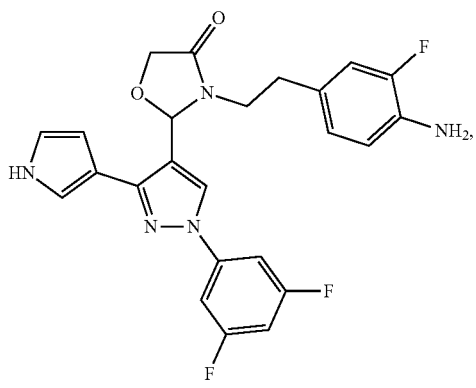
26
-continued
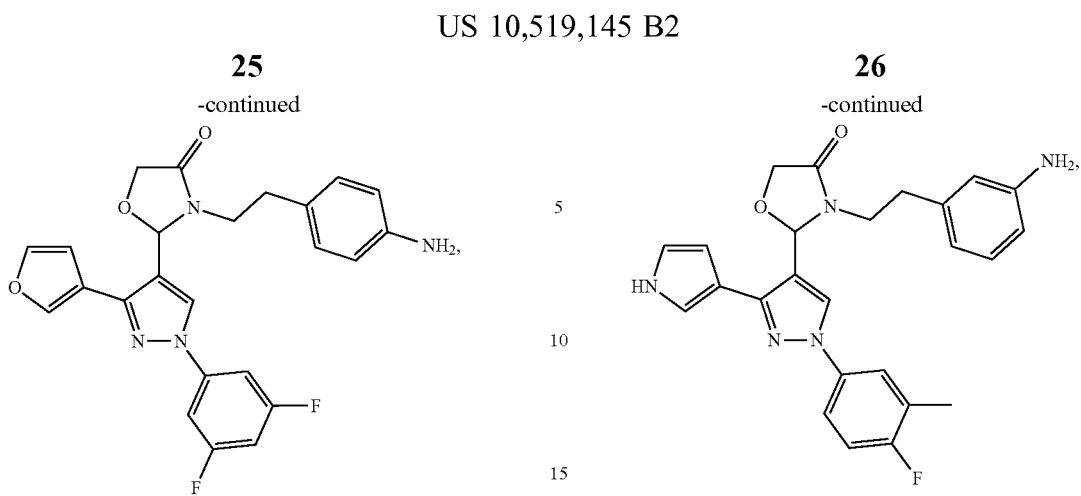
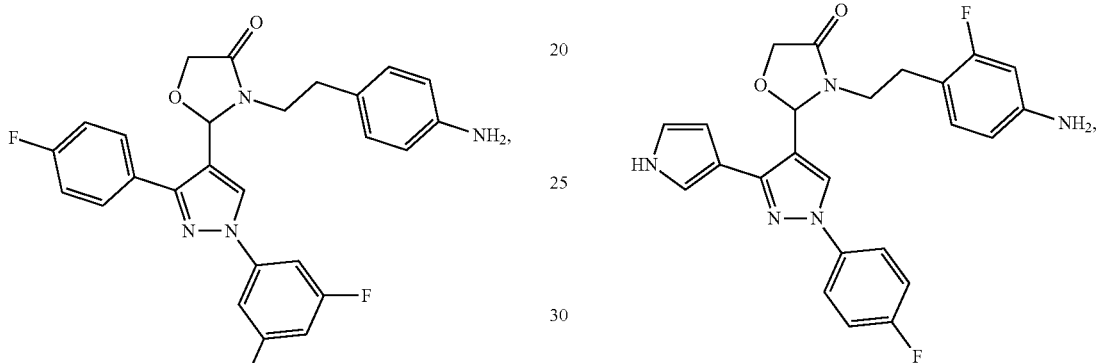
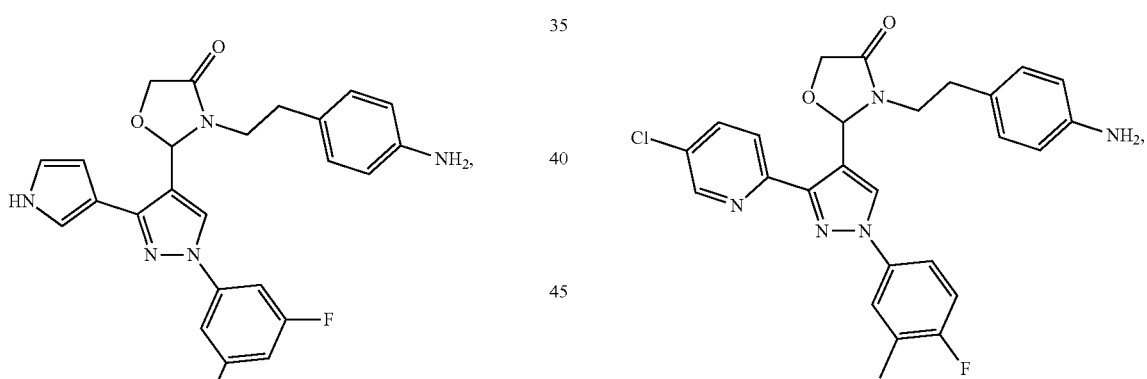
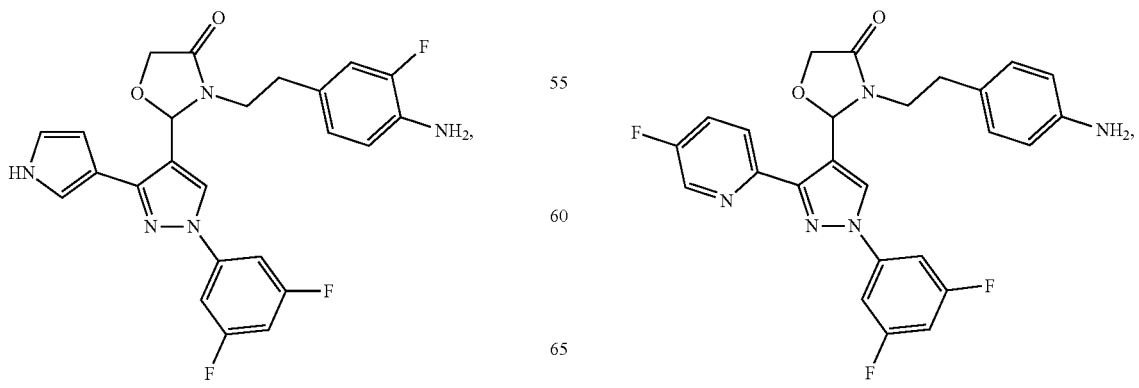

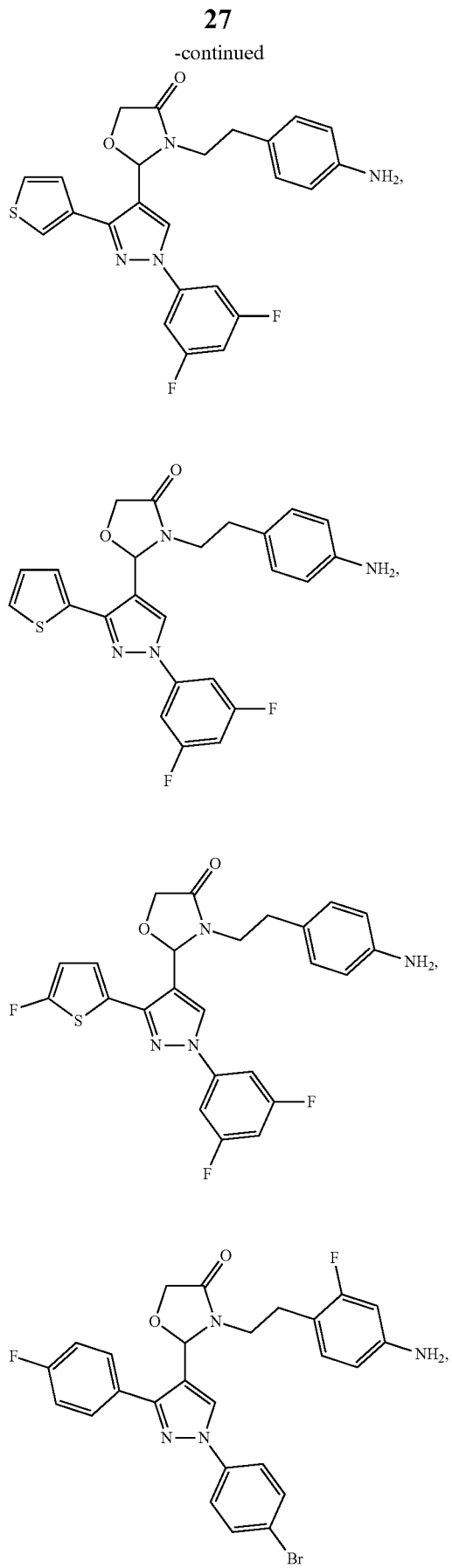

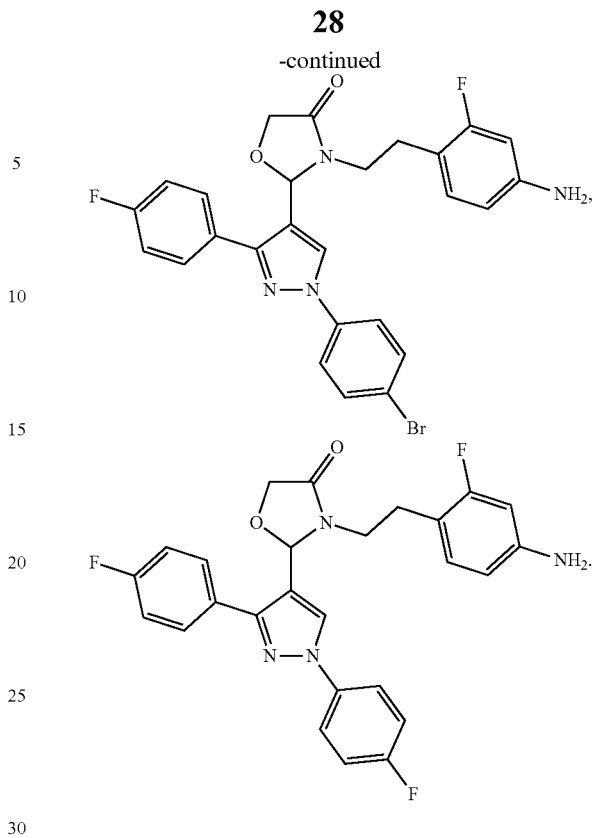

The terms in the present application generally have the following meaning unless otherwise specified.

The term "alkyl" refers to a straight or branched saturated hydrocarbyl group. In the present application, the alkyl group may include 1 to 6 carbon atoms, preferably 1 to 3 carbon atoms. For example, the term "$C_1$-$C_3$ alkyl" refers to a straight or branched saturated hydrocarbyl group having 1 to 3 carbon atoms, including methyl, ethyl, n-propyl, and isopropyl. In the present application, "$C_1$-$C_3$ alkyl" is preferably methyl.

The term "alkoxy" refers to —O-alkyl, wherein the term "alkyl" is as defined above. For example, the term "$C_1$-$C_3$ alkoxy" refers to —O—$C_1$-$C_3$ alkyl.

The term "halogen" is fluorine, chlorine, bromine or iodine. In some embodiments, the halogen is fluorine.

The term "trifluoromethyl" is a —$CF_3$ group.

The term "trifluoromethoxy" is a —$OCF_3$ group.

The term "amino" is a —$NH_2$ group.

The term "heterocyclic group" refers to a non-aromatic cyclic group formed from one or more heteroatoms selected from nitrogen, oxygen and sulfur, and one or more carbon atoms. The heterocyclic group may be a 3- to 8-membered ring system containing 1 to 3 atoms selected from nitrogen, oxygen and sulfur, wherein at least one heteroatom is preferably selected from nitrogen. The saturated carbon atom (ie, —$CH_2$—) in the heterocyclic group may be optionally replaced by —C(=O)—, —C(=S)—, or —C(=NH)—. Examples of heterocyclic group includes, but is not limited to, pyrrolidinyl, pyrrolidonyl, pyrrolinyl, pyrrolinonyl, oxazolidinyl, oxazolidonyl, oxazolineyl, oxazolineonyl, thiazolidinyl, thiazolidonyl, thiazolinyl, and thiazolidonyl. Heterocycle group can be bonded to the rest moities of the molecule through any suitable site on the ring.

The term "aryl" refers to a monocyclic or fused aromatic cyclic hydrocarbyl group containing six to ten carbon atoms. Examples of aryl groups include phenyl and naphthyl, preferably phenyl.

The term "heteroaryl" refers to a fused or non-fused aromatic cyclic group formed by one or more heteroatoms selected from oxygen, nitrogen and sulfur and one or more carbon atoms, and at least one ring is a five- to eight-membered ring containing from 1 to 4 heteroatoms selected from nitrogen, oxygen and sulfur, preferably at least one heteroatom selected from nitrogen. In embodiments where two or more heteroatoms are present in the ring, the two or more heteroatoms may be the same as each other, or some or all of the two or more heteroatoms may be different from each other, provided that the ring does not contain two adjacent O or S atoms. Examples of heteroaryl include, but are not limited to, pyrrolyl, furyl, thienyl, pyrazolyl, imidazolyl, oxazolyl, isoxazolyl, thiazolyl, isothiazolyl, triazolyl, pyridyl, pyrimidinyl, pyrazinyl, pyridazinyl, benzimidazolyl, benzopyrazolyl, indolyl and the like. A heteroaryl group can be bonded to the rest moities of the molecule through any suitable site on the ring. For example, pyrrolyl may be pyrrol-1-yl, pyrrol-2-yl or pyrrol-3-yl; furyl may be furan-2-yl or furan-3-yl; thienyl may be thiophen-2-yl or thiophen-3-yl.

In the present application, when a certain group is defined as "optionally substituted", it may or may not be substituted with one or more groups selected from the following groups as defined herein: alkyl, alkoxyl, halogen, hydroxyl, amino. It will be understood by those skilled in the art that it will not be introduced into any group containing one or more substituents that any substitution or substitution pattern that is sterically impossible and/or cannot be synthesized.

The term "a pharmaceutically acceptable salt" refers to those salts that retain the biological effectiveness and properties of the parent compound, which have the desired pharmaceutical activity and are not biologically or otherwise undesirable. Such salts include, but are not limited to: (1) salts with acids (acid salts) obtained by reacting the free base of the parent compound with inorganic or organic acids; inorganic acids include but not limited to hydrochloric acid, sulfuric acid, phosphoric acid, methanesulfonic acid, and organic acids include but not limited to acetic acid, trichloroacetic acid, propionic acid, butyric acid, maleic acid, p-toluenesulfonic acid, malic acid, malonic acid, cinnamic acid, citric acid, fumaric acid, camphoric acid, digluconic acid, aspartic acid, tartaric acid; (2) salts (basic salt) obtained through that an acidic proton present in a parent compound is replaced with a metal ion or coordinated with an organic base.

Another aspect of the invention relates to a compound of formula I, or a pharmaceutically acceptable salt or enantiomer or tautomer thereof, for use in the inhibition of hepatitis B virus.

Another aspect of the invention relates to a compound of formula I, or a pharmaceutically acceptable salt or enantiomer or tautomer thereof, for use in the treatment of hepatitis B virus infection in a mammal, particularly a human.

Another aspect of the invention relates to a pharmaceutical composition comprising a compound of formula I or a pharmaceutically acceptable salt or enantiomer or tautomer thereof, and a pharmaceutically acceptable carrier.

The purpose of the pharmaceutical composition is to facilitate the administration of the compound to the organism. In general, the compounds of the present invention may be administered in a suitable dosage form with one or more pharmaceutically acceptable carriers. These dosage forms are suitable for oral administration, rectal administration, topical administration, and other parenteral administration (eg, subcutaneous, intramuscular, intravenous, etc.). For example, dosage forms suitable for oral administration include capsules, tablets, granules, syrups and the like. The compounds of the present invention contained in these formulations may be solid powders or granules; solutions or suspensions in aqueous or non-aqueous liquids; water-in-oil or oil-in-water emulsions, and the like. The above-described dosage forms can be prepared from the active compound with one or more pharmaceutically acceptable carriers via a common pharmacy method. A pharmaceutically acceptable carrier refers to an excipient or diluent that does not cause significant irritation to the organism and does not interfere with the biological activity and properties of the administered compound. The above carriers need to be compatible with the active compound or other excipients. For solid formulations, commonly used non-toxic carriers include, but are not limited to, mannitol, lactose, starch, magnesium stearate, calcium carbonate, calcium phosphate, starch, cellulose and derivatives thereof, glucose, sucrose, gelatin, and the like. Carriers for liquid formulations include water, physiological saline, aqueous dextrose solution, vegetable oils, ethylene glycol, polyethylene glycol, and the like. The active compound may form a solution or suspension with the above carrier.

In some embodiments, the pharmaceutical composition is a unit dosage form suitable for single administration of a precise dose. In other embodiments, the amount of the compound is in the range of about 0.001 mg/kg body weight/day to about 1000 mg/kg body weight/day. In some embodiments, the amount of the compound ranges from about 0.5 mg/kg body weight/day to about 50 mg/kg body weight/day. In some embodiments, the amount of the compound is about 0.001 g/day to about 7 g/day. In other embodiments, the amount of compound is from about 0.002 g/day to about 6 g/day. In other embodiments, the amount of the compound is from about 0.005 g/day to about 5 g/day. In other embodiments, dose levels below the lower limit of the above range may already be sufficient. In other embodiments, dose levels above the upper limit of the above range may be required. In some embodiments, the compound is administered in a single dose once daily. In other embodiments, the compound is administered in multiple doses, more than once daily. In some embodiments, the individual to whom the pharmaceutical composition is administered is a mammal. In other embodiments, the mammal is a human. In other embodiments, the pharmaceutical composition further comprises at least one anti-HBV drug. In other embodiments, the pharmaceutical composition and the at least one anti-HBV drug are combined into a combination product in separate dosage four's, respectively.

The pharmaceutical composition of the present invention may further comprise other anti-HBV drugs, which may be HBV polymerase inhibitors, immunomodulators or interferons. Specifically, the other HBV drugs may be lamivudine, telbivudine, tenofovir, entecavir, adefovir dipivoxil, alfaferone, alloferon, celmoleukin, Clevudine, Emtricitabine, Famciclovir, Feilong, Baoganling CP, Intefin, Interferon alpha-1b, Interferon alpha, Interferon alpha-2a, Interferon beta-1a, Interferon alpha-2, Interleukin-2, mivotilate, nitazoxanide, pegylated interferon alfa-2a, ribavirin, Roferon-A, Sizofiran, euforavac, veldona, rintatolimod, phosphazide, heplisav, interferon alpha-2b, levamisole, propagermanium and the like.

These additional drugs may be administered separately from the pharmaceutical compositions containing the compounds of the invention as part of a multiple-dose treatment regimen. Alternatively, such drugs may be part of a single dosage form, mixed with a compound of the invention in a single composition. When administered separately as part of a multiple dose treatment regimen, the two active agents can be administered simultaneously, sequentially, or at intervals between each other to produce the desired activity of these drugs.

Another aspect of the present invention relates to a use of a compound of formula I or a pharmaceutically acceptable salt or enantiomer or tautomer thereof or a pharmaceutical composition of the present invention in the manufacture of a medicament for inhibiting hepatitis B virus.

In one embodiment, the medicament is for treating hepatitis B virus infection in a mammal, particularly a human.

Another aspect of the invention relates to a method of inhibiting hepatitis B virus replication, comprising administering to a subject in need thereof a therapeutically effective amount of a compound of formula I or a pharmaceutically acceptable salt or enantiomer or interconversion thereof or the pharmaceutical composition of the present invention.

In one embodiment, the method is for treating hepatitis B virus infection in a mammal, particularly a human.

In the present application, the term "therapeutically effective amount" may be the amount that relieves one or more symptoms of a disease or disorder in a subject to some extent, makes one or more physiological and biochemical parameters associated with a disease or disorder or as the cause of a disease or disorder partially or completely recover to normal, and/or reduce the likelihood of the onset of a disease or disorder.

In the present application, the diseases involved in the hepatitis B virus infection include acute hepatitis, chronic hepatitis, liver cirrhosis, and hepatocellular carcinoma. The symptoms of an acute hepatitis B virus infection can be asymptomatic or can be the same as acute hepatitis. Patients with chronic viral infections may develop into active disease which may be cirrhosis or liver cancer.

The specific administration method and dosage form depend on the physicochemical properties of the compound itself and the severity of a disease which is applied to.

PCR and enzyme-linked immunesorbent assay (Elisa) can be used to quantify the effect of the compounds of the present application on HBV replication.

The present invention also provides methods for preparing the above compounds, and similar preparation methods are disclosed in PCT/US/06/28343 filed on Jul. 21, 2006. The preparations of the compound of the present invention can be referred to but not limited to the following methods:

Route 1

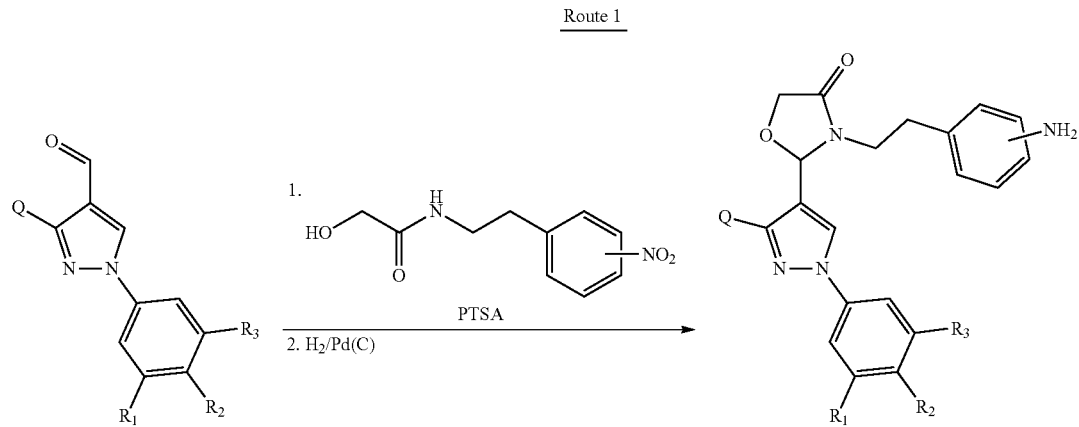

Route 2

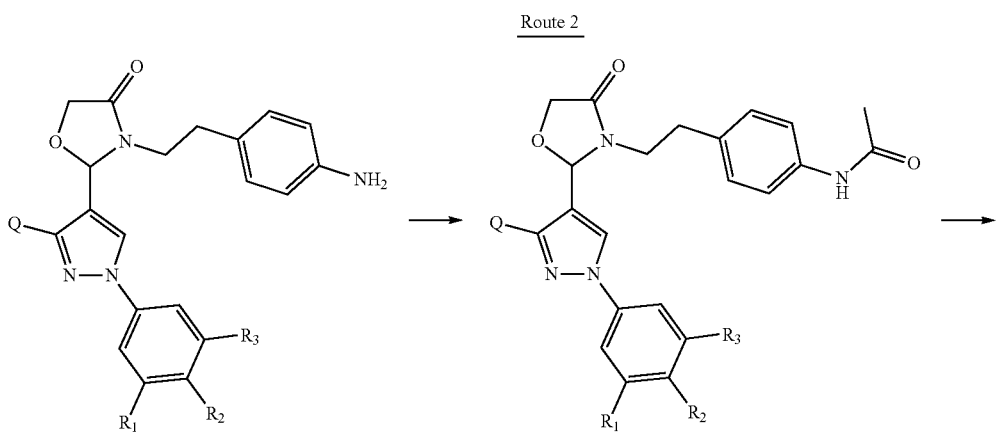

-continued

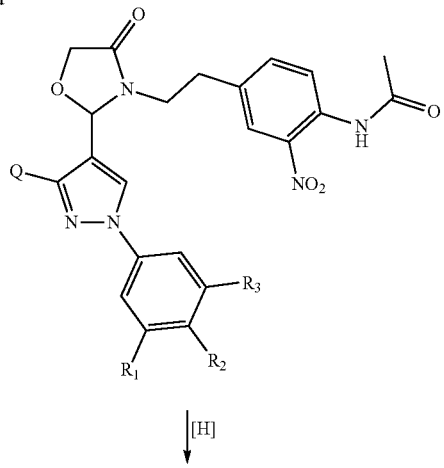

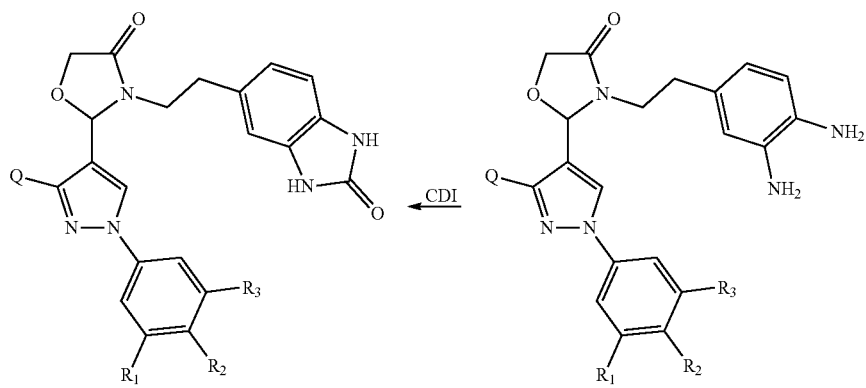

Chiral resolution of the compounds of the present application was accomplished by supercritical fluid chromatography (SFC) according to Berger's method. See Berger, TA "Practical advantages of packed column supercritical fluid chromatography in supporting combinatorial chemistry," *ACS Symposium Series* (2000), 748 (Unified Chromatography), 203-233; Berger, TA; Todd, BS "Packed column supercritical fluid chromatography of oligoethers using pure carbon dioxide with flame ionization and ultraviolet detection" *Chromatographia* (2001), 54 (11/12), 777-781; Berger, TA; Todd, BS "Packed column supercritical fluid chromatography of polysiloxanes using pure and hexane modified carbon dioxide with flame ionization and ultraviolet detection," *Chromatographia* (2001), 54 (11/12), 771-775.

Berger's chiral resolution procedure can be summarized as follows: the racemic mixture (60 mg) is dissolved in methanol (2 mL) and the resulting solution is injected into a preparation chiral column (ChiralPak AD-H SFC, i.d. 1 cm×25 cm). The conditions of SFC are as follows: mobile phase: 65% $CO_2$ and 35% methanol, flow rate: 10 mL/min, detection wavelength: 220 nm. Stereoisomers can be separated at different retention times. The absolute configuration is determined by comparing the crystal diffraction results of CP060 (CP060 is 2-(3,5-di-tert-butyl-4-hydroxyphenyl)-3-[3-[N-methyl-N-[2-[3,4-(methylenedioxy)phenoxy]ethyl] amino]propyl]-1,3-thiazolin-4-one, CP060-(R)-(+), [a]D= +33.3°; CP060-(S)-(−), $[\alpha]_D$=−33.5° (Kato, Tatsuya; Ozaki, Tomokazu; Tamura, Kazuhiko; Suzuki, Yoshiyuki; Akima, Michitaka; Ohi, Nobuhiro, "Novel Calcium Antagonists with Both Calcium Overload Inhibition and Antioxidant Activity. 2. Structure-Activity Relationships of Thiazolidinone Derivatives," *Journal of Medicinal Chemistry* (1999), 42(16), 3134-3146). R configuration of the compound of the present invention is determined based on the above method.

DETAILED DESCRIPTION OF INVENTION

The invention is illustrated by the following non-limiting examples. Those skilled in the art should understand that the embodiments described herein are only used to illustrate and explain the present invention, but are not used to limit the present invention.

EXAMPLE 1

3-(2-(1H-benzo[d]imidazol-5-yl)ethyl)-2-(1-(4-bromophenyl)-3-(4-fluorophenyl)-1H-pyrazol-4-yl)oxazoline-4-one C. The reaction mixture was concentrated in vacuo to dry, then dissolved in dichloromethane, filtered to give a crude product, which was finally washed with petroleum ether to give 145 g of 1-(4-bromophenyl)-2-(1-(4-fluorophenyl)ethylidene) hydrazine. Yield: 59%; MS: 307.0 [M+H]⁺.

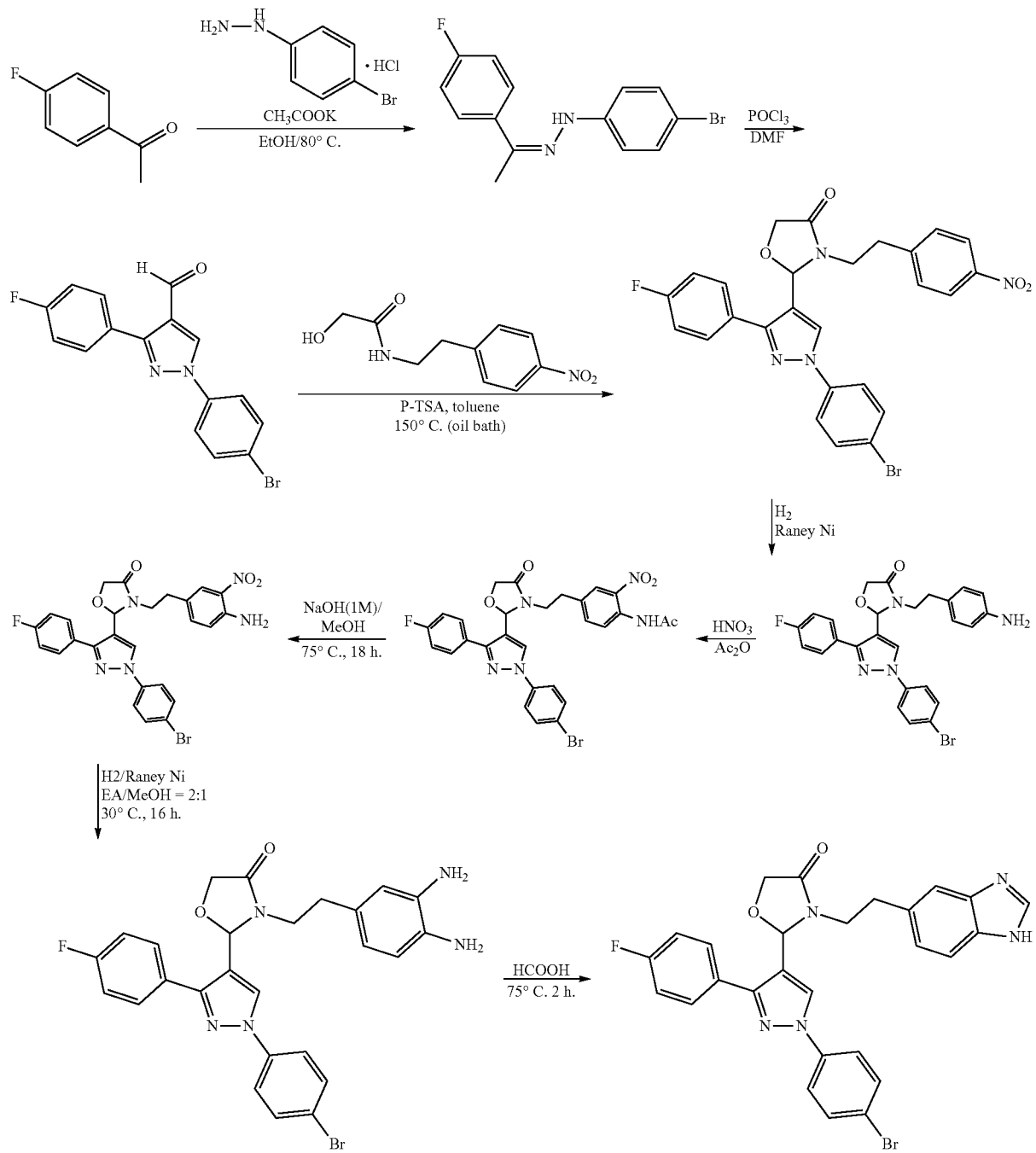

Step 1. 1-(4-bromophenyl)-2-(1-(4-fluorophenyl)ethylidene)hydrazine 1-(4-fluorophenyl)ethanone (113.2 g, 820.6 mmol), 1-(4-bromophenyl)hydrazine hydrochloride (183 g, 820.6 mmol) and potassium acetate (80.4 g, 820.6 mmol) were added into ethanol (1.8 L) and the mixture was stirred overnight at 88°

Step 2. 1-(4-bromophenyl)-3-(4-fluorophenyl)-1H-pyrazol-4-formaldehyde

Phosphorus oxychloride (83.5 mL) was slowly added dropwise to anhydrous DMF (68.75 mL) under anhydrous condition and cooling in an ice bath, and after stirring for 30 min, under nitrogen protection, 1-(4-bromophenyl)-2-(1-(4- fluorophenyl)ethylidene) hydrazine (125 g, 407.2 mmol) was dissolved in a small amount of DMF, which was slowly added dropwise to the reaction mixture. The mixture was stirred at room temperature for 1 h, and warmed up to 70° C. After 5 hours of reaction, the reaction solution was poured into ice water, filtered, washed with acetone and filtered to obtain 145 g of 1-(4-bromophenyl)-3-(4-fluorophenyl)-1H-pyrazol-4-formaldehyde. Yield: 94%.

$^1$H NMR (400 MHz, DMSO-d$_6$) δ 9.97 (s, 1H); 9.39 (s, 1H); 8.03-7.96 (m, 4H); 7.79-4.77 (d, 2H); 7.38-7.33 (m, 2H).

Step 3. 2-(1-(4-bromophenyl)-3-(4-fluorophenyl)-4-1H-pyrazolyl)-3-(4-nitrophenethyl)oxazoline-4-one 1-(4-bromophenyl)-3-(4-fluorophenyl)-1H-pyrazol-4-formaldehyde (72.0 g, 208.7 mmol), 2-hydroxy-N-(4-nitrophenethyl)acetamide (59.0 g, 250.4 mmol) and p-toluenesulfonic acid (21.5 g, 104.4 mmol) were dissolved in 2 liters of toluene. The mixture was heated to reflux with a water separator for 16 hours, then extracted with ethyl acetate, and the solvent was dried by rotary evaporation. The crude product was dispersed in water, and filtered after stirring for 15 min. The cake was dispersed in methanol, filtered after stirring for 30 min. The solvent was dried by rotary evaporation to give 92.0 g of 2-(1-(4-bromophenyl)-3-(4-fluorophenyl)-4-1H-pyrazolyl)-3-(4-nitrophenethyl)oxazoline-4-one. Yield: 94%.

$^1$H NMR (400 MHz, CDCl$_3$) δ 8.03 (d, 2H); 7.86 (s, 1H); 7.65-7.61 (m, 7H); 7.19-7.14 (m, 5H); 5.92 (s, 1H) 4.41-4.28 (m, 2H); 3.91-3.87 (m, 1H); 3.09-3.05 (m, 1H); 2.87-2.82 (m, 2H).

Step 4. 3-(4-aminophenethyl)-2-(1-(4-bromophenyl)-3-(4-fluorophenyl)-4-1H-pyrazolyl)oxazoline-4-one 2-(1-(4-bromophenyl)-3-(4-fluorophenyl)-4-1H-pyrazolyl)-3-(4-nitrophenethyl)oxazoline-4-one (92.0 g, 18.15 mmol) was dissolved in ethyl acetate/methanol (1/1) (2000 mL), Raney Ni (9.2 g) was added, hydrogen gas was introduced, and the mixture was stirred at 30° C. for 16 hours, then filtered and concentrated to give 88 g of 3-(4-aminophenethyl)-2-(1-(4-bromophenyl)-3-(4-fluorophenyl)-4-1H-pyrazolyl)oxazoline-4-one. Yield: 93%; MS: 521.2 [M+H]$^+$.

Step 5: 3-(4-acetamino-3-nitrophenethyl)-2-(3-(4-fluorophenyl)-1-(4-bromophenyl)-1H-pyrazol-4-yl)oxazolidin-4-one 3-(4-aminophenethyl)-2-(1-(4-bromophenyl)-3-(4-fluorophenyl)-4-1H-pyrazolyl)oxazoline-4-one (86.0 g, 165.1 mmol) was dissolved in Ac$_2$O (900 mL) and the mixture was stirred at room temperature for 60 min. After completion of the reaction, it was cooled to 0° C., and then a solution formed by adding HNO$_3$ (65%) (16.0 mL) into ice bath-cooled Ac$_2$O (123 mL) was slowly added to the reaction mixture. The reaction mixture was stirred overnight at 0° C. TLC (methanol: dichloromethane=1:10) showed that the reaction was almost completed. The reaction mixture was then concentrated in vacuo and the crude product was recrystallized from ethyl acetate and filtered to give 3-(4-acetamino-3-nitrophenethyl)-2-(3-(4-fluorophenyl)-1-(4-bromophenyl)-1H-pyrazol-4-yl)oxazolidin-4-one (70 g, 70% yield).

$^1$H NMR (400 MHz, DMSO-d$_6$) δ 10.15 (s, 1H); 8.74 (s, 1H); 7.91-7.29 (m, 13H); 6.17 (s, 1H); 4.31-4.20 (m, 2H); 3.75-3.71 (m, 1H); 3.06-3.01 (m, 1H); 2.79-2.73 (m, 2H); 2.05 (s, 3H).

Step 6. 3-(4-amino-3 nitrophenethyl)-2-(1-(4-bromophenyl)-3-(4-fluorophenyl)-1H-pyrazolyl-4 yl)oxazoline-4 one N-(4-(2-(2-(1-(4-bromophenyl)-3-(4-fluorophenyl)-4-1H-pyrazolyl)-4-oxazoline-3-yl)ethyl)-2-nitrophenyl)acetamide (70 g, 114.6 mmol) was dissolved in methanol (1000 mL) and 1M NaOH (690 mL) and refluxed overnight. The reaction solution was filtered to give 60.0 g of 3-(4-amino-3 nitrophenethyl)-2-(1-(4-bromophenyl)-3-(4-fluorophenyl)-1H-pyrazolyl-4 yl) oxazoline-4 one. Yield 93.8%; MS: 566.1 [M+H]$^+$.

Step 7. 2-(1-(4-bromophenyl)-3-(4-fluorophenyl)-1H-pyrazol-4 yl)-3-(3,4-diaminophenethyl)oxazoline-4 one 3-(4-amino-3 nitrophenethyl)-2-(1-(4-bromophenyl)-3-(4-fluorophenyl)-1H-pyrazol-4 yl)oxazoline-4 one (60.0 g, 106.0 mmol) was dissolved in ethyl acetate/methanol (1/1) (2000 mL), Raney Ni (6.0 g) was added, hydrogen gas was introduced, and the mixture was stirred at 30° C. for 16 hours. The mixture was filtered and concentrated to obtain 55.0 g of 3-(4-aminophenethyl)-2-(1-(4-bromophenyl)-3-(4-fluorophenyl)-4-1H-pyrazolyl)oxazoline-4-one. Yield: 90%.

$^1$H NMR (400 MHz, DMSO-d$_6$) δ 8.72 (s, 1H); 9.71 (d, 2H); 7.74-7.63 (m, 4H); 7.35-7.31 (m, 2H); 6.36 (d, 1H); 6.25 (s, 1H); 6.09-6.06 (d, 3H); 4.39-6.25 (m, 6H); 3.61-3.59 (m, 1H); 2.82-2.79 (m, 1H); 2.39-2.37 (m, 2H). MS: 536.2 [M+H]$^+$.

Step 8. 3-(2-(1H-benzo[d]imidazol-5-yl)ethyl)-2-(1-(4-bromophenyl)-3-(4-fluoro phenyl)-1 H-pyrazol-4-yl)oxazoline-4-one 2-(1-(4-bromophenyl)-3-(4-fluorophenyl)-1H-pyrazol-4-yl)-3-(3,4-diaminophenethyl)oxazoline-4 one (300 mg, 0.56 mmol) was dissolved in 5 mL of formic acid. The reaction solution was stirred at 70° C. for 1 hour and concentrated to dry. The crude product was isolated by reverse phase column chromatography to give a white solid (80 mg, yield: 26%).

$^1$H NMR (400 MHz, DMSO-d$_6$) δ 12.29 (s, 1H); 8.73 (s, 1H); 7.89 (d, J=8.4 Hz, 2H); 7.72 (d, J=8.8 Hz, 2H); 7.59-7.62(m,2H); 7.39-7.41(m,1H); 7.23-7.28(m,3H); 6.89 (d,J=8.4 Hz,1H); 6.05(s,1H); 4.19-4.29 (m, 2H); 3.73-3.80 (m, 1H); 2.95-3.02 (m, 1H); 2.07-2.86 (m, 2H). MS: 548 [M+H]$^+$.

EXAMPLE 2

3-(2-(1H-benzo[d][1,2,3]triazol-5-yl)ethyl)-2-(1-(4-bromophenyl)-3-(4-fluoropheny 1)-1H-pyrazol-4-yl)oxazoline-4-one

EXAMPLE 3

3-(2-(2-oxo-2,3-dihydro-1H-benzo[d]imidazol-5-yl)ethyl)-2-(1-(4-bromophenyl))-3-4-fluoronhenyl)-1H-pyrazo1-4-yl)-oxazolidin-4-one

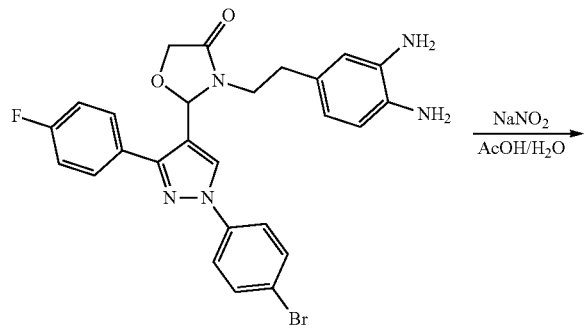

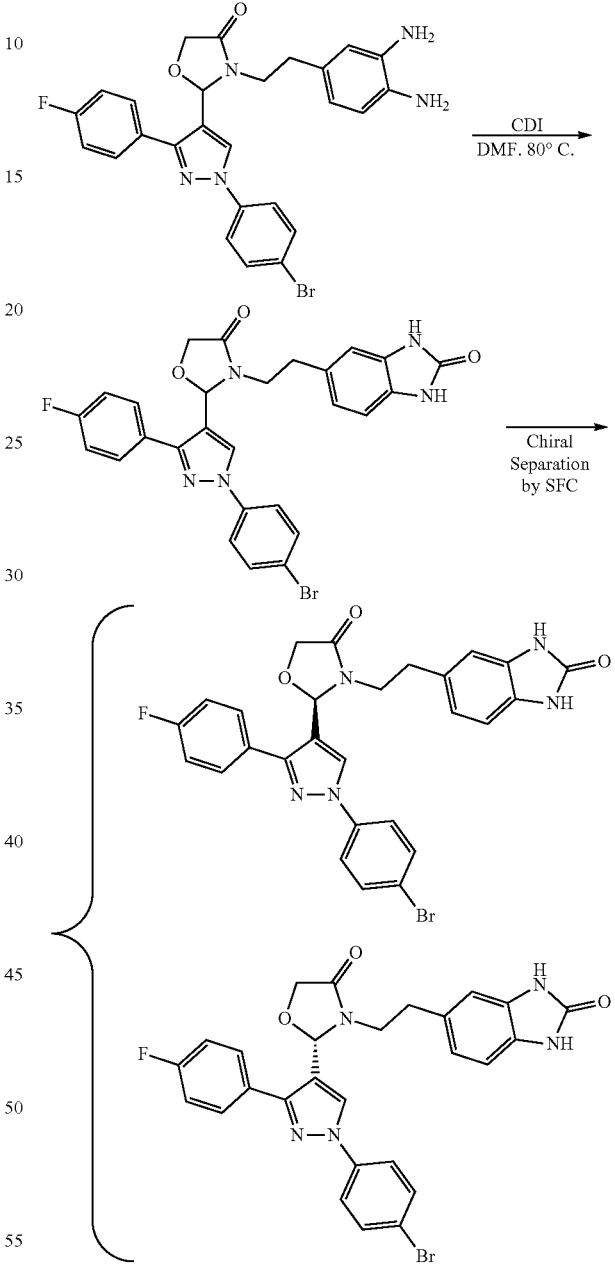

2-(1-(4-bromophenyl)-3-(4-fluorophenyl)-1H-pyrazol-4-yl)-3-(3,4-diaminophenethyl)oxazoline-4 one (300 mg, 0.56 mmol) was dissolved in 5 mL of acetic acid, and a solution of sodium nitrite (58 mg, 0.84 mmol) in 5 mL of water was added. The reaction solution was stirred at room temperature for 2 hours, 50 mi, of water was added, and the mixture was extracted with ethyl acetate (60 mL). The product was extracted with 10% sodium bicarbonate solution and saturated saline, dried over anhydrous sodium sulfate, and concentrated to dry. The crude product was isolated by reverse phase column chromatography to give a white solid (105 mg, yield: 34%).

$^1$H NMR (400 MHz, DMSO-d$_6$) δ 15.53 (s, 1H); 8.75 (s, 1H); 7.89 (d, J=8.8 Hz, 2H); 7.72 (d, J=8.4 Hz, 3H); 7.59-7.63(m,3H); 7.23-7.27(m,2H); 7.14(d,J=8.0 Hz,1H); 6.08(s,1H); 4.19-4.29(m,2H); 3.78-3.85 (m, 1H); 3.02-3.09 (m, 1H); 2.81-2.93 (m, 2H). MS: 549 [M+H]$^+$.

CDI (4.23 g, 26.10 mmol) was added gradually to a solution of 2-(1-(4-bromophenyl)-3-(4-fluorophenyl)-1H-pyrazol-4-yl)-3-(3,4-diaminophenethyl)oxazoline-4 one (7.0 g, 13.05 mmol) in DMF (10 mL). The mixture was stirred under nitrogen at 80° C. for 5 hours. The reaction solution was poured into saturated saline (1000 mL) to precipitate a brown solid. The resulting filter cake was dried in vacuo at 60° C. and purified by silica gel column (dichloromethane: methanol=10: 1) to give 3-(2-(2-oxo-2,3-dihydro-1H-benzo[d]imidazol-5-yl)ethyl)-2-(1-(4-bromophenyl)-3-(4-fluorophenyl)-1H-pyrazol-4-yl)-oxazolidin-4-one (5.56 g, yield: 75.4%) as a pale yellow solid.

$^1$H NMR (400 MHz, CDCl$_3$) δ 10.46-10.45 (d, J=4.8 Hz, 2H); 8.72 (s, 1H); 7.90-7.88 (m, 2H); 7.73-7.71 (d, J=9.2 Hz, 1H); 7.65-7.61 (m, 2H); 7.29 (t, J=8.8 Hz, 2H); 6.71 (t, J=8.0-Hz, 2H); 6.62-6.59 (m, 2H); 6.02 (s, 1H); 4.26-4.24 (m, 2H); 3.89-3.83 (m, 1H); 2.98-2.91 (m, 1H); 2.51-2.50 (m, 2H). MS, m/z: 563.8 (M$^{30}$+H).

3-(2-(2-oxo-2,3-dihydro-1H-benzo[d]imidazol-5-yl) ethyl)-2-(1-(4-bromophenyl)-3-(4-fluorophenyl)-1H-pyrazol-4-yl)-oxazolidin-4-one (87 g) was chiral separated via SFC (column: AS-H; column size: 0.46 cm I.D.×15 cm L; Injection volume: 2.0 μl; Mobile phase: HEP/IPA (0.1% DEA)=60/40 (V/V); Flow rate: 0.5 mL/min; Wavelength: UV 254 nm; Temperature: 35° C.) into two optical isomers.

(R)-3-(2-(2-oxo-2,3-dihydro-1H-benzo[d]imidazol-5-yl) ethyl)-2-(1-(4-bromophenyl)-3-(4-fluorophenyl)-1H-pyrazol-4-yl)-oxazolidin-4-one, white solid, 34.72 g, yield 39.9%. [α]$_D$+41.04° (c 0.5019 g/mL, 19.9° C.); purity: 98.47%, ee: 100.00%.

(S)-3-(2-(2-oxo-2,3-dihydro-1H-benzo[d]imidazol-5-yl) ethyl)-2-(1-(4-bromophenyl)-3-(4-fluorophenyl)-1H-pyrazol-4-yl)-oxazolidin-4-one, white solid, 35.09 g, yield 40.3%. [α] D-39.89° (c 0.5014 g/mL, 20.0° C.); purity: 99.65%, cc: 98.65%.

EXAMPLE 4

3-(2-(2-amino-1H-benzo[d]imidazol-6-yl)ethyl)-2-(1-(4-bromophenyl)-3-(4-fluorophenyl)-1H-pyrazol-4-yl)oxazoline-4-one

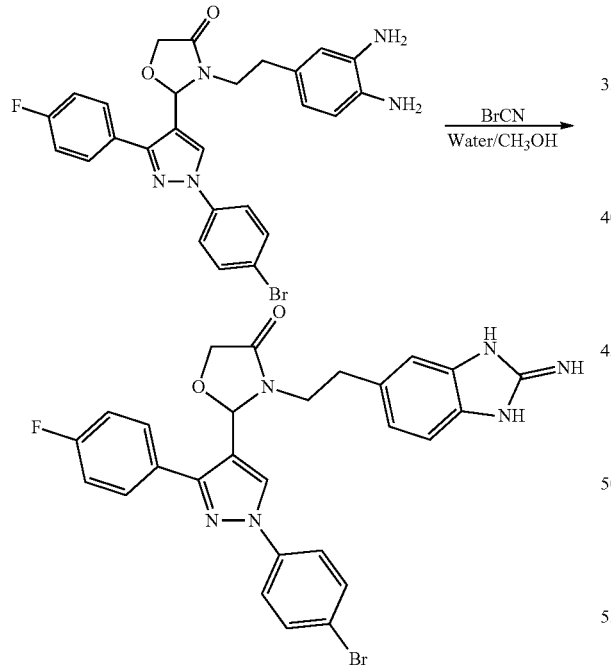

2-(1-(4-bromophenyl)-3-(4-fluorophenyl)-1H-pyrazol-4-yl)-3-(3,4-diaminophenethyl)oxazoline-4 one (140 mg, 0.26 mmol) was dissolved in methanol (8 mL) and water (2 mL). After stirring at room temperature, cyanogen bromide was dissolved in 2 mL of methanol and then added dropwise to the reaction solution. The reaction solution turned cloudy after half an hour, and TLC (dichloromethane: methanol=10: 1) showed that the starting material was consumed. After the reaction solution was diluted with 50 mL of water, the methanol was removed at a low temperature by rotary evaporation, adjusted to basic with 5 ml. of ammonia, and then extracted twice with ethyl acetate (50 mL×2). The organic phase was washed three times with saturated saline, dried over anhydrous sodium sulfate, filtered, concentrated by rotary evaporation and the residue was dissolved in DMF and purified by HPLC to give the target product of 3-(2-(2-amino-1H-benzo[d]imidazole-6-yl)ethyl)-2-(1-(4-bromophenyl)-3-(4-fluorophenyl)-1H-pyrazol-4-yl)oxazoline-4-one as a white solid (30 mg, yield: 20.5%).

$^1$H NMR (400 MHz, DMSO-d$_6$) δ 8.68 (s, 1H); 7.88 (d, J=7.6 Hz, 1H); 7.72 (d, J=7.6 Hz, 2H); 7.59 (s, 2H) 7.27(t, J=8.0 Hz,2H); 6.92(d,J=7.2 Hz,1H); 6.82(s,1H); 6.55 (d,J=6.8 Hz,1H); 6.07 (s,2H); 6.03(s,1H); 4.28-4.1.9(m,2H); 3.72-3.68(m,1H); 2.92-2.89(m,1H); 2.70-2.60(m,2H); MS: 563.2[M+H]$^+$.

EXAMPLE 5

2-(1-(4-bromophenyl)-3-(4-fluorophenyl)-1H-pyrazol-4-yl)-3-(2-(2,3-dihydro-2-thio-1H-benzo[d]imidazol-5-yl)ethyl)oxazoline-4-one

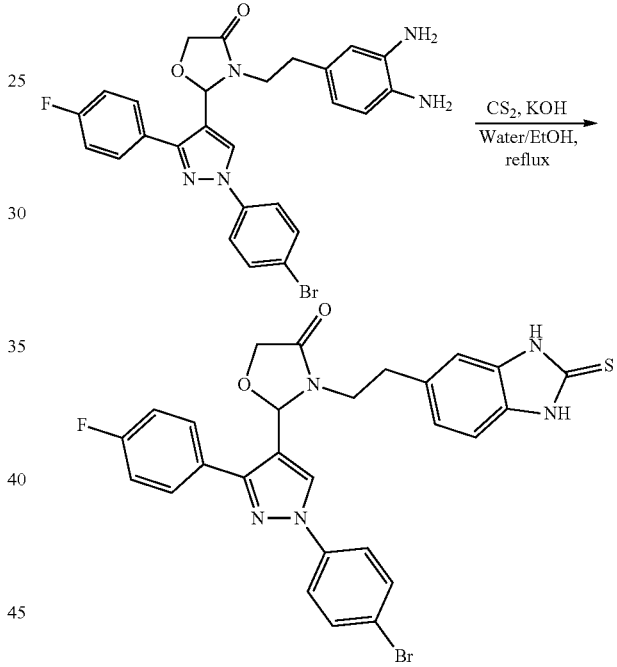

2-(1-(4-bromophenyl)-3-(4-fluorophenyl)-1H-pyrazol-4yl)-3-(3,4-diaminophenethy 1)oxazoline-4 one (100 mg, 0.19 mmol), carbon disulfide (142 mg, 1.87 mmol), and potassium hydroxide (40 mg, 0.71 mmol) were dissolved in ethanol (2.5 mL) and water (0.2 mL) and heated by reflux under argon for two hours. TLC (dichloromethane: methanol=15: 1) showed that the starting material was consumed. The reaction solution was concentrated by rotary evaporation, and the residue was dissolved in. DMF (3 mL), filtered, and purified by HPLC to give the target product of 2-(1-(4-bromophenyl)-3-(4-fluorophenyl)-1H-pyrazol-4-yl)-3-(2-(2,3-dihydro-2-thio-1H-benzo[d]imidazol-5-yl)ethyl)oxazoline-4-one as a white solid (43 mg, yield: 39.8%).

$^1$H NMR (400 MHz, DMSO-d$_6$) δ 12.41 (d, J=4.8 Hz, 2H); 8.71 (s, 1H); 7.88 (d, J=8.0 Hz, 2H); 7.72 (d, J=8.0 Hz, 2H); 7.61 (d, J=4.8 Hz, 2H); 7.29 (t, J=8.2 Hz, 2H); 6.94 (t, J=8.0 Hz, 1H); 6.86 (s, 1H); 6.82(d,J=7.6 Hz,1H);6.03(s, 1H); 4.29-4.20(m,2H); 3.74-3.70(m,1H); 2.97-2.94(m,1H); 2.77-2.50(m, 2H); MS: 580.2 [M+H]$^+$.

EXAMPLE 6

2-(3-(4-fluorophenyl)-1-(4-iodophenyl)-1H-pyrazol-4-yl)-3-(2-(2-oxo-2,3-dihydro-1H-benzo[d]imidazol-5-yl)ethyl)oxazolidin-4-one

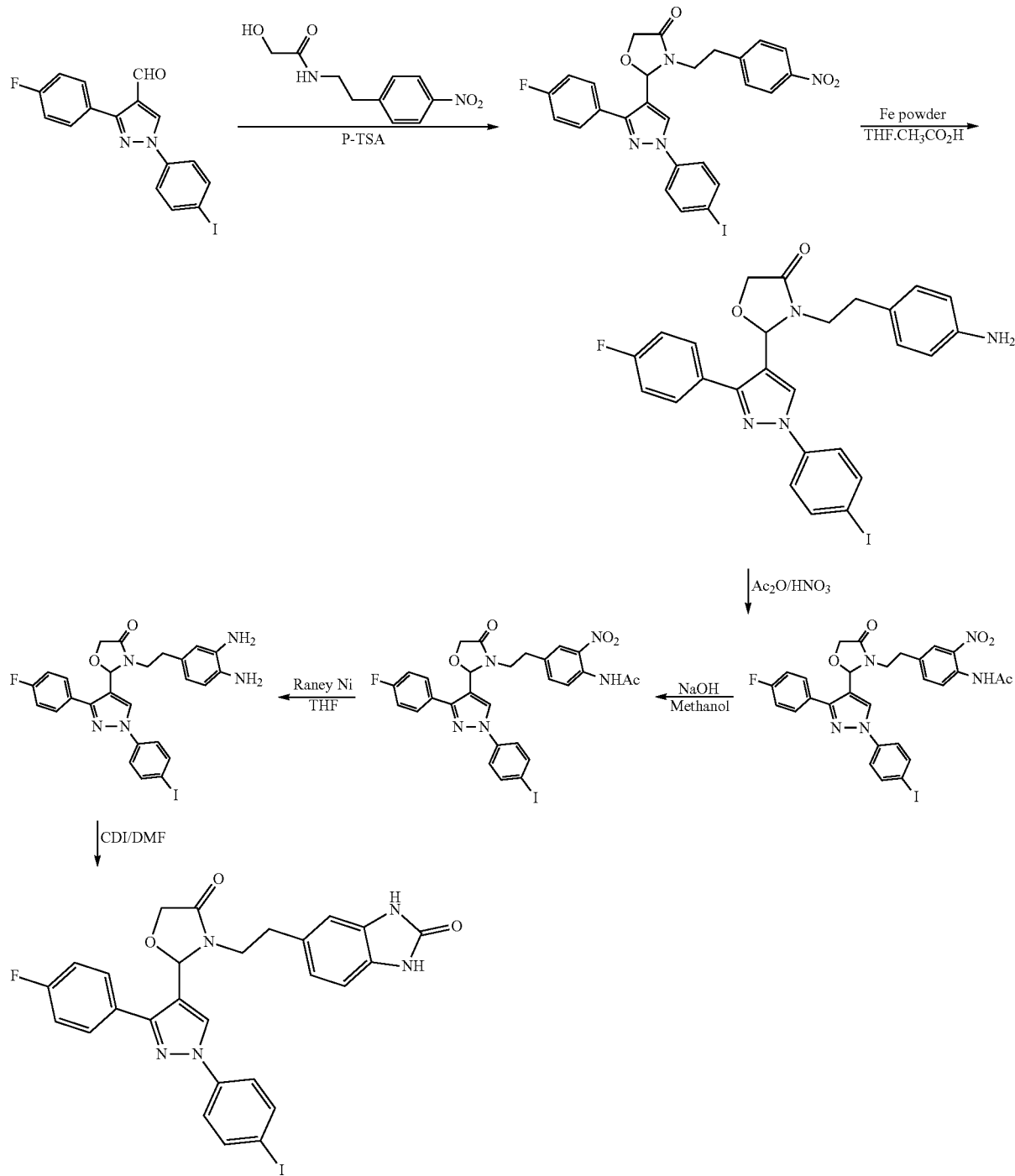

Step 1. 2-(3-(4-fluorophenyl)-1-(4-iodophenyl)-1H-pyrazol-4-yl)-3-(4-nitrophenethyl)oxazolidin-4-one A solution of 3-(4-fluorophenyl)-1-(4-iodophenyl)-1/1-pyrazol-5-formaldehyde (1.18 g, 3 mol), 2-hydroxy-N-(4-methoxyphenethyl)acetamide (741 mg, 3.3 mmol) and p-toluenesulfonic acid (160 mg) in toluene (100 mL) was heated by reflux with water separation overnight. TLC (petroleum ether: ethyl acetate=1:1) showed the reaction was completed. The reaction solution was concentrated and purified by silica gel column (petroleum ether: ethyl acetate=10:1) to give 2-(3-(4-fluorophenyl)-1-(4-iodophenyl)-1H-pyrazol-4-(yl)-3-(4-nitrophenethyl)oxazolidin-4-one (1.78 g, yield: 99.1%) as a yellow solid; MS: m/z: 599 (M$^+$+H).

Step 2. 3-(4-aminophenethyl)-2-(3-(4-fluorophenyl)-1-(4-iodophenyl)-1H-pyrazol-4-yl)oxazolidin-4-one Iron powder (1.4 g) was added to a solution of 2-(3-(4-fluorophenyl)-1-(4-iodophenyl)-1H-pyrazol-4-yl)-3-(4-nitrophenethyl) oxazolidin-4-one (1.5 g, 2.5 mmol) in tetrahydrofuran (100 mL) and acetic acid (100 mL). The mixture was stirred overnight at 60° C. TLC (petroleum ether: ethyl acetate=1:1) showed that the reaction was almost complete. Iron powder was removed by filtration. The filtrate was concentrated in vacuo and purified by silica gel column (petroleum ether: ethyl acetate=5:1) to give 3-(4-aminophenethyl)-2-(3-(4-fluorophenyl)-1-(4-iodophenyl)-1H-pyrazol-4-yl)oxazolidin-4-one (1.2 g, yield: 84.4%) as a yellow solid; MS: m/z: 569 (M$^+$+H).

Step 3. 3-(4-acetamido-3-nitrophenethyl)-2-(3-(4-fluorophenyl)-1-(4-iodophenyl)-1H-pyrazol-4-yl)oxazolidin-4-one To a solution of 3-(4-aminophenethyl)-2-(3-(4-fluorophenyl)-1-(4-iodophenyl)-1H-pyrazol-4-yl)oxazolidin-4-one (1.2 g, 2.11 mmol) in acetic anhydride (12 mL) at 0 ° C. was slowly added dropwise a solution of HNO$_3$ (65%, 5 mL) in acetic anhydride (5 mL). The reaction was stirred overnight at room temperature and TLC (dichloromethane: methanol=15:1) showed the reaction was completed. The reaction mixture was concentrated and purified by silica gel column (dichloromethane: methanol=30:1) to give 3-(4-acetamido-3-nitrophenethyl)-2-(3-(4-fluorophenyl)-1-(4-iodophenyl)-1H-pyrazol-4-yl)oxazolidin-4-one (660 mg, yield: 65.28%) as a brown solid; MS: m/z: 656 (M$^+$+H).

Step 4. 3-(4-amino-3-nitrophenyl)-2-(3-(4-fluorophenyl)-1-(4-iodophenyl)-1H-pyrazol-4-yl)oxazolidin-4-one To a solution of 3-(4-acetamino-3-nitrophenethyl)-2-(3-(4-fluorophenyl)-1-(4-iodophenyl)-1H-pyrazol-4-yl)oxazolidin-4-one (660 mg, 1 mmol) in methanol (10 mL) was added sodium hydroxide solution (40 mg of NaOH dissolved in S mL of water) and the mixture was heated by reflux for 2 hours. TLC (dichloromethane: methanol=10:1) showed the reaction was completed. The reaction solution was concentrated and purified by silica gel column (dichloromethane: methanol=30:1) to give 3-(4-amino-3-nitrophenyl)-2-(3-(4-fluorophenyl)-1-(4-iodophenyl)-1H-pyrazol-4-yl)oxazolidin-4-one (200 mg, yield: 32.6%) as a brown solid; MS: miz: 614 (M$^+$+H.).

Step 5. 3-(3,4-diaminophenethyl)-2-(3-(4- fluorophenyl)-1-(4-iodophenyl)-1H-pyrazol-4-yl)oxazolidin-4-one To a solution of 3-(4-amino-3-nitrophenyl)-2-(3-(4-fluorophenyl)-1-(4-iodophenyl)-1H-pyrazol-4-yl) oxazolidin-4-one (200 mg, 0.327 mmol) in tetrahydrofuran (10 mL) was added Raney Ni (200 mg) and the mixture was stirred at room temperature under hydrogen gas for 5 hours. TLC (dichloromethane: methanol=10:1) showed the reaction was completed. The reaction solution was concentrated and purified by silica gel column (dichloromethane: methanol =50: 1) to give 3-(3,4-diaminophenethyl)-2-(3-(4-fluorophenyl)-1-(4-iodophenyl)-1H-pyrazol-4-yl)oxazolidin-4-one (115 mg, yield: 69.3%) as a brown solid; MS: m/z: 509 (M$^+$+H).

Step 6. 2-(3-(4-fluorophenyl)-1-(4-iodophenyl)-1H-pyrazol-4-yl)-3-(2-(2-oxo-2,3-dihydro-1H-benzo[d]imidazol-5-yl)methyl)oxazolidin-4-one To a solution of 3-(3,4-diaminophenethyl)-2-(3-(4-fluorophenyl)-1-(4-iodophenyl)-1H-pyrazol-4-yl)oxazolidin-4-one (115 mg, 0.197 mmol) in DMF (5 mL) was added CDI (64 mg, 0.394 mmol), and the mixture was stirred at 80° C. for 8 hours. TLC (dichloromethane: methanol=10: 1) showed the reaction was completed. The reaction mixture was quenched with 20 mL of water and extracted with ethyl acetate (20 mL×2). The extracts were collected, washed with saturated saline, dried over anhydrous sodium sulfate, filtered and concentrated, and purified by silica gel column (dichloromethane: methanol=50: 1) to give 2-(3-(4-fluorophenyl)-1-(4-iodophenyl)-1H-pyrazol-4-yl)-3-(2-(2-oxo-2,3-dihydro-1H-benzo[d]imidazol-5-yl)methyl)oxazolidin-4-one (30 mg, yield: 24.9%) as a white solid.

$^1$H NMR (400 MHz, DMSO-d$_6$) δ 10.46-10.44 (d, 2H); 8.71 (s, 1H); 7.88-7.86 (d, 2H); 7.75-7.73 (d, 2H); 7.60(m, 2H);7.30-7.26(t,2H);6.73-6.71(d,J=8.1 Hz,1H);6.63-6.59(t, 2H);6.02(s,1H);4.25-4.20(m, 2H); 3.68-3.69 (m, 1H); 2.92-2.89 (m, 1H); 2.67-2.60 (m, 2H); MS: m/z: 509 (M$^+$+H).

EXAMPLE 7

2-(1-(4-bromophenyl)-3-(4-fluorophenyl)1H-pyrazol-4-yl)-3-(2-(5-fluoro-1H-benzo[d]imidazol-6-yl)ethyl)oxazoline-4-one

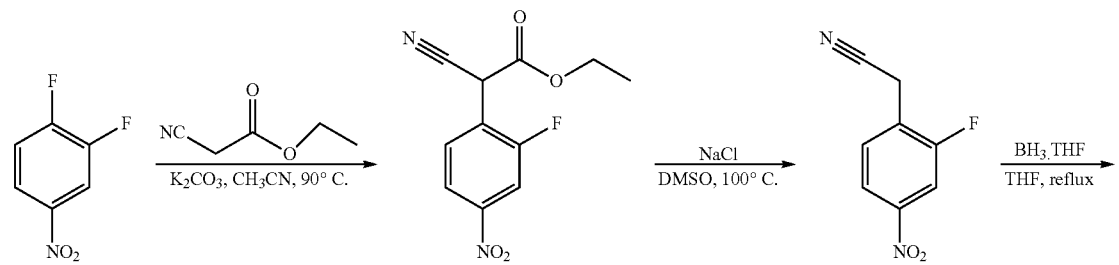

-continued
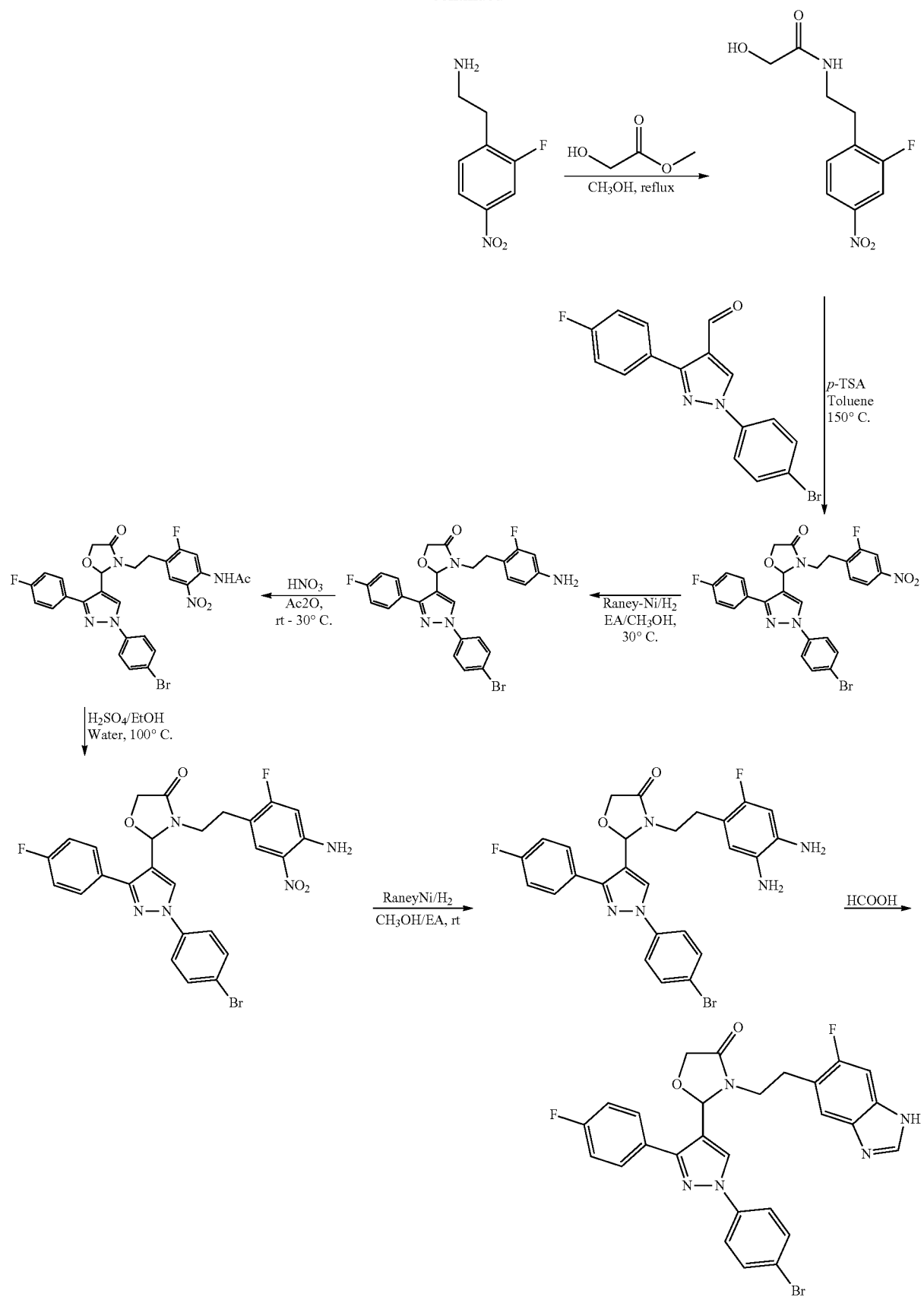

Step 1. 2-cyano-2-(2-fluoro-4-nitrophenyl)ethyl acetate 1,2-difluoro-4-nitro (20 g, 0.13 mol), ethyl cyanoacetate (19 g, 0.16 mol), potassium carbonate (35 g, 0.25 mol) were dissolved in acetonitrile and heated to 90° C. overnight. TLC (petroleum ether: ethyl acetate=10:1) showed that the starting material was consumed. The reaction liquid was dried by rotary evaporation and the crude material was acidified with 2M hydrochloric acid (200 mL) and extracted three times with ethyl acetate (100 mL). The collected ethyl acetate phases were washed twice with brine, dried over anhydrous sodium sulfate, filtered, and the filtrate was dried by rotary evaporation. The crude product was dissolved in dichloromethane and mixed with silica gel and purified by silica gel column (PE: EA=10:1-1:1) to give a compound of ethyl 2-cyano-2-(2-fluoro-4-nitrophenyl)acetate as a brown oil, 31 g, Yield: 97.6%.

$^1$H NMR (400 MHz, CDCl$_3$) δ 8.15 (d, J=8.8 Hz, 1H); 8.05 (d, J=9.2 Hz, 1H); 7.77 (t, J=8.0 Hz, 1H); 5.11 (s, 1H); 4.34-4.35 (m, 2H); 1.35-1.26 (m, 3H).

Step 2. 2-(2-difluoro-4-nitrophenyl)acetonitrile

Ethyl 2-cyano-2-(2-fluoro-4-nitrophenyl)acetate (31 g, 0.12 mol), sodium chloride (15 g, 0.25 mol), and water (0.13 mL, 0.12 mol) were dissolved in dimethyl sulfoxide (200 mL), then heated to 100° C. overnight. TLC (petroleum ether: ethyl acetate=2:1) showed that the starting material was consumed. The reaction solution was cooled to room temperature, quenched by being added to 1 liter of water, and extracted three times with 200 mL of ethyl acetate. The collected organic phases were washed three times with brine, dried over anhydrous sodium sulfate, filtered, and the filtrate was dried by rotary evaporation. The crude product was purified by silica gel column (petroleum ether: ethyl acetate=10:1-2:1) to give 2-(2-difluoro-4-nitrophenyl)acetonitrile as a red-brown solid, 20 g, yield: 90.3%.

Step 3. 2-(2-Fluoro-4-nitrophenyl)ethanamine 2-(2-difluoro-4-nitrophenyl)acetonitrile (20 g, 0.11 mol) was dissolved in 80 mL of tetrahydrofuran, and a 1M solution of borane in tetrahydrofuran (150 mL, 0.15 mol) was added dropwise under cooling in ice bath. After the addition was completed, it was returned to room temperature and heated to 80° C. for two hours under reflux. TLC (petroleum ether: ethyl acetate=2:1) showed that most of the starting material was consumed. The reaction solution was cooled to room temperature, and methanol was added dropwise under cooling in ice bath until no bubble formed in the reaction solution. The reaction solution was concentrated by rotary evaporation to give a black oil (22 g, yield: 108%), which was used directly in the next reaction; MS: 185.1 [M+H]$^+$.

Step 4. N-(2-Fluoro-4-nitrophenethyl)-2-hydroxyacetamide 2-(2-Fluoro-4-nitrophenyl)ethanamine (22 g, 118. mmol), and methyl glycolate (40 g, 444.4 mmol) were dissolved in 100 mL of methanol and heated at reflux for two days. TLC (dichloromethane: methanol=10:1) showed that the starting material was consumed. The reaction solution was cooled to room temperature and concentrated by rotary evaporation. The crude product was purified by silica gel column (petroleum ether: ethyl acetate=5:1-1:2) to give a compound of N-(2-fluoro-4-nitrophenethyl)-2-hydroxyacetamide as a black solid, 12 g, yield: 42%; MS: 243.3 [M+H]$^+$.

Step 5. 2-(1-(4-bromophenyl)-3-(4-fluorophenyl)-1H-pyrazolyl-4 yl)-3-(2-fluoro-4-nitrophenethyl)oxazoline-4 one N-(2- fluoro-4-nitrophenethyl)-2-hydroxyacetamide (4 g, 16.53 mmol), 1-(4-bromophenyl)-3-(4-fluorophenyl)-1H-pyrazol-4-formaldehyde (5.88 g, 17.21 mmol) and p-toluenesulfonic acid monohydrate (1.57 g, 8.26 mmol) were dissolved in 100 mL of toluene, and the mixture was heated at 150° C. and water-separated overnight with a water separator. TLC (petroleum ether: ethyl acetate=2:1) showed that the starting material was consumed. The reaction solution was concentrated by rotary evaporation and purified by silica gel column (petroleum ether: ethyl acetate=2:1-0:1) to give a compound of 2-(1-(4-bromophenyl)-3-(4-fluorophenyl)-1H-pyrazol y1-4 yl)-3-(2-fluoro-4-nitrophenethyl)oxazoline-4-one as a crude product, which was then slurried with ethyl acetate and filtered, and the filter cake was dried in an oven to give a white solid (4.5 g, yield: 48%); MS: 569.1 [M+H]$^+$.

$^1$H NMR (400 MHz, DMSO-d$_6$) δ 8.77 (s, 1H); 7.90 (d, J=7.2 Hz, 4H); 7.73-7.66 (m, 4H); 7.51 (t, J=8.0 Hz , 1H); 7.30 (t, J=8.8 Hz, 2H); 6.14 (s, 1H); 4.32-4.22 (m, 2H); 3.78-3.71 (m, 1H); 3.11-3.04 (m, 1H); 2.86(s,2H).

Step 6. 3-(4-Amino-2-fluorophenethyl)-2-(1-(4-bromophenyl)-3-(4-fluorophenyl)-1H-pyrazol-4-yl)oxazoline-4-one 2-(1-(4-bromophenyl)-3-(4-fluorophenyl)-1H-pyrazolyl-4 yl)-3-(2-fluoro-4-nitrophenethyl)oxazoline-4 one (4.5 g, 7.92 mmol) was dissolved in ethyl acetate (50 mL)/methanol (100 mL), Raney Ni (100 mg) was added, and the reaction was hydrogenated with a hydrogen balloon at normal pressure at 30° C. After 1 hour of reaction, the reaction was stopped, and the reaction solution was filtered. The filter cake was washed with ethyl acetate, and the filtrate was dried by rotary evaporation to give the target product (white solid, 4.2 g, yield: 98.5%). The compound was used directly in next reaction without purification.

$^1$H NMR (400 MHz, DMSO-d$_6$) δ 8.77 (s, 1H); 7.91 (d, J=8.8 Hz, 2H); 7.73 (d, J=8.4 Hz, 2H); 7.66 (t, J=7.6 Hz, 2H); 7.33 (t, J=8.3 Hz, 1H); 6.75 (t, J=8.4 Hz, 1H); 6.25-6.16 (m, 3H); 5.25 (s, 2H)); 4.30-4.20 (m, 2H); 3.64-3.57 (m, 1H); 2.86-2.79 (m, 1H); 2.59-2.42 (m, 2H); MS: 541.1 [M+H]$^+$.

Step 7. 3-(2-fluoro-5-nitro-4-acetaminophenethyl)-2-(3-(4-fluorophenyl)-1-(4-bromophenyl)-1H-pyrazol-4-yl)oxazolidin-4-one 3-(4-amino-2-fluorophenethyl)-2-(1-(4-bromophenyl)-3-(4-fluorophenyl)-1H-pyrazol-4-yl)oxazolin-4-one (4.2 g, 7.8 mmol) was dissolved in 30 mL of acetic anhydride and the reaction was stirred at room temperature for 20 min. The reaction solution turned from clear to turbid, and TLC (petroleum ether: ethyl acetate=1:1) showed that the starting material was consumed. Under cooling in ice bath, 65% concentrated nitric acid (2.12 g, 21.86 mmol) was slowly added dropwise to the reaction solution. After the dropwise addition was completed, the ice bath was removed and the mixture was stirred overnight. TLC (petroleum ether: ethyl acetate=1:1) showed that the starting material was consumed. The reaction was diluted with ethyl acetate (100 mL), washed once with water and brine respectively, then dried over anhydrous sodium sulfate, filtered, and the filtrate was concentrated by rotary evaporation. The crude product was purified by silica gel column (petroleum ether: ethyl acetate=5:1-1:1) to give a compound of 3-(2-fluoro-5-nitro-4-acetaminophenethyl)-2-(3-(4-fluorophenyl)-1-(4-bromophenyl)-1H-pyrazol-4-yl)oxazolidin-4-one as a yellow solid, which is then slurried with ethyl acetate and filtered. The filter cake was dried in an oven to give a pale yellow solid (2.4 g, yield: 49.2%).

$^1$H NMR (400 MHz, DMSO-$d_6$) δ 10.23 (s, 1H); 8.76 (s, 1H); 7.95 (d, J=7.2 Hz, 1H); 7.89 (d, J=8.8 Hz, 2H) 7.73-7.68 (m, 4H); 7.59 (d, J=11.6 Hz, 1H); 7.31 (t, J=8.8 Hz, 1H); 6.24 (s, 1H); 4.30-4.20 (m, 2H);3.74-3.67 (m, 1H); 3.06-3.01 (m, 1H); 2.79-2.77 (m, 2H); MS;626.2 [M+H]$^+$.

Step 8. 3-(2-fluoro-4-amino-5-nitrophenethyl)-2-(1-(4-bromophenyl)-3-(4-fluorophenyl)-1H-pyrazol-4-yl)oxazoline-4-one N-(4-(2-(2-(1-(4-bromophenyl)-3-(4-fluorophenyl)-1H-pyrazol-4-yl)-4-oxazoline-3-yl)ethyl)-3-fluoro-2-nitrophenypacetamide (1.8 g, 2.88 mmol) was dissolved in 20 mL of ethanol, 2 mL of concentrated sulfuric acid was added, and the mixture was heated under reflux for 2 hours and concentrated under reduced pressure. The residue was diluted with ethyl acetate (40 mL), stirred with ice water (100 mL), adjusted pH to neutral with saturated sodium bicarbonate, extracted with ethyl acetate (40 mL), washed with saturated saline, dried over anhydrous sodium sulfate, and dried with rotary evaporation. The crude product was separated by column chromatography (petroleum ether: ethyl acetate=3:1) to give the target product 3-(2-fluoro-4-amino-5-nitrophenethyl)-2-(1-(4-bromophenyl)-3-(4 fluorophenyl)-1H-pyrazol-4-yl)oxazoline-4-one as a yellow solid (0.8 g, yield: 47.6%).

$^1$H NMR (400 MHz, DMSO-$d_6$) δ 8.79 (s, 1H); 7.90 (d, J=8.4 Hz, 1H); 7.85 (d, J=7.6 Hz, 1H); 7.74-7.67 (m,4H);7.45(s,2H);7.30(t,J=8.6 Hz,2H);6.62(d,J=12.4 Hz,1H); 6.24(s,1H);4.30-4.20(m,2H) 3.69-3.34 (m, 1H); 2.96-2.92 (m, 1H); 2.66-2.57 (m, 2H); MS: 586.1 [M+H]$^+$.

Step 9. 2-(1-(4-bromophenyl)-3-(4-fluorophenyl) 1H-pyrazol-4-yl)-3-(4,5-diamino-2- fluorophenethyl)oxazoline-4-one 3-(2- fluoro-4-amino-5-nitrophenethyl)-2-(1-(4-bromophenyl)-3-(4 fluorophenyl)-1H-pyrazol-4-yl)oxazoline-4-one (200 mg, 0.33 mmol) was dissolved in 50 mL of ethyl acetate and 100 mL of methanol, Raney Ni (50 mg) was added and the reaction was hydrogenated at atmospheric pressure. After 1 hour of reaction, the reaction was stopped, the reaction solution was filtered, the filter cake was washed with methanol, and the filtrate was dried by rotary evaporation to obtain the desired product as a brown solid (0.7 g, yield: 94%). This compound was used for the next reaction without purification.

$^1$H NMR (400 MHz, DMSO-$d_6$) δ 8.77 (s, 1H); 7.91 (d, J=8.0 Hz, 2H); 7.72 (d, J=8.0 Hz, 2H); 7.64 (s, 2H) 7.33(t, J=8.4 Hz,2H); 6.23-6.14(m,3H); 4.65(s,2H); 3.58-3.55(m, 1H); 2.81-2.78(m,1H);2.41-2.40 (m, 2H); MS: 556.1 [M+H]$^+$.

Step 10. 2-(1-(4-bromophenyl)-3-(4-fluorophenyl) 1H-pyrazol-4-yl)-3-(2-(5-fluoro-1H-benzo[d]imidazol-6-yl)ethyl)oxazoline-4-one 2-(1-(4-bromophenyl)-3-(4-fluorophenyl)1H-pyrazol-4-yl)-3-(4,5-diamino-2-fluoro phenethyl)oxazoline-4-one (280 mg, 0.51 mmol) was dissolved in 5 mL of formic acid. The reaction solution was stirred at 70° C. for 1 hour, concentrated to dry, diluted with ethyl acetate, and adjusted pH to neutral with saturated sodium bicarbonate. The organic phase was washed with saturated saline, dried over anhydrous sodium sulfate, and filtered. The filtrate was concentrated by rotary evaporation and the crude product was isolated by reverse phase column chromatography to give a white solid (120 mg, yield: 42.1%).

$^1$H NMR (400 MHz, DMSO-$d_6$) δ 12.40 (s, 1H); 8.78 (s, 1H); 8.17 (s, 1H); 7.90 (d, J=8.8 Hz, 2H); 7.73 (d, J=8.8 Hz, 2H); 7.64 (t, J=6.8 Hz, 2H); 7.37 (s, 1H); 7.27 (t, J=8.8Hz, 2H); 6.17 (s, 1H); 4.31-4.21 (m, 2H); 3.79-3.73 (m, 1H); 3.03-2.96 (m, 1H); 2.89-2.74 (m, 2H); MS: 566.1 [M+H]$^+$.

EXAMPLE 8

2-(1-(4-bromophenyl)-3-(4-fluorophenyl)1/-pyrazol-4-yl)-3-(2-(6-fluoro-2-carbonyl-2,3-dihydro-1H-benzo[d]imidazol-5-yl)ethyl)oxazoline-4-one

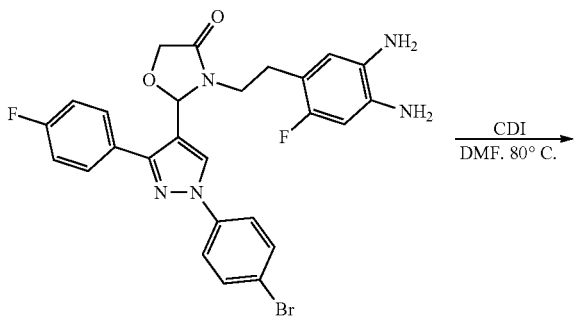
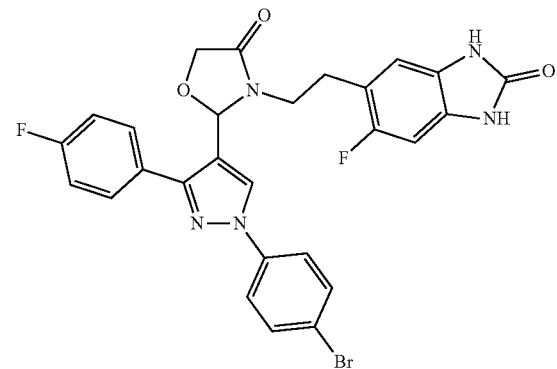

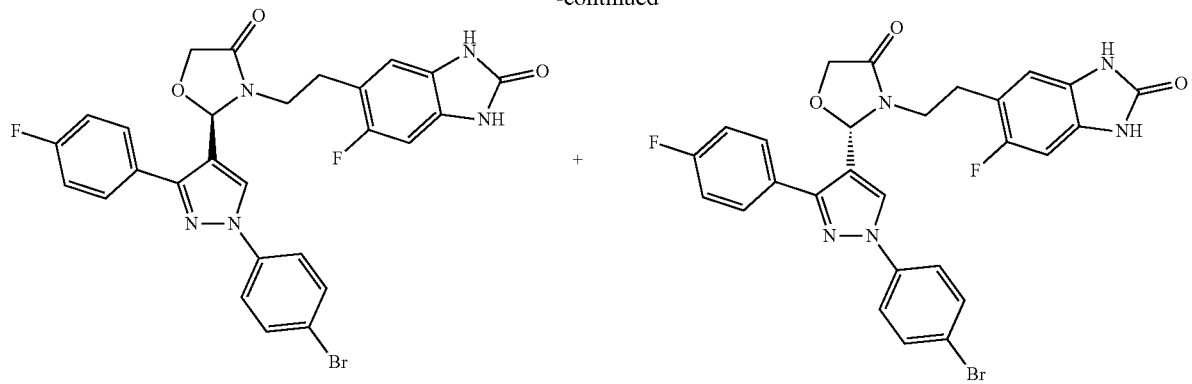

2-(1-(4-bromophenyl)-3-(4-fluorophenyl)-1H-pyrazol-4-yl)-3-(3,4-diamino-2-fluorophenethyl)oxazoline-4-one (300 mg, 0.54 mmol), and CDI (106 mg, 0.65 mmol) were dissolved in DMF (5 mL), and the mixture was stirred under nitrogen at 80° C. for 2 hours. After the reaction was completed, the reaction mixture was poured into water (100 mL), extracted twice with ethyl acetate (50 mL), and the organic phases were collected and washed once with saturated saline, dried over anhydrous sodium sulfate, filtered, and the filtrate was dried by rotary evaporation, and the crude product was purified by silica gel column (dichloromethane: methanol =1: 0-40: 1) to give the target product as a white solid (200 mg, yield: 64%).

$^1$H NMR (400 MHz, DMSO-d$_6$) δ 10.64 (s, 1H); 10.55 (s, 1H); 8.77 (s, 1H); 7.90 (d, J=8.4 Hz, 2H); J=8.4 Hz, 2H); 7.65 (t, J=7 Hz, 2H); 7.29 (t, J=8.4 Hz, 2H); 6.67-6.60 (m, 2H); 6.13 (s, 1H); 4.30-4.20 (m, 2H); 3.70 (m, 1H); 2.91 (m, 1H); 2.74-2.62 (m, 2H); MS: 580.2 [M+H]$^+$.

2-(1-(4-bromophenyl)-3-(4-fluorophenyl)1H-pyrazol-4-yl)-3-(2-(6-fluoro-2-carbon yl-2,3-dihydro-1H-benzo[d]imidazol-5-yl)ethyl)oxazoline-4-one (19.5 g) was chiral separated via SFC (Column: OJ-H; Column size: 0.46 cm I.D.×15 cm L; Injection volume: 2.0 μl; Mobile phase: HEP/EtOH=60/40 (V/V); Flow rate: 0.5 mL/min; Wavelength: UV 254 nm; Temperature: 25° C.) to give two optical isomers.

(S)-2-(1-(4-bromophenyl)-3-(4-fluorophenyl)1H-pyrazol-4-yl)-3-(2-(6-fluoro-2-carbonyl-2,3-dihydro-1H-benzo[d]imidazol-5-yl)ethyl)oxazoline-4-one, white solid, 7.48 g, yield 38.4%. t$_R$ 3.557 min, [α]$_D$ –38.78° (c 0.5261 g/100 mL, 21.4° C.); purity: 99.62%, ee: 100.0%.

(R)-2-(1-(4-bromophenyl)-3-(4-fluorophenyl)1H-pyrazol-4-yl)-3-(2-(6-fluoro-2-carbonyl-2,3-dihydro-1H-benzo[d]imidazol-5-yl)ethyl)oxazoline-4-one, white solid, 7.98 g, yield 40.9%. t$_R$ 5.784 min, [α]$_D$ +37.20° (c 0.4893 g/100 mL, 19.7° C.); purity: 98.93%, ee: 99.02%.

EXAMPLE 9

3-(2-(5-fluoro-1H-benzo[d][1,2,3]triazol-6-yl)ethyl)-2-(1-(4-bromophenyl)-3-(4-fluorophenyl)-1H-pyrazol-4-yl)oxazoline-4-one

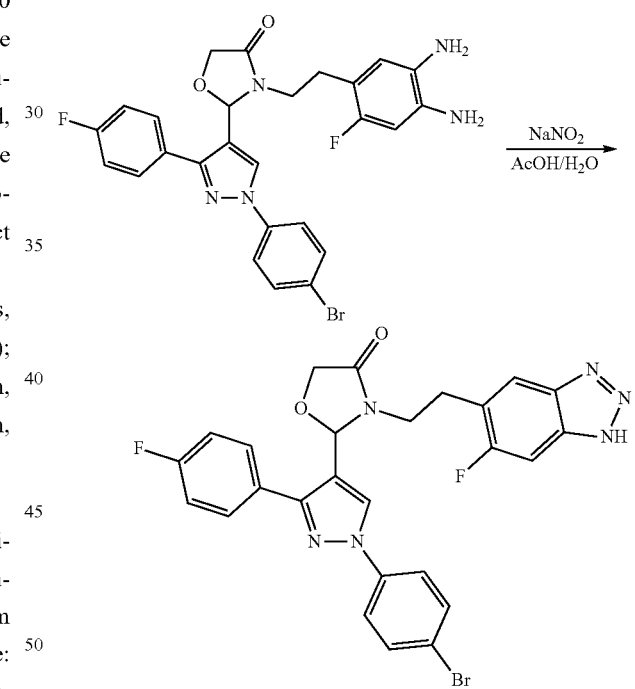

2-(1-(4-bromophenyl)-3-(4-fluorophenyl)1H-pyrazol-4-yl)-3-(3,4-diamino-2-fluoro phenethyl)oxazoline-4-one (160 mg, 0.29 mmol) was dissolved in glacial acetic acid (5 mL) and water (1 mL). Under cooling in ice bath, sodium nitrite (40 mg, 0.578 mmol) was dissolved in 2 ml of water and then added dropwise to the reaction solution. After half an hour TLC (dichloromethane: methanol=15:1) showed that the starting material was consumed. The reaction solution was poured into 100 mL of ice water, adjusted to basic with saturated sodium bicarbonate, and extracted twice with ethyl acetate (50 mL×2). The collected organic phases were washed three times with brine, dried over anhydrous sodium sulfate, and filtered. The filtrate was concentrated by rotary evaporation and the residue was dissolved in DMF and purified by HPLC to give the target product of 2-(1-(4-bromophenyl)-3-(4-fluorophenyl)-1H-pyrazol-4-yl)-3-(2-(5-fluoro-1H-benzo[d][1,2,3]triazol-6-yl)ethyl)oxazoline-4-one as a white solid (65 mg, yield: 39.8%).
$^1$H NMR (400 MHz, DMSO-d$_6$) δ 8.78 (s, 1H); 7.89 (d, J=8.4 Hz, 2H); 7.78 (d, J=4.8 Hz, 1H); 7.72 (d, J=8.0 Hz, 2H); 7.64 (s, 2H)); 7.26 (t, J=9.2 Hz, 2H); 6.22 (s, 1H); 4.29-4.19 (m, 2H); 3.81-3.76 (m, 1H); 3.07-3.04 (m, 1H); 2.87-2.83 (m, 2H); MS: 567.2 [M+H]$^+$.
EXAMPLE 10
2-(1-(4-bromophenyl)-3-(4-fluorophenyl)1H-pyrazol-4-yl)-3-(2-(5,7-difluoro-1H-benzo[d]imidazol-6-yl)ethyl)oxazoline-4-one
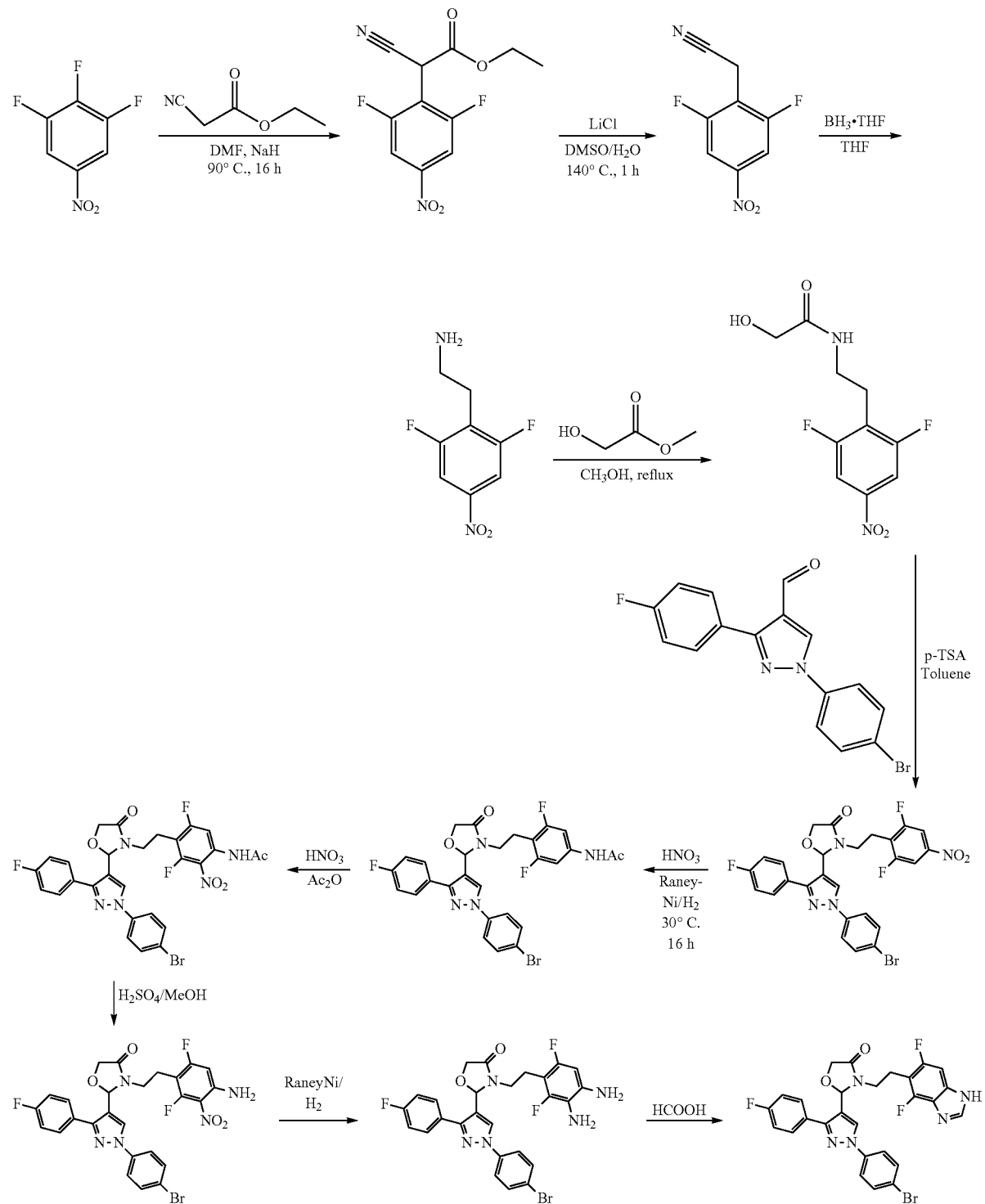

Step 1. ethyl 2-cyano-2-(2,6-difluoro-4-nitrophenyl)acetate

Ethyl cyanoacetate (4.8 g, 42.3 mmol) was dissolved in anhydrous DMF (40 mL), 60% NaH (1.7 g, 42.3 mmol) was added, and the mixture was stirred at room temperature for 1 hour and then 1,2,3-trifluoro-5-nitrobenzene (5 g, 28.2 mmol) was added. They were reacted at 70° C. for 16 hours. After cooling to room temperature, 40 mL of water was added, and the pH was adjusted to 2-3 with 2M hydrochloric acid and the mixture was extracted with ethyl acetate (200 mL). The ethyl acetate solution was washed with saturated saline, dried over anhydrous sodium sulfate, and dried by rotary evaporation to give ethyl 2-cyano-2-(2,6-difluoro-4-nitrophenyl)acetate as a brown oily crude product (8.5 g). This compound was used directly in the next step without purification.

Step 2. 2-(2,6-difluoro-4-nitrophenyl)acetonitrile

Ethyl 2-cyano-2-(2,6-difluoro-4-nitrophenyl)acetate (8.5 g, 31.5 mmol) was dissolved in DMSO (30 mL) and lithium chloride (1.3 g, 31.5 mmol) and 1 mL of water were added. The reaction was carried out for 3 hours at 130 then the mixture was cooled to room temperature, and after adding 100 mL of water it was extracted with ethyl acetate (200 mL). The ethyl acetate solution was washed with saturated saline, dried over anhydrous sodium sulfate, and dried by rotary evaporation. The crude product was isolated by column chromatography (ethyl acetate: methanol=10:1) to give 2-(2,6-difluoro-4-nitrophenyl)acetonitrile as a yellow solid (4.0 g).

Step 3. 2-(2,6-difluoro-4-nitrophenyl)ethanamine 2-(2,6-difluoro-4-nitrophenypacetonitrile (4.0 g, 20.2 mmol) was dissolved in 30 mL of tetrahydrofuran and a solution of borane in tetrahydrofuran (40 mL, 1 M) was added. The mixture was heated to reflux for 3 hours, and then cooled to room temperature. After 10 mL of methanol was slowly added dropwise, the mixture was heated under reflux for 1 hour. The reaction solution was concentrated to obtain crude product of 2-(2,6-difluoro-4-nitrophenyl)ethanamine as a brown oil (4.6 g); MS: 203[M+H]$^+$. This compound was used directly in the next step without purification.

Step 4. N-(2,6-difluoro-4-nitrophenethyl)-2-hydroxyacetamide 2-(2,6-difluoro-4-nitrophenyl)ethanamine (4.6 g, 22.8 mmol) was dissolved in methanol (60 mL), and then methyl 2-hydroxyacetate (10 g, 111 mmol) was added. The mixture was heated at reflux for 40 hours. The reaction solution was concentrated, and the crude product was isolated by column chromatography (dichloromethane: methanol elution=40:1) to give N-(2,6-difluoro-4-nitrophenethyl)-2-hydroxyacetamide as a yellow solid (2.5 g, Yield: 42%); MS: 261 [M+H]$^+$.

Step 5. 2-(1-(4-bromophenyl)-3-(4-fluorophenyl)-1H-pyrazolyl-4yl)-3-(2,6-difluoro-4-nitrophenethyl)oxazoline-4 one N-(2,6-difluoro-4-nitrophenethyl)-2-hydroxyacetamide (2.5 g, 9.6 mmol) and 1-(4-bromophenyl)-3-(4-fluorophenyl)-1H-pyrazol-4-formaldehyde (3.3 g, 9.6 mmol) were dissolved in toluene (60 mL), p-toluenesulfonic acid (825 mg, 4.8 mmol) was added and the mixture was heated to reflux for 16 hours with a water separator. The reaction solution was concentrated, and 50 mL of water was added. The mixture was extracted with ethyl acetate (60 mL). The extracts were respectively washed with 10% sodium bicarbonate solution and saturated saline, dried over anhydrous sodium sulfate, and dried by rotary evaporation. The crude product was separated by column chromatography (dichloromethane: methanol =30: 1) to obtain 2-(1-(4-bromophenyl)-3-(4-fluorophenyl)-1H-pyrazolyl-4-yl)-3-(2,6-difluoro-4-nitrophenethyl)oxazoline-4 one (2.6 g, yield: 46%) as a white solid; MS: 589 [M+H]$^+$.

Step 6. 3-(4-amino-2,6-difluorophenethyl)-2-(1-(4-bromophenyl)-3-(4-fluoro phenyl)-1H-pyrazol-4-yl)oxazoline-4-one 2-(1-(4-bromophenyl)-3-(4-fluorophenyl)-1H-pyrazolyl-4-yl)-3-(2,6-difluoro-4-nitrophenethyl)oxazoline-4-one (2.6 g, 4.4 mmol) was dissolved in ethyl acetate/methanol (1:1, 40 mL), Raney Ni (300 mg) was added and the mixture was hydrogenated at atmospheric pressure. After 2 hours of reaction, the reaction was stopped, the reaction solution was filtered, the filter cake was washed with ethyl acetate, and the filtrate was dried by rotary evaporation to obtain 3-(4-amino-2,6-difluorophenethyl)-2-(1-(4-bromophenyl)-3-(4-fluorophenyl)-1H-pyrazo 1-4-yl)oxazoline-4-one as a white solid (2.3 g, yield: 93%); MS: 559 [M+H]$^+$; This compound was used directly in the next step without purification.

Step 7. 3-(2,6-difluoro-5-nitro-4-acetamidophenethyl)-2-(3-(4-fluorophenyl)-1-(4-bromophenyl)-1H-pyrazol-4-yl)oxazolidin-4-one 3-(4-amino-2,6-difluorophenethyl)-2-(1-(4-bromophenyl)-3-(4-fluorophenyl)-1H-pyrazol-4-yl)oxazoline-4-one (1.8 g, 3.2 mmol) was dissolved in 20 mL of dichloromethane, 1 mL of acetic anhydride was added, and the reaction was stirred at room temperature for 2 hours. The reaction solution was concentrated, and diethyl ether (20 mL) was added to the residue. The mixture was filtered to give 3-(2,6-difluoro-4-acetamidophenethyl-2-(3-(4-fluorophenyl)-1-(4-bromophenyl)-1H-pyrazol-4-yl)oxazolidin-4-one as a white solid (1.8 g, 93% yield); MS: 601 [M+H]$^+$.

Step 8. 3-(2,6-difluoro-5-nitro-4-acetamidophenethyl)-2-(3-(4-fluorophenyl)-1-(4-bromophenyl)-1H-pyrazol-4-yl)oxazolidin-4-one 3-(2,6-difluoro-4-acetamidophenethyl)-2-(3-(4-fluorophenyl)-1-(4-bromophenyl)-1H-pyrazol-4-yl)oxazolidin.-4-one (1.8 g, 3 mmol) was dissolved in 20 mL of concentrated sulfuric acid, potassium nitrate (455 mg, 4.5 mmol) was added at 0° C., and then the mixture was returned to room temperature. The reaction was stirred for 2 hours. The reaction was poured into crashed ice and extracted with ethyl acetate (60 mL). The extracts were respectively washed with 10% sodium bicarbonate solution and saturated saline, dried over anhydrous sodium sulfate, and dried by rotary evaporation. The crude product was separated by column chromatography (dichloromethane: methanol=40:1) to obtain 3-(2,6-difluoro-5-nitro-4-acetamidophenethyl)-2-(3-(4-fluorophenyl)-1-(4-bromophenyl)-1H-pyrazol-4-yl)oxazolidin-4-one as a pale yellow solid (800 mg, yield: 41%); MS: 646 1M+H]$^+$.

Step 9. 3-(4-amino-2,6-difluoro-3-nitrophenethyl)-2-(1-(4-bromophenyl)-3-(4 fluorophenyl)-1H-pyrazol-4-yl)oxazoline-4-one 3-(2,6-difluoro-5-nitro-4-acetamidophenethyl)-2-(3-(4-fluorophenyl)-1-(4-bromophenyl)-1H-pyrazol-4-yl)oxazolidin-4-one (800 mg, 1.24 mmol) was dissolved in 10 mL of methanol, 0.5 mL of concentrated sulfuric acid was added, and the mixture was heated under reflux for 2 hours and concentrated under reduced pressure. Water (20 mL) was added to the residue and the mixture was extracted with ethyl acetate (40 mL). The extracts were respectively washed with 10% sodium bicarbonate solution and saturated saline, dried over anhydrous sodium sulfate, and dried by rotary evaporation. The crude product was isolated by column chromatography (dichloromethane: methanol=30:1) to obtain 3-(4-amino-2,6-difluoro-3-nitrophenethyl)-2- (1-(4-bromophenyl)-3-(4 fluorophenyl)-1H-pyrazol-4-yl)oxazoline-4-one (520 mg, yield: 69%) as a yellow solid; MS: 604 [M+H]$^+$.

Step 10. 2-(1-(4-bromophenyl)-3-(4-fluorophenyl) 1H-pyrazol-4-yl)-3-(3,4-diamino-2,6-difluorophenethyl)oxazoline-4-one 3-(4-Amino-2,6-difluoro-3-nitrophenethyl)-2-(1-(4-bromophenyl)-3-(4-fluorophenyl)-1H-pyrazol-4-yl)oxazoline-4-one (480 mg, 0.8 mmol) was dissolved in 5 mL of ethyl acetate and 5 mL of methanol, Raney Ni (20 mg) was added and the mixture was hydrogenated at atmospheric pressure. After 1 hour of reaction, the reaction was stopped, the reaction solution was filtered, and the filter cake was washed with a solution of ethyl acetate/ethanol (1:1). The filtrate was dried by rotary evaporation to give 2-(1-(4-bromophenyl)-3-(4-fluorophenyl)-1H-pyrazol-4-yl)-3-(3,4-diamino-2,6-difluoro phenethyl)oxazoline-4-one as a brown solid (450 mg, yield: 98%), which was used directly in the next reaction without purification; MS: 574 [M+H]$^+$.

Step 11. 2-(1-(4-bromophenyl)-3-(4-fluorophenyl) I H-pyrazol-4-yl)-3-(2-(5,7-difluoro-1H)-benzo[d]imidazol-6-yl)ethyl)oxazoline-4-one 2-(1-(4-bromophenyl)-3-(4-fluorophenyl)1H-pyrazol-4-yl)-3-(3,4-diamino-2,6-difluorophenethyl)oxazoline-4-one (190 mg, 0.33 mmol) was dissolved in 5 mL of formic acid. The reaction was stirred at 70° C. for 1 hour, concentrated to dry, and the crude product was isolated by reverse phase column chromatography to give 2-(1-(4-bromophenyl)-3-(4-fluorophenyl)-1H-pyrazol-4-yl)-3 i fluoro-1H-benzo[d]imidazol-6-yl)ethyl)oxazoline-4-one (88 mg, Yield: 45.8%).

$^1$H NMR (400 MHz, DMSO-d$_6$) δ 8.82 (s, 1H); 8.33 (s, 1H); 7.90 (d, J=8.4 Hz, 2H); 7.73 (d, J=8.4 Hz, 2H); 7.62-7.66 (m, 2H); 7.26-7.30 (m, 2H); 7.19 (d, J=9.6 Hz, 1H); 6.19 (s, 1H); 4.19-4.31 (m, 2H); 3.66-3.69 (m, 1H); 2.79-2.98 (m, 3H); MS: 584 [M+H]$^+$.

EXAMPLE 11

2-(1-(4-bromophenyl)-3-(4-fluorophenyl)1H-pyrazol-4-yl)-3-(2-(4,6-difluoro-2-carbonyl-2,3-dihydro-1H-benzo[d]imidazol-5-yl)ethyl)oxazoline-4-one

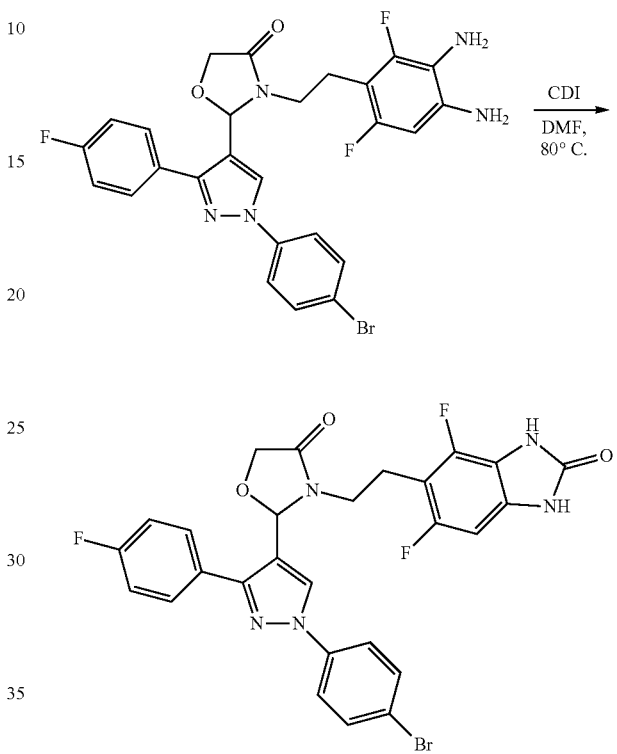

2-(1-(4-bromophenyl)-3-(4-fluorophenyl)1H-pyrazol-4-yl)-3-(3,4-diamino-2,6-difluorophenethyl)oxazoline-4-one (260 mg, 0.45 mmol) was dissolved in 8 mL of dry DMF, and CDI (88 mg, 0.54 mmol) was added. The reaction solution was stirred at 80° C. for 16 hours, cooled to room temperature, then 30 mL of water was added, and the mixture was extracted with ethyl acetate (30 mL×2). The extract was washed with a saturated sodium chloride solution, dried over anhydrous sodium sulfate, and concentrated to give a crude product, which was purified by column chromatography (dichloromethane: methanol 30:1) to give 2-(1-(4-bromophenyl)-3-(4-fluorophenyl)1H-pyrazol-4-yl)-3-(2-(4,6-difluoro-2-carbonyl-2,3-dihydro-1H-benzo[d]imidazol-5-yl)ethyl)oxazoline-4-one (160 mg), which was washed with dichloromethane to give the product as a white solid (120 mg, yield: 44%).

$^1$H NMR (400 MHz. DMSO-d$_6$) δ 10.93-11.03 (m, 2H); 8.83 (s, 1H); 7.91 (d, J=6.8 Hz, 2H); 7.65-7.74 (m, 4H); 7.26-7.32(m,2H); 6.57(d, J=8.8 Hz,1H); 6.16(s,1H); 4.21-4.32(m,2H); 3.61-3.64(m,1H); 2.91-2.94 (m, 1H); 2.67-2.74 (m, 2H); MS: 600 [M+]$^+$.

EXAMPLE 12

2-(1-(4-bromophenyl)-3-(4-fluorophenyl)-1H-pyrazol-4-yl)-3-(2-(5,7-difluoro-1H hydrogen-benzor[d][1,2,3]triazol-6-yl)ethyl)oxazoline-4-one

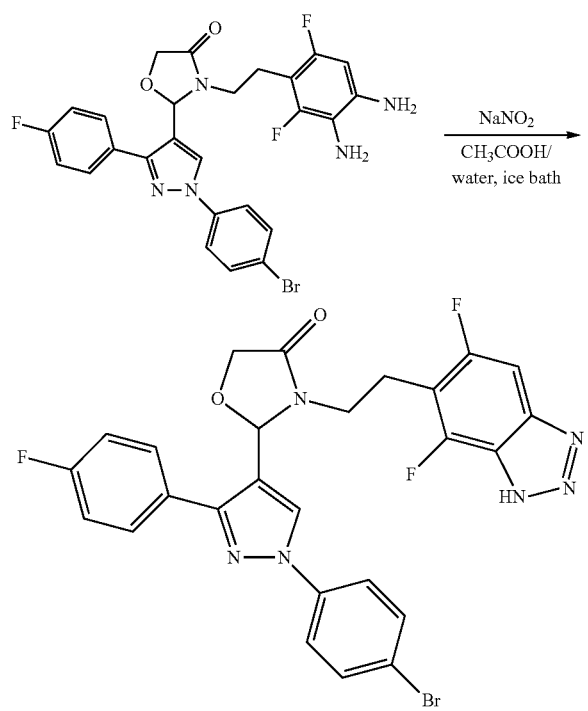

2-(1-(4-bromophenyl)-3-(4-fluorophenyl)1H-pyrazol-4-yl)-3-(3,4-diamino-2,6-difluorophenethyl)oxazoline-4-one (130 mg, 0.23 mmol) was dissolved in glacial acetic acid (5 ml)/water (3 ml), and sodium nitrite (32 mg, 0.46 mmol) was dissolved in 2 ml of water and then added into the reaction liquid under cooling in an ice bath. TLC (dichloromethane:methanol=15:1) showed that the raw material was consumed after half an hour. The reaction solution was poured into 100 ml of ice water, adjusted to basic with saturated sodium bicarbonate, and extracted twice with ethyl acetate (50 ml×2). The collected organic phases were washed three times with brine, dried over anhydrous sodium sulfate, filtered, concentrated by rotary evaporation. The residue was dissolved in DMF and subjected to HPLC purification to give a white solid (65 mg, yield: 40%).

$^1$H NMR (400 MHz, DMSO-$d_6$) δ 8.84 (s, 1H), 7.90 (d, J=8.8 Hz, 2H), 7.73 (d, J=8.0 Hz, 2H), 7.66 (t, J=6.4 Hz, 2H), 7.48 (d, J=8.4 Hz, 1H), 7.29 (t, J=8.4 Hz, 2H), 6.23 (s, 1H), 4.32-4.20 (m, 2H), 3.71-3.68 (m, 1H), 3.05-3.02 (m, 1H), 2.90-2.84 (m, 2H); MS: 583.1 [M+H]$^+$.

EXAMPLE 13

2-(1-(4-bromophenyl)-3-(4,6-difluorophenyl)-1H-pyrazol-4-yl)-3-(2-(2-oxo-dihydroindol-5-yl)ethyl)oxazoline-4-one

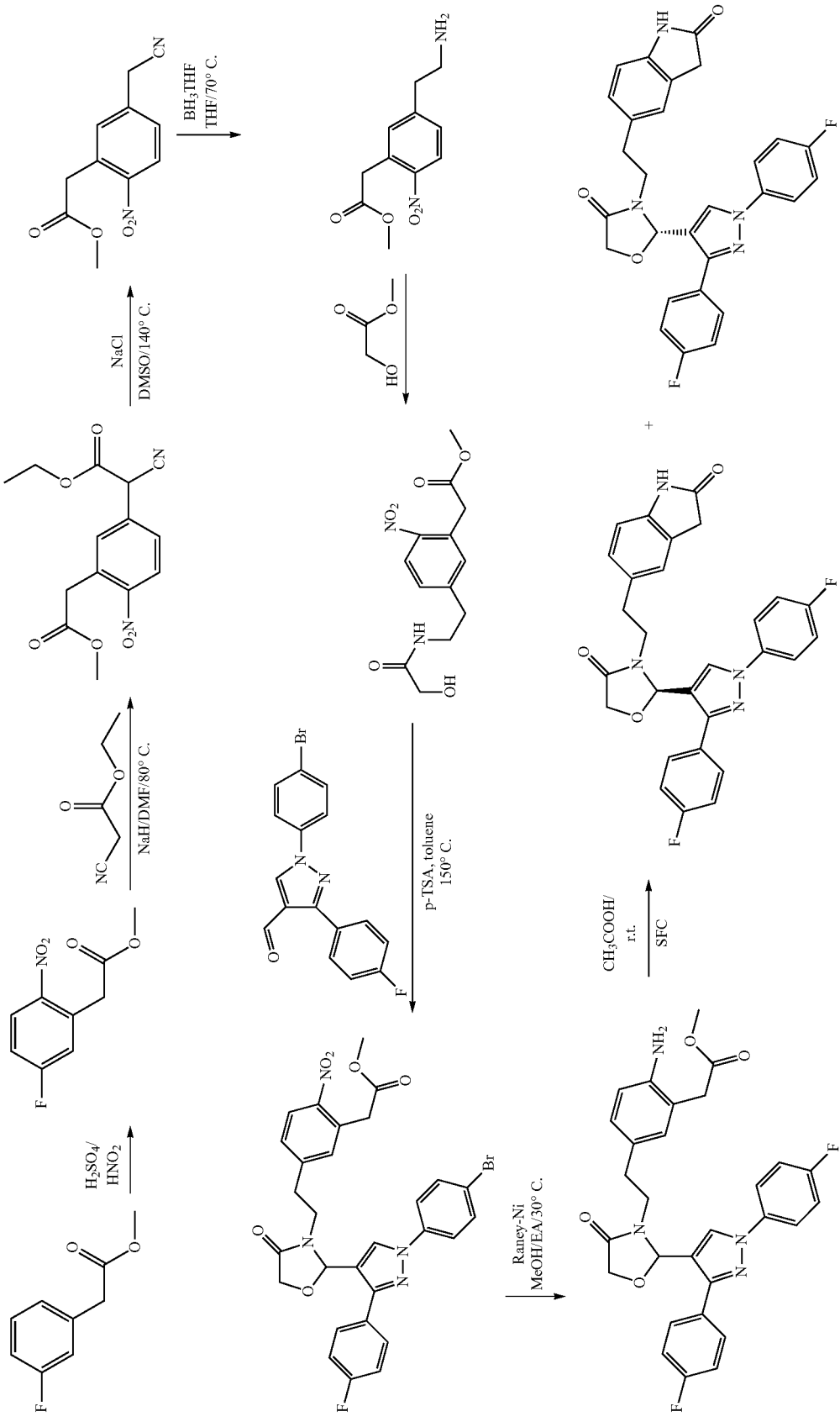

Step 1. methyl 2-(5-fluoro-2-nitrophenyl)formate

Concentrated sulfuric acid (16.0 g) was slowly added to methyl 2-(3-fluorophenyl)acetate (16.0 g, 95.23 mmol) under cooling in an ice bath, and nitric acid (12.0 ml) was slowly added dropwise half an hour later. After addition, the mixture was stirred for 2 hours, and then the reaction solution was slowly poured into ice water, extracted with ethyl acetate, and the organic phase was concentrated to dry to give a white solid (10.6 g, yield: 52%).
$^1$H NMR (400 MHz, CDCl$_3$) δ 8.22-8.19 (m, 1H); 7.18-7.16 (m, 1H); 7.14-7.06 (m, 1H); 4.03 (s, 2H); 3.73 (s, 3H).

Step 2. methyl 2-(2-nitrophenyl) cyanofomate

Ethyl cyanoacetate (5.3 g, 46.9 mmol) was dissolved in anhydrous DMF (50 ml) and NaH (60%) (1.9 g, 46.9 mmol) was added and the mixture was stirred at room temperature for 1 hour. Methyl-2-(5-fluoro-2-nitrophenyl)formate (5 g, 28.2 mmol) was added and the reaction was carried out at 80° C. for 16 hours. After the mixture was cooled to room temperature, water was added and the pH was adjusted with hydrochloric acid (2 M) to 3. The mixture was extracted with ethyl acetate, and dried by rotary evaporation to give a crude product, which went through column to give the product as a brown oil (6.7 g, yield: 93%); MS: 305 [M–H]$^+$.

Step 3. methyl 2-(5-(cyanomethyl)-2-nitrophenyl)formate

Methyl 2-(2-nitrophenyl)cyanoformate (1.0 g, 3.26 mmol) was dissolved in DMSO (10 mL) and sodium chloride (0.57 g, 9.80 mmol) and 0.05 mL of water were added. After reacting for 1.5 hours at 140° C., the mixture was cooled to room temperature, added with water, and extracted with ethyl acetate. The extract was dried by rotary evaporation, and the crude product was separated by column chromatography (dichloromethane/methanol elution=30:1) to give the desired product as a red oil (700 mg, Yield: 76%).

Step 4. methyl 2-(5-(2-aminoethyl)-2-nitrophenyl)formate

Methyl 2-(5-(cyanomethyl)-2-nitrophenyl)formate (0.7 g, 2.99 mmol) was dissolved in tetrahydrofuran (5 ml) and a solution of borane in tetrahydrofuran (3.29 ml, 1M) was added. The mixture was heated to reflux for 2 hours, cooled to room temperature, 10 ml of methanol was slowly added dropwise, and the reaction solution was concentrated to give the target product as a red-brown solid (638 mg, yield: 87%); MS: 238 [M+H]$^+$.

Step 5. methyl 5-(2-(2-hydroxyacetamide)ethyl)-2-nitrobenzoate

Methyl 2-(5-(2-aminoethyl)-2-nitrophenyl)formate (638 mg, 2.68 mmol) was dissolved in methanol (10 ml) and methyl 2-hydroxyacetate (2.68 g, 8.04 mmol) was added. The mixture was heated to reflux for 40 hours, the reaction solution was concentrated and the crude product was isolated by column chromatography (eluted with dichloromethane/methanol =40: 1) to give the target product as a red oil (100 mg, yield: 12.6%). MS: 296[M+H]$^+$.

Step 6. methyl 2-(5-(2-(2-(1-(4-bromophenyl)-3-(4-fluorophenyl)-1H-pyrazol-4-yl)-4-oxooxazolidin-3-yl)methyl)-2-nitrophenyl)formate Methyl 5-(2-(2-hydroxyacetamide)ethyl)-2-nitrobenzoate (100 mg, 0.34 mmol) and 1-(4-bromophenyl)-3-(4-fluorophenyl))-1H-pyrazol-4-formaldehyde (116 mg, 0.34 mmol) were dissolved in toluene (13 ml) and p-toluenesulfonic acid (32.1 mg, 0.17 mmol) was added. The mixture was heated to reflux at 150° C. for 16 hours with a water separator. The reaction solution was concentrated, added with water, extracted with ethyl acetate (60 ml), washed with 10% sodium bicarbonate solution, dried over anhydrous sodium sulfate, and dried by rotary evaporation. The crude product was prepared in liquid phase to give the target product as a brown solid (60 mg, yield: 28%); MS: 623 [M+H]$^+$.

Step 7. methyl 2-(5-(2-(1-(4-bromophenyl)-3-(4-fluorophenyl)-1H-pyrazol-4-yl)-4-oxooxazolidin-3-yl)methyl)-2-aminophenyl)formate Methyl 2-(5-(2-(2-(1-(4-bromophenyl)-3-(4-fluorophenyl)-1H-pyrazol-4-yl)-4-oxooxazolidin-3-yl)methyl)-2-nitrophenyl) methyl formate was dissolved in ethyl acetate/methanol (1:1) (6 ml), Raney Ni (6 mg) was added and the mixture was hydrogenated at atmospheric pressure. After reacting for 16 hours, the reaction was stopped, the reaction solution was filtered, the filter cake was washed with ethyl acetate, and the filtrate was dried by rotary evaporation to give the target product as a yellow solid (58 mg, yield: 97%). This compound was directly used in the next reaction without purification; MS: 593 [M+H]$^+$.

Step 8. 2-(1-(4-bromophenyl)-3-(4-fluorophenyl) 1H-pyrazol-4-yl)-3-(2-(2-oxoindolin-5-yl)ethyl)oxazoline-4-one Methyl 2-(5-(2-(2-(1-(4-bromophenyl)-3-(4-fluorophenyl)-1H-pyrazol-4-yl)-4-oxooxazolidin-3-yl)methyl)-2-aminophenyl) methyl formate (58 mg, 0.1 mmol) was dissolved in 2 mL of glacial acetic acid and the reaction was stirred at room temperature for 16 hours. The reaction solution was concentrated to give a crude solid, which was prepared through HPLC to give a product as a pale yellow solid (8 mg, yield: 15%).
$^1$H NMR (400 MHz, DMSO-d$_6$) δ 10.24 (s, 1H); 8.73 (s, 1H); 7.91-7.89 (d, J=8.4 Hz, 2H); 7.73-7.71 (m, 2H); 7.67-7.64(m,4H); 7.32-7.28(t,J=8.8 and 8.0 Hz,2H); 6.86-6.82(m,2H); 6.62-6.60(d,J=7.6 Hz,1H); 6.02 (s, 1H); 4.26 (m, 2H); 3.69-3.66 (m, 1H); 3.18 (s, 2H); 2.92 (m, 1H); 2.66 (m, 2H); MS: 561 [M+H]$^+$.

2-(1-(4-bromophenyl)-3-(4,6-difluorophenyl)-1H-pyrazol-4-yl)-3-(2-(2-oxoindolin-5-yl)ethyl)oxazoline-4-one (18 g) was chrial separated via SFC (column: OJ-H; column size: 0.46 cm I.D.×15 cm L; injection volume: 2.0 μl; mobile phase: HEP/EtOH=60/40/(V/V); flow rate: 0.5 mL/min; wavelength: UV 254 nm; temperature: 25° C.) to give two optical isomers.

(S)-2-(1-(4-bromophenyl)-3-(4,6-difluorophenyl)-1H-pyrazol-4-yl)-3-(2-(2-oxoindolin-5-yl)ethyl)oxazoline-4-one, white solid, 6.46 g, 35.9% yield. $t_R$ 2.629 min, $[α]_D$– 22.77° (c 0.5007 g/100 mL, 18.4 (V); purity: 98.39%, ee: 100.0%.

(R)-2-(1-(4-bromophenyl)-3-(4,6-difluorophenyl)-1H-pyrazol-4-yl)-3-(2-(2-oxoindolin-5-yl)ethyl)oxazoline-4-one, white solid, 6.63 g, 36.8% yield. $t_R$ 7.951 min, $[α]_D$+ 23.08° (c 0.5113 g/100 mL, 19.2° C.); purity: 99.10%, cc,: 100.00%.

EXAMPLE 14

2-(1-(4-bromophenyl)-3-(4-difluorophenyl)-1H-pyrazole)-3-(2-(3,3-difluoro-2-oxoindolin-5-ethypoxoindolin-4-one

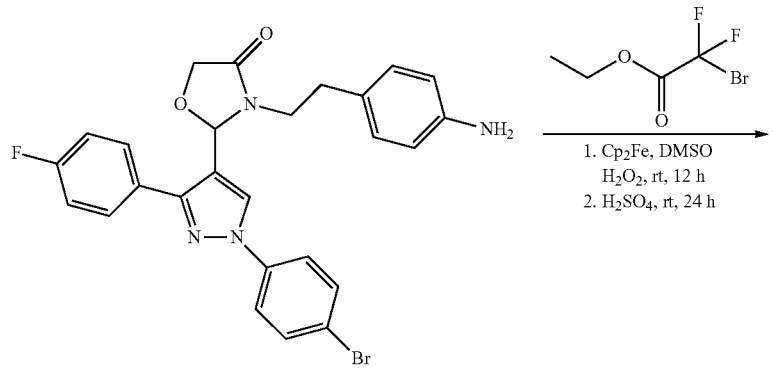

2-(1-(4-bromophenyl)-3-(4-fluorophenyl)-1H-pyrazol-4-yl)-3-(3,4-diaminophenethyl)oxazoline-4 one compound (521 mg, 1.0 mmol), ethyl 2-bromo-2,2-difluoroacetate (0.388 mL, 3.0 mmol), Cp$_2$Fe (19 mg, 0.1 mmol) were dissolved in 5 mL of DMSO. Under nitrogen protection, the reaction was stirred at room temperature for 12 hours, then 2 mL of 1M concentrated sulfuric acid in DMSO was added and the reaction was continued for 24 hours under nitrogen protection. After the reaction was completed, the reaction mixture was poured into ice water and extracted with ethyl acetate. The extract was extracted with saturated saline solution and dried over anhydrous sodium sulfate, concentrated to dry, and the crude product was isolated by preparative HPLC to give a white solid (10 mg, yield: 1.6%).

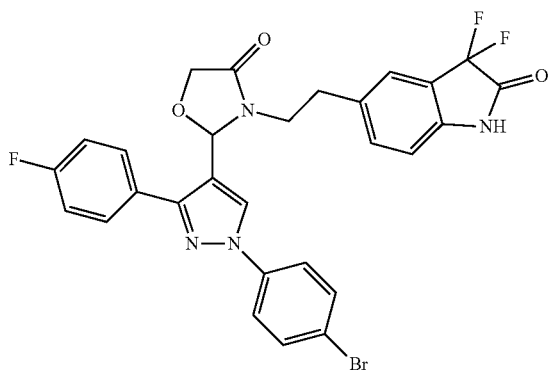

$^1$NMR (400 MHz, DMSO-d$_6$) δ 11.03 (s, 1H), 8.72 (s, 1H), 7.90 (d, J=8.8 Hz, 2H), 7.73-7.65 (m, 4H), 7.35-7.20 (m, 4H), 6.78 (d, J=8.0 Hz, 1H), 6.07 (s, 1H), 4.27-4.24 (m, 2H), 3.74-3.70 (m, 1H), 3.02-2.95 (m, 1H), 2.73-2.64 (m, 2H); MS: 597 [M+H]$^+$.

EXAMPLE 15

3-(2-(2-oxo-2,3-dihydro-1H-benzo[d]imidazol-5-yl)ethyl)-2-(1-(4-fluorophenyl)-3-(4-fluorophenyl)-1H-pyrazol-4-yl)-oxazolidin-4-one

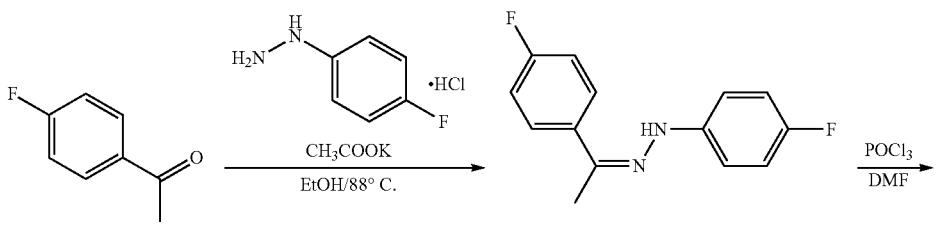

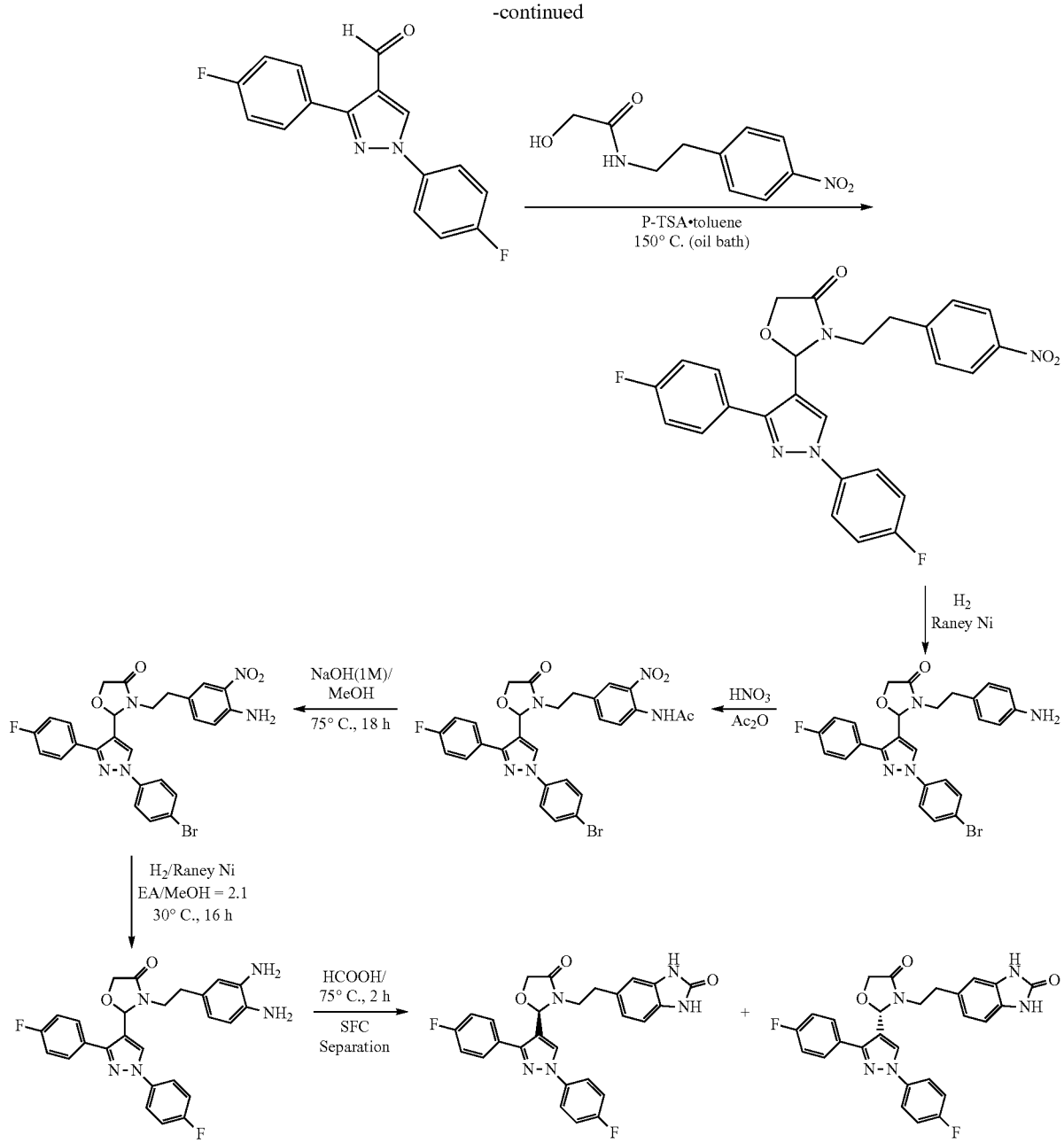

Step 1. 1-(4-fluorophenyl)-2-(1-(4-fluorophenyl) ethylidene) hydrazine 1-(4-Fluorophenyl)ethanone (17.0 g, 123 mmol), 1-(4-fluorophenyl)hydrazine hydrochloride (20.0 g, 123 mmol) and potassium acetate (12.0 g, 123 mmol) were added to ethanol (200 mL) and the mixture was stirred at 88° C. overnight. The reaction mixture was concentrated in vacuo to dry and dissolved in dichloromethane, which was filtered to give a crude product, which was washed with petroleum ether to give 1-(4-fluorophenyl)-2-(1-(4-fluorophenyl)ethylidene) hydrazine (26.0 g, 105 mmol, yield: 85%).

$^1$H NMR (400 MHz, DMSO-$d_6$) δ 9.25 (s, 2H); 7.82-7.80 (m, 2H); 7.23-7.18 (m, 4H); 7.08-7.04 (m, 2H); 2.24 (s, 3H).

Step 2. 1-(4-fluorophenyl)-3-(4-fluorophenyl)-1H-pyrazol-4-formaldehyde

Phosphorus oxychloride (13.5 mL, 142 mmol) was slowly added dropwise to anhydrous DMF (11 mL, 142 mmol) under cooling in ice bath, and after stirring for 30 min, a solution of 1-(4-fluorophenyl)-2-(1-(4-fluorophenyl)ethylidene)hydrazine (20.0 g, 81.2 mmol) in 25 mL of anhydrous DMF was slowly added dropwise to the reaction solution, and the mixture was stiffed at room temperature for 1 hour, then the temperature was raised to 70° C., and the reaction was continued for 5 hours, and the reaction solution was poured into ice water, and filtered. The solid was slurried with acetone, and filtered to give the product as a white solid (18 g, 63.4 mmol, yield: 78%).

Step 3. 2-(1-(4-fluorophenyl)-3-(4-fluorophenyl)-4-1H-pyrazolyl)-3-(4-nitrophenethyl)oxazoline-4-one 1-(4-fluorophenyl)-3-(4-fluorophenyl)-1H-pyrazol-4-formaldehyde (9.65 g, 33.9 mmol), 2-hydroxy-N-(4-nitrophenethyl)acetamide (9.14 g, 40.8 mmol) and p-toluenesulfonic acid monohydrate (3.23 g, 16.9 mmol) were dissolved in 250 mL of toluene. The mixture was heated under reflux with a water separator for 16 hours. The mixture was extracted with ethyl acetate, and dried by rotary evaporation. The crude product was dispersed in water, and filtered after stirring for 15 minutes. The filter cake was dispersed in methanol, filtered after stirring for 30 minutes. The solvent was dried by rotary evaporation to give 2-(1-(4-fluorophenyl)-3-(4-fluorophenyl)-4-1H-pyrazolyl)-3-(4-nitrophenethyl)oxazoline-4-one (13.3 g, 27.1 mmol, yield: 80%).

Step 4. 3-(4-aminophenethyl)-2-(1-(4-fluorophenyl)-3-(4-fluorophenyl)-4-1H-pyrazolyl)oxazoline-4-one 2-(1-(4-fluorophenyl)-3-(4-fluorophenyl)-4-1H-pyrazolyl)-3-(4-nitrophenethyl)oxazoline-4-one (13.3 g, 27.1 mmol) was dissolved in ethyl acetate/methanol (1:1, 300 mL), Raney Ni (2.6 g) was added, hydrogen gas was introduced, and the mixture was stirred at 50° C. for 16 hours, and then filtered. The filtrate was concentrated to give 3-(4-aminophenethyl)-2-(1-(4-fluorophenyl)-3-(4-fluorophenyl)-4-1H-pyrazolyl)oxazoline-4-one (12 g, 26.2 mmol, yield: 97%).

$^1$H NMR (400 MHz, DMSO-$d_6$) δ 8.71 (s, 1H); 8.00 (m, 2H); 7.69 (m, 2H); 7.42 (t, 2H); 7.36 (t, 2H); 6.73 (d, 2H); 6.45 (d, 2H); 6.13 (s, 1H); 4.92 (s, 2H)); 4.28 (dd, 2H, J=13 and 21 Hz); 3.65 (m, 1H); 2.87 (m, 1H); 2.62-2.42 (m, 2H).

Step 5. N-(4-(2-(2-(1-(4-fluorophenyl)-3-(4-fluorophenyl)-4-1H-pyrazol yl)-4-oxazoline-3-yl)ethyl)-2-nitrophenyl)acetamide 3-(4-aminophenethyl)-24 I -(4-fluorophenyl)-3-(4-fluorophenyl)-4-1H-pyrazolyl)oxazoline-4-one (12.0 g, 26 mmol) was dissolved in Ac$_2$O (100 mL) and the mixture was stirred at room temperature for 60 min. After completion of the reaction, the reaction mixture was cooled to 0° C. and then HNO$_3$ (65%, 2.7 mL) was slowly added to the reaction mixture. The reaction mixture was stirred at room temperature overnight. TLC (petroleum ether: ethyl acetate=1:2) showed that the reaction was almost complete. The reaction mixture was concentrated in vacuo to dry, and the crude product was recrystallized from ethyl acetate and filtered to give a white solid (12.0 g, 21.9 mmol, yield: 73%).

Step 6. 3-(4-amino-3-nitrophenethyl)-2-(1-(4-fluorophenyl)-3-(4-fluorophenyl)-1H-pyrazolyl-4 yl)oxazoline-4-one N-(4-(2-(2-(1-(4-fluorophenyl)-3-(4-fluorophenyl)-4-1H-pyrazolyl)-4-oxazoline-3-yl)ethyl)-2-nitrophenypacetamide (12.0 g, 22 mmol) was dissolved in methanol (300 mL), NaOH (1N, 40 mL) and the mixture was refluxed overnight. Ethyl acetate was added to the reaction solution and the mixture was partitioned. The ethyl acetate phase was washed with saturated saline, dried over anhydrous sodium sulfate, filtered and the filtrate was concentrated in vacuo to give a crude product of 3-(4-amino-3-nitrophenethyl)-2-(1-(4-fluorophenyl)-3-(4-fluorophenyl)-1H-pyrazolyl-4-yl)oxazoline-4-one (10.0 g, 19.8 mmol, yield: 90%) which was used directly in the next reaction.

Step 7. 2-(1-(4-fluorophenyl)-3-(4-fluorophenyl)-1H-pyrazol-4-yl)-3-(3,4-diaminophenethyl)oxazoline-4-one Crude 3-(4-amino-3-nitrophenethyl)-2-(1-(4-fluorophenyl)-3-(4-fluorophenyl)-1H-pyrazolyl-4-yl)oxazoline-4-one (10.0 g, 19.8 mmol) was dissolved in ethyl acetate/methanol (1:1, 400 mL), Raney Ni (2.0 g) was added, hydrogen gas was introduced, and the mixture was stirred at 50° C. for 16 hours, and then filtered. The filtrate was concentrated to give crude 3-(4-aminophenethyl)-2-(1-(4-fluorophenyl)-3-(4-fluorophenyl)-4-1H-pyrazolyl)oxazoline-4-one (9.0 g, 18.9 mmol, yield: 95%) which was used directly in the next reaction.

Step 8. 2-(1-(4-fluorophenyl)-3-(4-fluorophenyl)1 H-pyrazol-4-yl)-3-(2-(6-fluoro-2-carbonyl-2,3-dihydro-1H-benzo[d]imidazol-5-yl)ethyl)oxazoline-4-one Crude 2-(1-(4-fluorophenyl)-3-(4-fluorophenyl)-1H-pyrazol-4-yl)-3-(3,4-diaminophenethyl)oxazoline-4-one (9.0 g, 18.9 mmol) and CDI (3.8 g, 23.4 mmol) were dissolved in anhydrous DMF (10 mL) and the mixture was stirred under nitrogen protection at 60° C. for 4 hours. After the reaction was completed, the reaction solution was poured into water (300 mL) and extracted with ethyl acetate (300 mL×3). The collected organic phases were washed once with saturated saline, dried over anhydrous sodium sulfate, filtered, and the filtrate was dried by rotary evaporation to give a crude product (6.0 g) which was washed with dichloromethane and filtered. The solid was dried in vacuo to give 2-(1-(4-bromophenyl)-3-(4-fluorophenyl)1H-pyrazol-4-yl)-3-(2-(6-fluoro-2-carbonyl-2,3-dihydro-1H-benzo[d]imidazol-5-yl)ethyl)oxazoline-4-one (3.0 g, 6.0 mmol, 32%: yield).

$^1$H NMR (400 MHz, DMSO-$d_6$) δ 10.44 (s, 2H)), 8.65 (s, 1H), 7.96-7.92 (m, 2H), 7.64-7.61 (m, 2H), 7.37 (t, J=8.4 Hz, 2H), 7.28 (t, J=8.8 Hz, 2H), 6.73-6.59 (m, 3H), 6.02 (s, 1H), 4.26-4.23 (m, 2H), 3.67-3.63 (m, 1H), 2.91-2.88 (m, 1H), 2.68-2.62 (m, 2H); MS: 502.2 [M+H]$^+$.

3-(2-(2—Oxo-2,3-dihydro-1H-benzo[d]imidazol-5-yl)ethyl)-2-(1-(4-fluorophenyl)-3-(4-fluorophenyl)-1H-pyrazol-4-yl)-oxazolidin-4-one (3 g) was chrial separated via SFC (column: OJ-H; column size: 0.46 cm I.D.×15 cm L; Injection volume: 2.0 μl; Mobile phase: HEP/EtOH=60/40 (VN); Flow rate: 0.5 mUmin; Wavelength: UV 254 nm; Temperature: 25° C.) to give two optical isomers.

(S)-3-(2-(2-oxo-2,3-dihydro-1H-benzo[d]imidazol-5-yl)ethyl)-2-(1-(4-fluorophenyl)-3-(4-fluorophenyl)-1H-pyrazol-4-yl)-oxazolidin-4-one, white solid, 1.00 g, yield 33.3%. $t_R$ 1.831 min, $[α]_D$ −12.30° (c 0.5040 g/100 mL, 14.7° C.); purity: 99.52%, ee: 100.0%.

(R)-3-(2-(2-oxo-2,3-dihydro-1H-benzo[d]imidazol-5-yl)ethyl)-2-(1-(4-fluorophenyl)-3-(4-fluorophenyl)-1H-pyrazol-4-yl)-oxazolidin-4-one, white solid, 0.88 g, yield 29.3%. $t_R$ 2.275 min, $[α]_D$ +14.80° (c 0.5001 g/100 mL, 14.1° C.); purity: 99.45%, ee: 99.54%.

EXAMPLE 16
6-(2-{2-[1-(4-bromo-phenyl)-3-(4-fluoro-phenyl)-1-hydro-pyrazol-4-yl]-4-carbonyl-oxazoline-3-yl}-ethyl)-3-hydro-2-carbonyl-benzoxazole
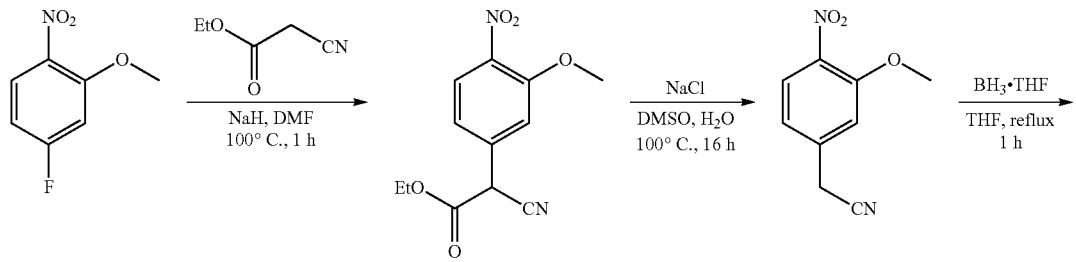
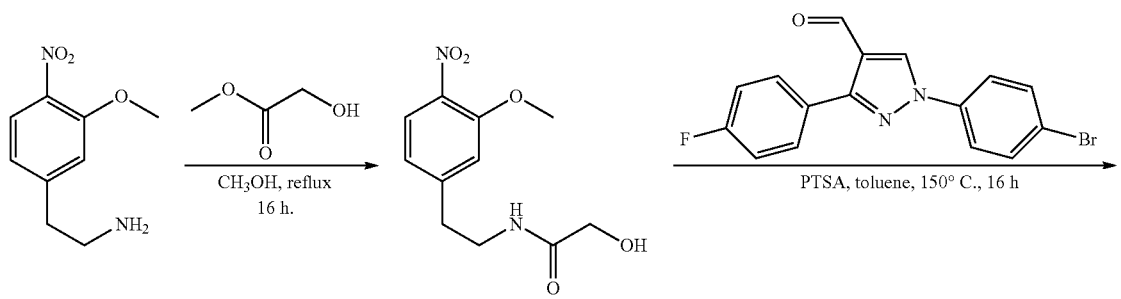
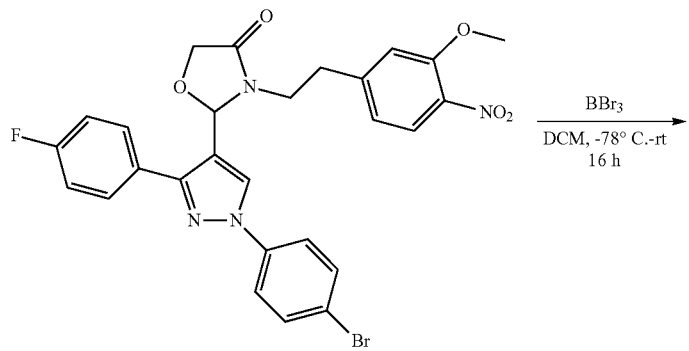
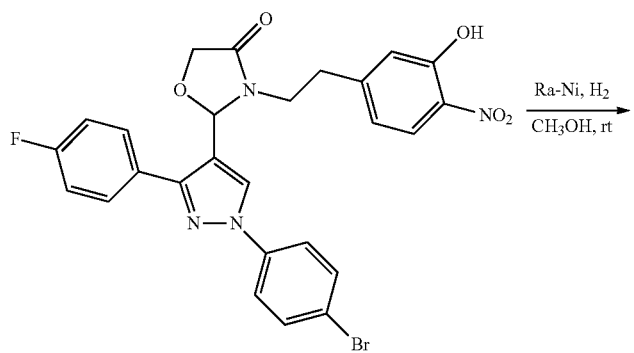

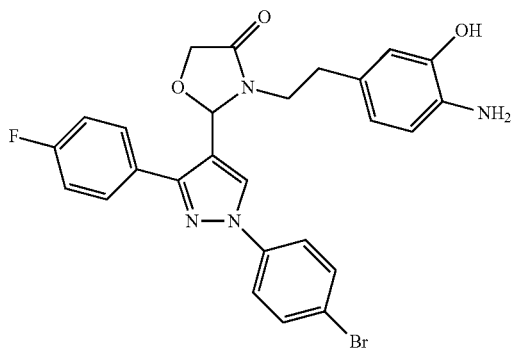 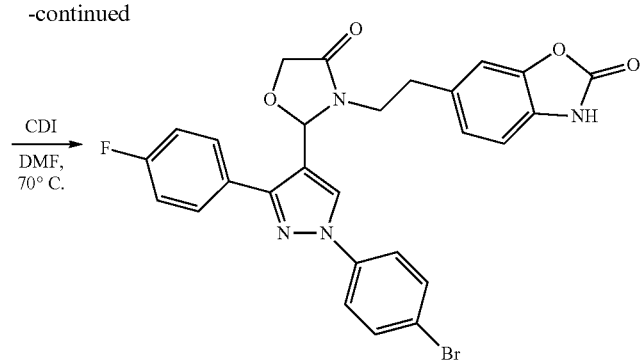

Step 1. Ethyl (3-methoxy-4-nitro-phenyl)-cyanoacetate

Ethyl cyanoacetate (3.6 g, 32.1 mmol) was dissolved in DMF (50 mL), then sodium hydride (0.9 g, 60% in mineral oil, 37.9 mmol) was gradually added at room temperature, and after addition, the mixture was stirred for half an hour, and then. 3-methoxy-4-nitro-fluorobenzene (5.0 g, 29.2 mmol) was added. The reaction was heated to 100 and stirred for one hour. TLC (petroleum ether: ethyl acetate=10:1) showed that the starting material was consumed. The reaction solution was quenched with 300 mL of ice-aqueous saturated ammonium chloride, then dilute hydrochloric acid was added until the reddish-brown color faded, and extracted twice with ethyl acetate (100 mL×2). The collected organic phases were washed three times with saturated saline and dried over anhydrous sodium sulfate, and filtered, and the filtrate was concentrated to give a crude brown oil (9.0 g, 100%), which was used directly in the next reaction.

Step 2. (3-methoxy-4-nitro-phenyl)-acetonitrile

Ethyl (3-methoxy-4-nitro-phenyl)-cyanoacetate (9.0 g, 0.034 mol), sodium chloride (3.37 g, 0.058 mol), and water (0.54 ml, 0.03 mol) were dissolved in DMSO (90 mL), and heated to 100° C. overnight. TLC showed that the starting material was consumed. The reaction mixture was diluted with 500 mL of water and extracted twice with ethyl acetate (100 mL×2). The collected organic phases were washed three times with saturated saline, dried over anhydrous sodium sulfate, filtered, and the filtrate was concentrated. The crude product was purified by silica gel column to give a red-brown solid (2.6 g, 40%).

Step 3. (3-methoxy-4-nitro-phenyl)-ethylamine (3-methoxy-4-nitro-phenyl)-acetonitrile (2.6 g, 13.5 mmol) was dissolved in tetrahydrofuran (10 mL), and then a solution of 1 N borane in tetrahydrofuran (67 mL, 67 mmol) was added slowly dropwise at room temperature. After the addition was complete, the reaction was heated at reflux for one hour and TLC showed that the starting material was consumed. The reaction solution was quenched by the dropwise addition of methanol under cooling in ice bath and concentrated to give a crude black oil (2.9 g, 100%), which was used directly in the next reaction. MS: 197.1 [M+H]$^+$.

Step 4. 2-hydroxy-N-[2-(3-methoxy-4-nitro-phenyl)-ethyl]-acetamide (3-methoxy-4-nitro-phenyl)-ethylamine (2.9 g, 0.014 mmol), and methyl glycolate (20.0 g, 0.222 mol) were dissolved in methanol (30 mL) and heated at reflux overnight. TLC showed that the starting material was consumed, and then the reaction solution was concentrated, and the crude product was purified by silica gel column (petroleum ether: ethyl acetate=5:1 to 0:1) to give the product (2.0 g, 56%) as a brown oil.

$^1$H NMR (400 MHz, CDCl$_3$) δ 7.81 (d, J=8.4 Hz, 1H), 6.93 (s, 1H), 6.86 (d, J=8.0 Hz, 1H), 6.80 (s, 1H), 4.05 (s, 2H), 3.95 (s, 3H), 3.61-3.56 (m, 2H), 2.93-2.89 (m, 2H); MS: 255.3 [M+H]$^+$.

Step 5. 2-[1-(4-bromo-phenyl.)-3-(4-fluoro-phenyl)-1-hydro-pyrazol-4-yl]-3-[2-(3-methoxyl-4-nitro-phenyl)-ethyl]-4-carbonyl-oxazoline 2-hydroxy-N-[2-(3-methoxy-4-nitro-phenyl)-ethyl]-acetamide (4.0 g, 3.94 mmol), 1-[1-(4-bromo-phenyl)-3-(4-fluoro-phenyl)-1-hydro-pyrazol-4-formaldehyde (1.4 g, 4.13 mmol), and p-toluenesulfonic acid monohydrate (0.37 g, 1.97 mmol) were dissolved in toluene (20 ml). The mixture was heated to reflux at 150° C. overnight with a water separator to separate water. TLC tests showed that the raw materials disappeared. The reaction was concentrated and the crude material was purified by silica gel column to give the product as a yellow solid (1.1 g, 48%).

$^1$H NMR (400 MHz, DMSO-d$_6$) δ 8.74 (s, 1H), 7.90 (d, J=8.4 Hz, 2H), 7.73-7.64 (m, 5H), 7.29 (t, J=8.4 Hz, 2H), 7.07(s, 1H), 6.80(d, J=8.4 Hz, 1H), 6.05(s, 1H), 4.31-4.23 (m, 2H), 3.85-3.81(m, 1H), 3.77 (s, 3H), 3.14-3.07 (m, 1H), 2.85-2.73 (m, 2H); MS: 581.1 [M+H]$^+$.

Step 6. 241-(4-bromo-phenyl)-3-(4-fluoro-phenyl)-1-hydro-pyrazol-4-yl]-3-[2-(3-hydroxy-4-nitro-phenyl)-ethyl]-4-carbonyl-oxazoline 2-[1-(4-bromo-phenyl)-3-(4-fluoro-phenyl)-1-hydro-pyrazol-4-yl]-3-[2-(3-methoxy-4-nitro-phenyl)-ethyl]-4-carbonyl-oxazoline (0.9 g, 1.55 mmol) was dissolved in dichloromethane (20 mL) and boron tribromide (1.9 g, 7.75 mmol) was added dropwise at −78° C. in a dry-ice acetone bath. The reaction was stirred overnight and the temperature was naturally returned to room temperature. TLC showed that the starting material was consumed, the reaction was quenched with methanol, adjusted to neutral with sodium bicarbonate, and extracted twice with dichloromethane (50 mL×2). The collected organic phases were washed twice with saturated saline, dried over anhydrous sodium sulfate, and filtered, and the filtrate was concentrated to give a crude yellow solid (777 mg) that was used directly in the next reaction. MS: 569.1 [M+H]$^+$.

Step 7. 2-[1-(4-bromo-phenyl)-3-(4-fluoro-phenyl)-1-hydro-pyrazol-4-yl]-3-[2-(3-hydroxy-4-amino-phenyl)-ethyl]-4-carbonyl-oxazoline 2-[1-(4-bromo-phenyl)-3-(4-fluoro-phenyl)-1-hydro-pyrazol-4-yl]-3-[2-(3-hydroxy-4-nitro-phenyl)-ethyl]-4-carbonyl-oxazoline (777 mg, 1.37 mmol) was dissolved in methanol (50 mL), Ra—Ni (100 mg) was added, and the mixture was stirred at atmospheric pressure for 1 hour. TLC showed the starting material was consumed. The reaction solution was filtered through celite and the filtrate was concentrated to give a brown solid (660 mg) which was used directly in the next step. MS: 537.1 [M+H]+.

Step 8. 6-(2-{2-[1-(4-bromo-phenyl)-3-(4-fluoro-phenyl)-1-hydro-pyrazol-4-yl]-4-carbonyl-oxazoline-3-yl}-ethyl)-3- hydro -2-carbonyl-benzoxazole 2-[1-(4-bromo-phenyl)-3-(4-fluoro-phenyl)-1-hydro-pyrazol-4-yl]-3-[2-(3-hydroxy-4-amino-phenyl)-ethyl]-4-carbonyl-oxazoline (300 mg, 0.559 mmol) was dissolved in anhydrous DMF (10 mL), followed by the addition of carbonyl diimidazole CDI (110 mg, 0.67 mmol) at room temperature. The reaction was heated at 70° C. for one hour. TLC showed the starting material was consumed. The reaction was quenched with 100 mL of water and extracted twice with ethyl acetate (50 mL×2). The collected organic phases were washed three times with saturated saline, dried over anhydrous sodium sulfate, and filtered, and the filtrate was concentrated. The crude product was subjected to HPLC to give a white solid product (100 mg, 32%).

$^1$H NMR (400 MHz, DMSO-d$_6$) δ 11.44 (s, 1H), 8.71 (s, 1H), 7.90 (d, J=8.8 Hz, 2H), 7.72 (d, J=8.8 Hz, 2H), 7.65-7.61 (dd, J=8.8 Hz, 5.6 Hz, 2H), 7.28 (t, J=8.8 Hz, 2H), 7.00 (s, 1H), 6.87-6.80 (m, 2H), 5.97 (s, 1H), 4.30-4.21 (m, 2H), 3.75-3.70 (m, 1H), 3.00-2.94 (m, 1H), 2.71-2.65 (m, 2H); MS: 563.1 [M+H]+.

EXAMPLE 17

5-(2-(2-(1-(4-bromophenyl)-3-(4-fluorophenyl)-1H-pyrazol-4-yl)-4-oxazoline-3-yl)ethyl)benzo[d]oxazole-2(3H)-one

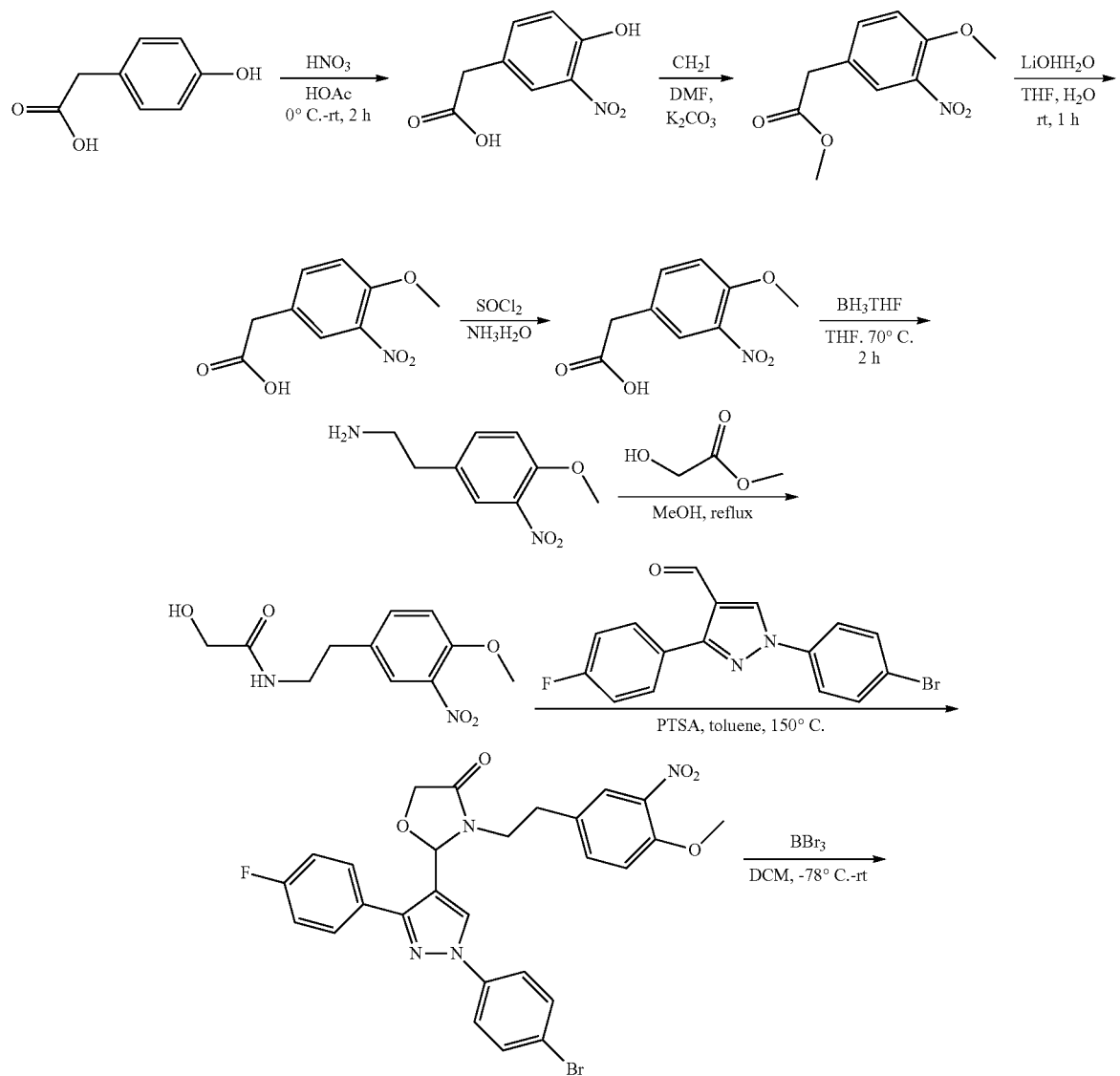

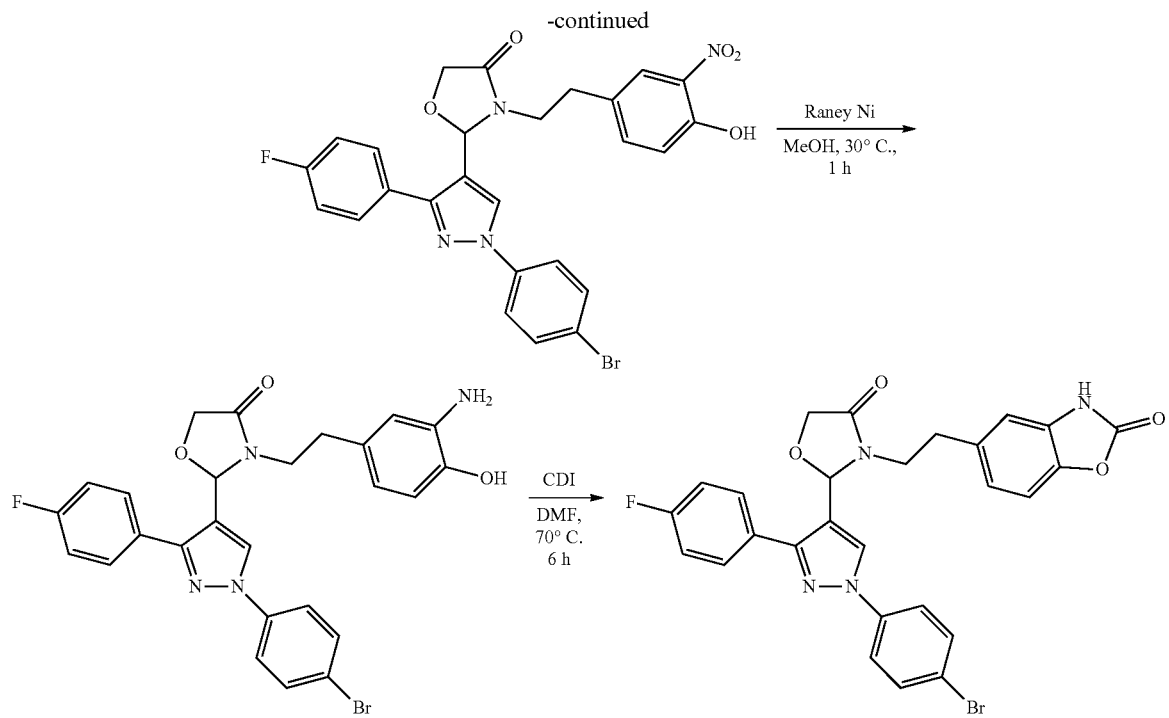

Step 1. 2-(4-hydroxy-3-nitrophenyl)acetic acid 2-(4-hydroxyphenyl)acetic acid (12 g, 78.9 mmol) was dissolved in acetic acid (75 mL), cooled to 0° C., and then nitric acid (65%, 4.08 mL, 91.9 mmol) was added dropwise. The reaction solution was waffled to room temperature and stirred at room temperature for 2 hours. After filtration, the solid was washed with ether (10 mL×2) and dried under reduced pressure to give 2-(4-hydroxy-3-nitrophenyl)acetic acid (10.0 g, 50 mmol, yield: 64%).

$^1$H NMR (400 MHz, DMSO-d$_6$) δ 12.42 (m, 1H), 10.84 (m, 1H), 7.80 (s, 1H), 7.45 (d, J=8.4 Hz, 1H), 7.09 (d, J=8.4 Hz, 1H), 3.60 (s, 2H).

Step 2. methyl 2-(4-methoxy-3-nitrophenyl)acetate 2-(4-hydroxy-3-nitrophenyl)acetic acid (10.0 g, 50 mmol) was dissolved in N,N-dimethylformamide (100 mL) and potassium carbonate (21.0 g, 152.2 mmol) was added into the solution. Methyl iodide (21.0 g, 147.9 mmol) was then added. The reaction mixture was warmed to 50° C. and reacted for 30 min. TLC showed the reaction was completed. The reaction mixture was slowly added into 300 mL of water, filtered, and the solid was washed with water and dried in vacua to give methyl 2-(4-methoxy-3-nitrophenyl) acetate (11.2 g, 49.8 mmol, yield: 98%).

$^1$H NMR (400 MHz, DMSO-d$_6$) δ 7.81 (d, J=2.4 Hz, 1H), 7.57 (dd, J=2.4 and 8.8 Hz, 1H), 7.33 (d, J=8.8 Hz, 1H), 3.91 (s, 3H), 3.75 (s, 2H), 3.63 (s, 3H); MS: 226.3 [M+H]$^+$.

Step 3. 2-(4-methoxy-3-nitrophenyl)acetic acid

Methyl 2-(4-methoxy-3-nitrophenyl)acetate (8.0 g, 35.6 mmol) was dissolved in tetrahydrofuran (80 mL) and water (20 mL). Lithium hydroxide monohydrate (4.5 g, 106.7 mmol) was slowly added to the reaction solution, and the reaction was stirred at room temperature for 1 hour. Tetrahydrofuran was removed under reduced pressure and the pH was adjusted to 3 with hydrochloric acid (3N). The reaction mixture was stirred for 15 minutes and then filtered. The filter cake was washed with 50 mL of water and dried to give 2-(4-methoxy-3-nitrophenypacetic acid. (6.0 g, 28.4 mmol, yield: 80%).

$^1$H NMR (400 MHz, DMSO-d$_6$) δ 12.46 (m, 1H), 7.79 (d, J=2.4 Hz, 1H), 7.56 (dd, J=2.4 and 8.8 Hz, 1H), 7.32 (d), J=8.8 Hz, 1H), 3.91(s, 3H), 3.64(s, 2H).

Step 4. 2-(4-methoxy-3-nitrophenyl)acetamide 2-(4-Methoxy-3-nitrophenyl)acetic acid (6.0 g, 28.4 mmol) was added to thionyl chloride (20 mL), then the mixture was warmed to 100° C. and reacted for 1 hour. The reaction solution was evaporated to dry and dissolved in tetrahydrofuran (80 mL). The solution was slowly added to aqueous ammonia (50 mL) at 0° C. and reacted at room temperature for 1 hour. Tetrahydrofuran was removed by rotary evaporation. The product was filtered and the cake was dried to give 2-(4-methoxy-3-nitrophenyl)acetamide (5.0 g, 23.8 mmol, yield 84%).

$^1$H NMR (400 MHz, DMSO-d$_6$) δ 7.77 (d, J=2.4 Hz, 1H), 7.53 (dd, J=2.4 and 8.8 Hz, 1H), 7.30 (d, J=8.8 Hz, 1H), 6.95 (brs, 2H), 3.90 (s, 3H), 3.42 (s, 2H); MS: 211.3 [M+H]$^+$.

Step 5. 2-(4-methoxy-3-nitrophenyl)ethanamine 2-(4-Methoxy-3-nitrophenethyl)acetamide (2.0 g, 9.52 mmol) was added to tetrahydrofuran (80 mL), then a solution of borane in tetrahydrofuran (1M, 50 mL, 50 mmol) was added and the mixture was stirred for 1 hour at room temperature. Then, the temperature was raised to 70° C. and the mixture reacted for 2 hours. The reaction solution was quenched with concentrated hydrochloric acid, tetrahydrofuran was removed by rotary evaporation, and the pll was adjusted to 9 with saturated sodium carbonate. The reaction solution was extracted with ethyl acetate (50 mL×3). The extracts were collected, washed with saturated saline and dried over anhydrous sodium sulfate. The filtrate was evaporated to dry to give 2-(4-methoxy-3-nitrophenypethanamine (2 g, 9.52 mmol, yield: 100%). MS: 197.3 [M+H]$^+$.

Step 6.
2-Hydroxy-N-(4-methoxy-3-nitrophenethyl)acetamide 2-(4-Methoxy-3-nitrophenethypethanamine (2.0 g, 10.2 mmol) and methyl glycolate (18.0 g, 200 mmol) were dissolved in 50 mL of methanol and heated at reflux for two days. The reaction solution was cooled to room temperature and concentrated by rotary evaporation to dry. The crude product was purified by silica gel column (petroleum ether: ethyl acetate=5:1-1:2) to give compound of 2-hydroxy-N-(4-methoxy-3-nitrophenethyl)acetamide (550 mg, 2.2 mmol, yield: 21%).

$^1$H NMR (400 MHz, DMSO-d$_6$) δ 7.69 (d, J=2.4 Hz, 1H), 7.41 (dd, J=2.4 and 8.8 Hz, 1H), 7.05 (d, J=8.8 Hz, 1H), 6.81 (brs, 1H), 4.06 (s, 2H), 3.94 (s, 3H), 3.44 (m, 2H), 2.94 (m, 2H); MS: 255.3 [M+H]$^+$.

Step 7. 2-(1-(4-bromophenyl)-3-(4-fluorophenyl)-1H-pyrazol-4-yl)-3-(4-methoxy-3-nitrophenyl)oxazoline-4-one2-Hydroxy-N-(4-methoxy-3-nitrophenethyl)acetamide (550 mg, 2.2 mmol), 1-(4-bromophenyl)-3-(4-fluorophenyl)-1H-pyrazol-4-formaldehyde (747 mg, 2.2 mmol) and p-toluenesulfonic acid monohydrate (74 mg, 0.43 mmol) were dissolved in. 50 mL of toluene. The mixture was heated at 150° C. overnight with a water separator to separate water. TLC (petroleum ether: ethyl acetate=2:1) showed that the starting material was consumed. The reaction solution was concentrated by rotary evaporation and then purified by silica gel column (petroleum ether: ethyl acetate=2:1-0:1) to give compound of 2-(1-(4-bromophenyl)-3-(4-fluorophenyl)-1H-pyrazol-4-yl)-3-(4-methoxy-3-nitrophenyl)oxazoline-4-one (600 mg, 1.03 mmol, yield: 50%).

$^1$H NMR (400 MHz, CDCl$_3$) δ 7.89 (s, 1H), 7.66-7.59 (m, 6H), 7.48 (s, 1H), 7.24 (m, 1H), 7.17 (m, 2H), 6.90 (d, J=8.4 Hz, 1H), 5.95 (s, 1H), 4.34 (dd, J=13.6 and 20.8 Hz, 2H), 3.87 (s, 3H), 3.80 (m, 1H), 3.02 (m, 1H), 2.73 (m, 2H); MS: 581.1, 583.1 [M+H]$^+$.

Step 8. 2-(1-(4-bromophenyl)-3-(4-fluorophenyl)-1H-pyrazol-4-yl)-3-(4-hydroxy-3-nitrophenyl)oxazoline-4-one 2-(1-(4-bromophenyl)-3-(4-fluorophenyl)-1H-pyrazol-4-yl)-3-(4-methoxy-3-nitrophenyl)oxazoline-4-one (600 mg, 1.03 mmol) was dissolved in dichloromethane (10 mL), cooled to -70° C., and then boron tribromide (774 mg, 3.09 mmol) was slowly added. The reaction solution was slowly warmed to room temperature and stirred for 1 hour. TLC (petroleum ether: ethyl acetate =1: 1) showed that the starting material was consumed. The reaction was cooled to -70° C., quenched with methanol (10 mL), and solid sodium bicarbonate (2 g) was added and the reaction mixture was slowly warmed to room temperature and stirred at room temperature for 2 hours. The mixture was filtered and the filtrate was concentrated to dry. 20 mL of ethyl acetate was added to form a solution. The solution was washed with saturated sodium bicarbonate solution (5 mL) and saturated saline, dried over anhydrous sodium sulfate, and filtered, and the filtrate was concentrated to dry to give 2-(1-(4-bromophenyl)-3-(4-fluorophenyl)-1H-pyrazol-4-yl)-3-(4-hydroxy-3-nitrophenyl) oxazoline-4-one (600 mg, 1.03 mmol, yield: 100%). MS: 567.2, 569.1 [M+H]$^+$.

Step 9. 2-(1-(4-bromophenyl)-3-(4-fluorophenyl)-1/1-pyrazol-4-yl)-3-(4-hydroxy-3-aminophenyl)oxazoline-4-one 2-(1-(4-bromophenyl)-3-(4-fluorophenyl)-1H-pyrazol-4-yl)-3-(4-hydroxy-3-nitrophenyl)oxazoline-4-one (600 mg, 1.03 mmol) was dissolved in methanol (10 mL), Raney Ni (100 mg) was added, and the mixture was hydrogenated with a hydrogen balloon at normal pressure at 30° C. After reacting for 1 hour, the reaction solution was filtered and the cake was washed with ethyl acetate. The filtrate was dried by rotary evaporation to obtain a crude product, which was purified by silica gel column to give 2-(1-(4-bromophenyl)-3-(4-fluorophenyl)-1H-pyrazol-4-yl)-3-(4-hydroxy-3-aminophenyl)oxazoline-4-one (250 mg, 0.46 mmol, yield: 45%). MS: 537.1, 539.1 [M+H]$^+$.

Step 10. 5-(2-(2-(1-(4-bromophenyl)-3-(4-fluorophenyl)-1H-pyrazol-4-yl)-4-oxazoline-3-yl)ethyl)benzo[d]oxazole-2(3H)-one 2-(1-(4-bromophenyl)-3-(4-fluorophenyl)-1H-pyrazol-4-yl)-3-(4-hydroxy-3-aminophenyl)oxazoline-4-one (250 mg, 0.46 mmol) and N,N'-carbonyldiimidazole (327 mg, 2.32 mmol) were dissolved in N,N-dimethylformamide (15 mL) and stiffed at 70° C. overnight. After the reaction mixture was concentrated in vacuo to dry, it was purified by preparative HPLC to give 5-(2-(2-(1-(4-bromophenyl)-3-(4-fluorophenyl)-1H-pyrazol-4-yl)-4-oxazoline-3-yl)ethyl)benzo[d]oxazol-2(3H)-one (96.4 mg, 0.17 mmol, yield: 40%).

$^1$H NMR (400 MHz, DMSO-c/$_6$) δ 11.43 (m, 1H), 8.72 (s, 1H), 7.91 (d, J=9.2 Hz, 2H), 7.73 (d, J=8.8 Hz, 2H), 7.65 (d, = 8.8 Hz, 2H), 7.31 (d,J=8.8 Hz,2H),7.02(d,J=8.0 Hz, 1H), 6.79 (s, 1H), 6.76 (d, J=8.0 Hz, 1H), 5.96 (s, 1H), 4.26 (dd, J=13.2 and 21.6 Hz, 2H), 3.73 (m, 1H), 2.94 (m, 1H), 2.70 (m, 2H); MS: 563.2, 565.1 [M+H]$^+$.

EXAMPLE 18

2-(1-(4-bromophenyl)-3-(4-fluorophenyl)-1H-pyrazol-4-yl)-3-(2-(2-carbonyl-2,3-dihydrobenzo[d]thiazol-6-yl)ethyl)-4-carbonyl-oxazoline

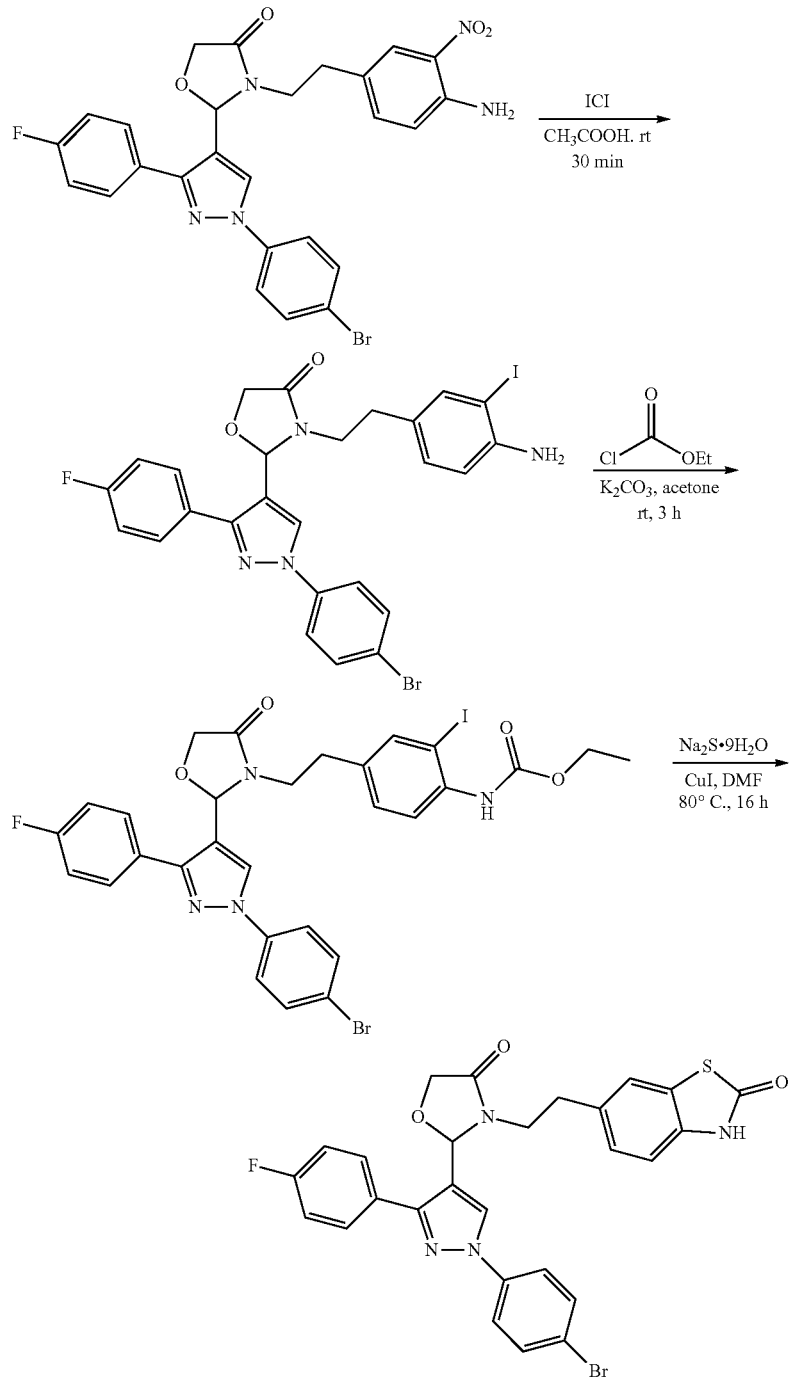

Step 1. 3-(4-amino-3-iodophenyl)-2-(1-(4-bromophenyl)-3-(4-fluorophenyl)-1H-pyrazol-4-yl)-4-carbonyl-oxazoline 3-(4-aminophenyl)-2-(1-(4-bromophenyl)-3-(4-fluorophenyl)-1-hydro-pyrazol-4-yl)-4-carbonyl-oxazoline (100 mg, 0.192 mmol) was dissolved in glacial acetic acid (5 mL), and iodine chloride (37 mg, 0.23 mmol) dissolved in 1 mL of dichloromethane was added dropwise at room temperature, and the mixture was stirred at room temperature for 0.5 hours. The reaction was diluted with 100 mL of water and extracted twice with ethyl acetate (50 mL×2). The collected organic phases were washed twice with saturated saline, dried over anhydrous sodium sulfate, and filtered, and the filtrate was concentrated. The crude product was purified by silica gel column (petroleum ether: ethyl acetate =5:1-1:1) to give the product as a brown solid (100 mg, Yield: 81%).

¹H NMR (400 MHz, CDCl₃) δ 7.79 (s, 1H), 7.64-7.58 (m, 6H), 7.27 (d, J=8.8 Hz, 1H), 7.16 (t, J=8.4 Hz, 2H), 6.80 (d, J=8.0 Hz, 1H), 6.53 (d, J=8.0 Hz, 1H), 5.86 (s, 1H), 4.36-4.27 (m, 2H), 3.97 (s, 2H)), 3.82-3.75 (m, 1H), 2.95-2.88 (m, 1H), 2.62-2.59 (m, 2H); MS: 647.1 [M+H]⁺.

Step 2. ethyl (4-(2-(2-(1-(4-bromophenyl)-3-(4-fluorobenzene)-1-hydro-pyrazol-4-yl)-4-carbonyloxazoline-3-yl)ethyl)-2-iodobenzene)carbamate 3-(4-Amino-3-iodophenyl)-2-(1-(4-bromophenyl)-3-(4-fluorophenyl)-1-hydro-pyrazol-4-yl)-4-carbonyl-oxazoline (100 mg, 0.15 mmol) and potassium carbonate (212 mg, 1.54 mmol) were dissolved in acetone (5 mL), and ethyl chloroformate (90 mg, 1.54 mmol) was then added dropwise at room temperature. The mixture was stirred at room temperature for 2 hours. The reaction was diluted with 100 mL of water and extracted twice with ethyl acetate (50 mL×2). The collected organic phases were washed twice with saturated saline, dried over anhydrous sodium sulfate, and filtered, and the filtrate was concentrated. The crude product was purified by silica gel column (petroleum ether: ethyl acetate=1:1) to give the product as a brown solid (90 mg, yield: 81%).

¹H NMR (400 MHz, CDCl₃) δ 7.86 (d, J=8.4 Hz, 1H), 7.78 (s, 1H), 7.63-7.58 (m, 6H), 7.40 (s, 1H), 7.15 (t, J=8.4 Hz, 2H), 6.98 (d, J=8.4 Hz, 1H), 6.79 (s, 1H), 5.84 (s, 1H), 4.38-4.28 (m, 2H), 3.80-3.74 (m, 1H), 2.98-2.93 (m, 1H), 2.69-2.65 (m, 2H); MS: 721.1 [M+H]⁺.

Step 3. 2-(1-(4-bromophenyl)-3-(4-fluorophenyl)-1-hydro-pyrazol-4-yl)-3-(2-(2-carbonyl-2,3-dihydrobenzo[d]thiazol-6-yl)ethyl)-4-carbonyl-oxazoline In a 100 mL reflux-closed three-neck flask, ethyl (4-(2-(2-(1-(4-bromophenyl)-3-(4-fluorophenyl)-1-hydro-pyrazol-4-yl)-4-carbonyloxazoline-3-yl)ethyl)-2-iodobenzene) carbamate (80 mg, 0.111 mmol), CuI (2.2 mg, 0.011 mmol), and Na₂S.9H₂O (80 mg (0.333 mmol) were dissolved in DMF (5 mL). The mixture was heated at 80° C. under nitrogen and stirred overnight. LC-MS showed that the starting material disappeared and the intermediate was formed. The reaction was cooled to room temperature, then heated to 130° C. under nitrogen protection after 3 mL of glacial acetic acid was added via syringe and then stirred for 3 hours. The reaction solution was cooled to room temperature, and filtered with diatomite. The filter residue was washed with ethyl acetate (50 mL), the filtrate was washed once with 100 mL of water, the aqueous phase was extracted once with ethyl acetate (50 mL), and the collected organic phases were washed three times with saturated saline. The organic phase was dried over anhydrous sodium sulfate, filtered, and the filtrate was concentrated and purified to give a white solid (4 mg, yield: 6%).

¹H NMR (400 MHz, DMSO-d₆) δ 8.77 (s, 1H), 7.95 (d, J=8.4 Hz, 2H), 7.78 (d, J=8.8 Hz, 2H), 7.70 (t, J=8.0 Hz, 2H), 7.34 (t, J=8.8 Hz, 3H), 7.02-6.95 (m, 2H), 6.09 (s, 1H), 4.36-4.28 (m, 2H), 3.79-3.75 (m, 1H), 3.07-3.00 (m, 1H), 2.77-2.68 (m, 2H); MS: 579.2 [M+H]⁺.

EXAMPLE 19

2-(1-(4-bromophenyl)-3-(4-fluorophenyl)-1H-pyrazol-4-yl)-3-(2-(2-oxo-2,3-dihydrobenzo[d]thiazol-5-yl)ethyl)oxazoline-4-one

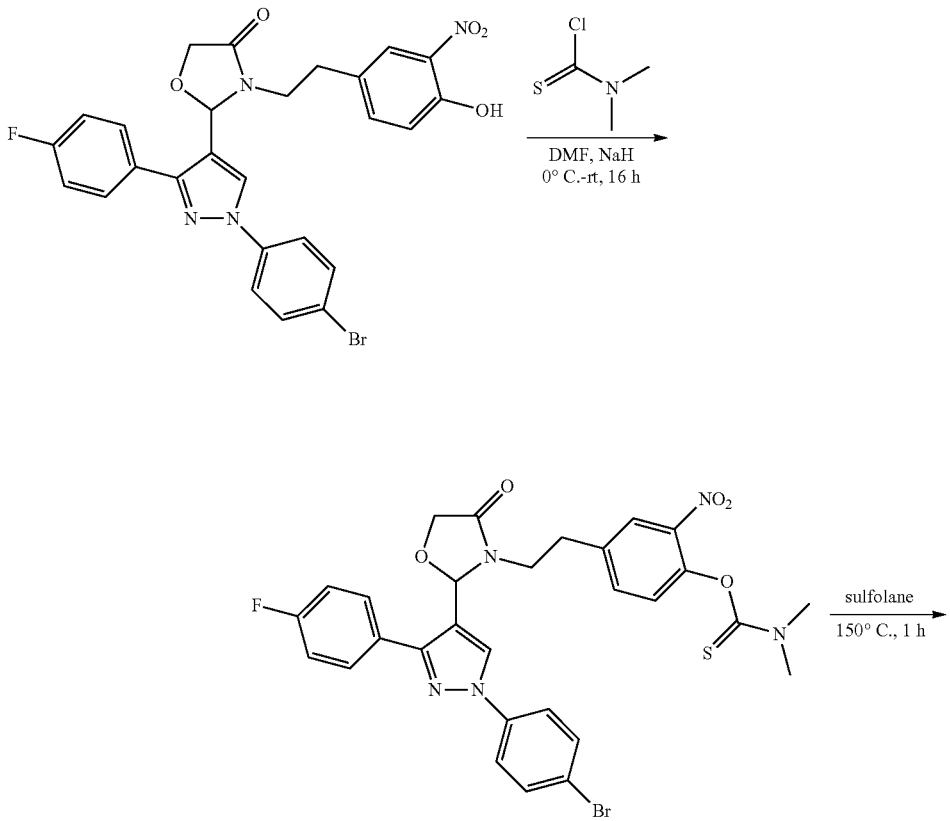

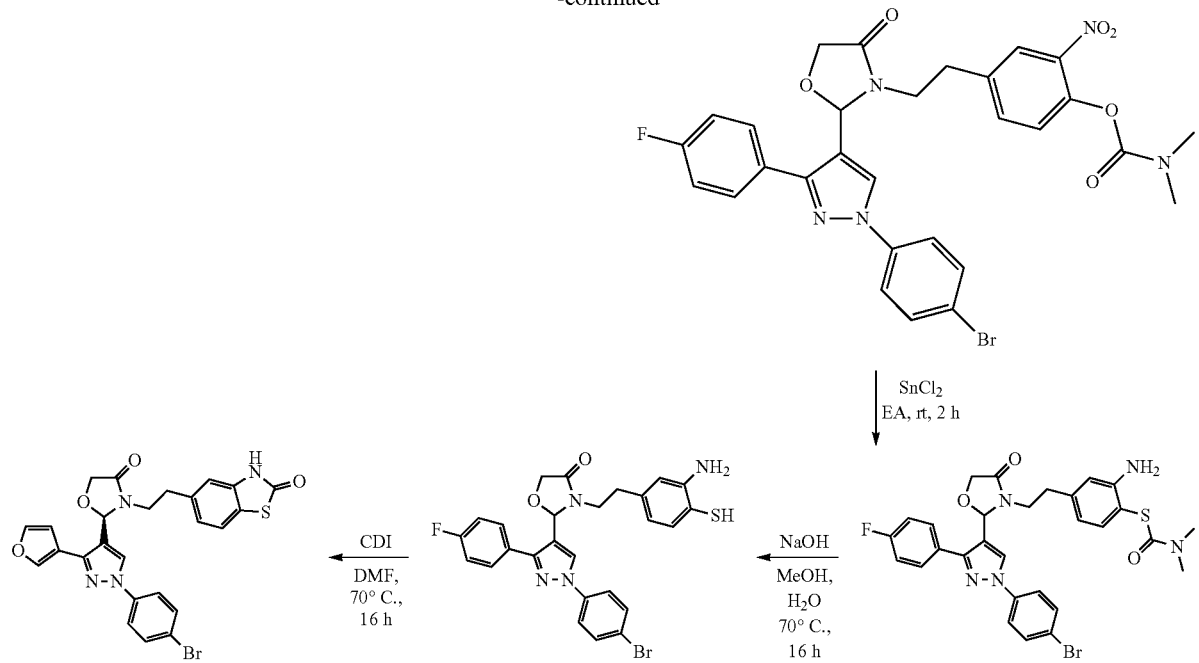

Step 1. O-(4-(2-(2-(1-(4-bromophenyl)-3-(4- fluorophenyl)-1H-pyrazol-4-yl)-4-oxazoline-3-yl)ethyl)-2-nitrophenyl)dimethylaminothiocarboxylic acid 2-(1-(4-bromophenyl)-3-(4-fluorophenyl)-1H-pyrazol-4-yl)-3-(4-hydroxy-3-nitrophenyl)oxazoline-4-one (800 mg, 1.45 mmol) was dissolved in anhydrous DMF (10 mL), sodium hydride (60%, 70 mg, 1.75 mmol) was added at 0° C., and the mixture was stirred for 30 min. Dimethylaminothioacyl chloride (356 mg, 11.18 mmol) was slowly added dropwise to the reaction mixture protected by nitrogen, and the mixture was stirred at room temperature overnight. The reaction solution was poured into ice water and extracted with ethyl acetate. The ethyl acetate phase was washed three times with saturated saline, dried over anhydrous sodium sulfate, filtered and the filtrate was evaporated to dry. The crude product was purified by silica gel column to give O-(4-(2-(2-(1-(4-bromophenyl)-3-(4-fluorophenyl)-1H-pyrazol-4-yl)-4-oxazoline-3-yl)ethyl)-2-nitrophenyl)dimethylaminothiocarboxylic acid (230 mg, 0.35 mmol, yield: 24%).

$^1$H NMR (400 MHz, CDCl$_3$) δ 7.93 (s, 1H), 7.76 (s, 7.70-7.56 (m, 6H), 7.36 (dd, J=8.4, 2.0, 1H), 7.21 7.08 (m, 3H), 5.89 (s, 1H), 4.39-4.28 (m, 2H), 3.86-3.76 (m, 1H), 3.47 (s, 3H), 3.40 (s, 3H), 3.03-2.96 (m, 1H), 2.82 (m, 2H); MS: 654.2, 656.2 [M+H]$^+$.

Step 2. S-(4-(2-(2-(1-(4-bromophenyl)-3-(4-fluorophenyl)-1H-pyrazol-4-yl)-4-oxazoline-3-yl)ethyl)-2-nitrophenyl)dimethylaminothiocarboxylic acid O-(4-(2-(2-(1-(4-bromophenyl)-3-(4-fluorophenyl)-1H-pyrazol-4-yl)-4-oxazol-3-yl) ethyl)-2-nitrophenyl)dimethylamino thiocarboxylic acid (230 mg, 0.35 mmol) was added to sulfolane (2 mL) at room temperature and the temperature was raised to 150° C. under a nitrogen atmosphere and the mixture was reacted for 1 hour. The reaction solution was poured into ice water and extracted with ethyl acetate. The ethyl acetate phase was washed three times with saturated saline, dried over anhydrous sodium sulfate, filtered and the filtrate was evaporated to dry. The crude product was purified by silica gel column to give S-(4-(2-(2-(1-(4-bromophenyl)-3-(4-fluorophenyl)-1H-pyrazol-4-yl)-4-oxazoline-3-yl)ethyl)-2-nitrophenyl)dimethylamino thiocarboxylic acid (230 mg, 0.35 mmol, yield: 100%).

$^1$H NMR (400 MHz, CDCl$_3$) δ 7.95 (s, 1H), 7.66-7.52 (m, 8H), 7.27 (d, J=8.0 Hz, 1H), 7.15 (t, J=8.4 Hz, 2H), 5.79 (s, 1H), 4.39-4.25 (m, 2H), 3.82-3.68 (m, 1H), 3.13 (s, 3H), 3.02 (s, 3H), 3.00-2.95 (m, 1H), 2.86-2.81 (m, 2H); MS: 654.2, 656.2 [M+H]$^+$.

Step 3. S-(2-amino-4-(2-(2-(1-(4-bromophenyl)-3-(4-fluorophenyl)-1H-pyrazol-4-yl)-4-oxazoline-3-yl)ethyl)phenyl)dimethylaminothiocarboxylic acid S-(4-(2-(2-(1-(4-bromophenyl)-3-(4-fluorophenyl)-1H-pyrazol-4-yl)-4-oxazoline-3-yl)ethyl)-2-nitrophenyl)dimethylaminothiocarboxylic acid (230 mg, 0.35 mmol) was dissolved in ethyl acetate (20 mL), and tindichloride (665 mg, 3.5 mol) was added slowly. The mixture was stirred at room temperature overnight. Ethyl acetate (50 mL) was added to dilute the reaction and the pH was adjusted to basic with saturated sodium bicarbonate. The reaction mixture was filtered, the ethyl acetate phase of the filtrate was washed with saturated saline, dried over anhydrous sodium sulfate, filtered, and the filtrate was evaporated to dry to give crude S-(2-amino-4-(2-(2-(1-(4-bromophenyl)-3-(4-fluorophenyl)-1H-pyrazol-4-y l)-4-oxazoline-3-yl)ethyl)phenyl) dimethylaminothioate (200 mg), which was used directly for the next reaction. MS: 624.3, 626.2 [M+H]$^+$.

Step 4. 3-(3-amino-4-mercaptophenethyl)-2-(1-(4-bromophenyl)-3-(4-fluorophenyl)-1H-pyrazol-4-yl) oxazoline-4-one The crude S-(2-amino-4-(2-(2-(1-(4-bromophenyl)-3-(4-fluorophenyl)-1H-pyrazol-4-yl)-4-oxazoline-3-yl)ethyl)

phenyl)dimethylaminothiocarboxylic acid (200 mg) was dissolved in methanol (20 mL) and sodium hydroxide (2N, 2 mL, 4 mol) was added slowly. The mixture was warmed to 70° C. and stiffed overnight. After the reaction solution was cooled to room temperature, the pH was adjusted to 7, methanol was removed by rotary evaporation, and the remain was extracted with ethyl acetate. The ethyl acetate phase was washed with saturated saline, dried over anhydrous sodium sulfate, filtered, and the filtrate was evaporated to dry to give crude 3-(3-amino-4-mercaptophenethyl)-2-(1-(4-bromophenyl)-3-(4-fluorophenyl)-1H-pyrazol-4-yl)oxazoline-4-one (180 mg) which was used directly in the next step.

Step 5. 2-(1-(4-bromophenyl)-3-(4- fluorophenyl)-1H-pyrazol-4-yl)-3-(2-(2-oxo-2,3-dihydrobenzo[d]thiazol -5-yl)ethyl)oxazoline-4-one The crude 3-(3-amino-4-mercaptophenethyl)-2-(1-(4-bromophenyl)-3-(4-fluorophenyl)-1H-pyrazol-4-yl)oxazoline-4-one (180 mg) was dissolved in tetrahydrofuran (20 mL), and N,N'-carbonyldiimidazole (105 mg, 0.648 mmol) was added. After the temperature was raised to 70° C., the mixture was reacted overnight. The reaction solution was evaporated to dry and then prepared by HPLC to give 2-(1-(4-bromophenyl)-3-(4-fluorophenyl)-1H-pyrazol-4-yl)-3-(2-(2-oxo-2,3-dihydrobenzo[d]thiazol-5-yl)ethyl)oxazoline-4-one (14.5 mg, 0.025 mmol).

$^1$H NMR (400 MHz, DMSO-$d_6$) δ 11.71 (s, 1H), 8.73 (s, 1H), 7.90 (d, J=9.2 Hz, 2H), 7.71 (d, 3 =8.8 Hz, 2H), 7.66-7.62 (m, 2H), 7.34-7.27 (m, 3H), 6.82-6.81 (m, 2H), 6.02 (s, 1H), 4.31-4.25 (m, 2H), 3.84-3.66 (m, 1H), 3.00-2.96 (m, 1H), 2.80-2.67 (m, 2H); MS: 579.2, 581.0 [M+H]$^+$.

EXAMPLE 20

2-(1-(4-bromophenyl)-3-(thiophene-3-yl)-1H-pyrazol-4-yl)-3-(2-(2-oxo-2,3-dihydro-1H-benzo[d]imidazol-5-yl)ethyl)oxazolidin-4-one

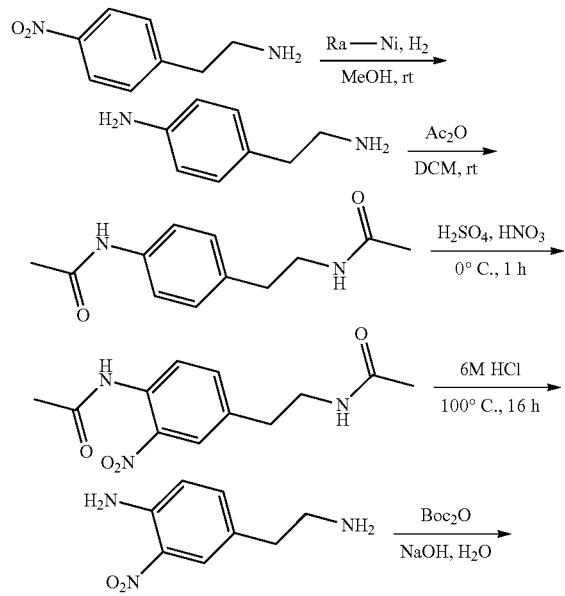

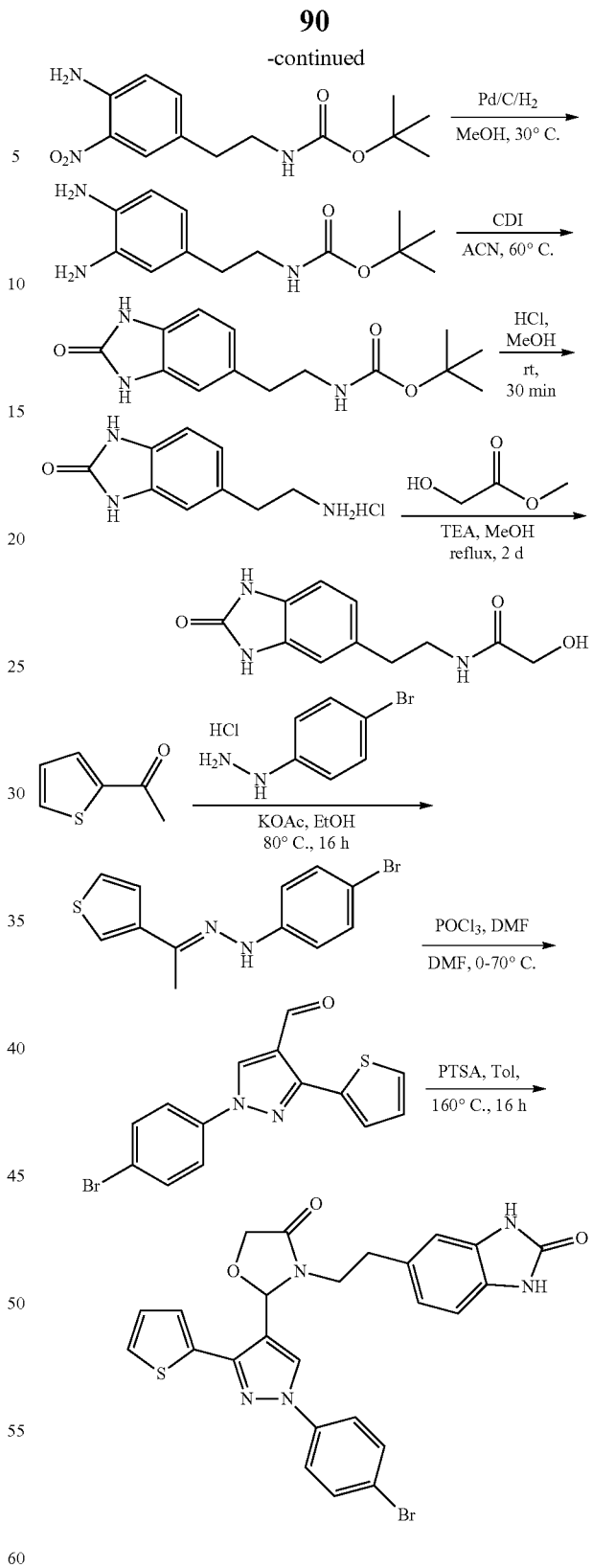

Step 1. 4-(2-aminoethyl)aniline 2-(4-Nitrophenyl)ethanamine (5.0 g, 30 mmol) and Raney Ni (500 mg) were added to methanol (50 mL) and the mixture was stirred under 1 atmosphere of hydrogen overnight. The reaction mixture was filtered, Raney Ni was washed with methanol (50 mL×4), and the filtrate was dried by rotary evaporation to give 4-(2-aminoethyl)aniline (4.1 g, 30 mmol), yield: 100%.

Step 2. N-(4-(2-acetaminoethyl)phenypacetamide 4-(2-Aminoethyl)aniline (4.1 g, 30 mmol) was dissolved in dichloromethane (100 mL), and after the solution was cooled to 0° C., acetic anhydride (15.3 g, 150 mmol) was added dropwise under cooling in an ice bath. The ice bath was removed and the mixture was allowed to react at room temperature for 2 hours. Dichloromethane was removed by rotary evaporation. The concentrated solution was added into 50 mL of water, and stirred for 30 min, and then filtered to give a compound of N-(4-(2-acetaminoethyl)phenypacetamide (4.9 g, 22.3 mmol, yield: 74%). MS: 221.2 [M+H]$^+$.

Step 3. N-(4-acetamino-3-nitrophenethyl)acetamide

N-(4-(2-acetaminoethyl)phenyl)acetamide (4.9 g, 22.3 mmol) was dissolved in concentrated sulfuric acid (30 mL), and after the reaction solution was cooled to 0° C. under cooling in an ice bath, fuming nitric acid (2.1 g, 33.3 mmol) was slowly added dropwise and the ice bath was removed and the mixture was allowed to react at room temperature for 1 hour. The reaction solution was slowly added into 400 mL of ice water by the bottle wall, and stirred for 15 minutes and then filtered. The filter cake was washed with 50 mL of water, and the filter cake was dried to obtain crude N-(4-acetamino-3-nitrophenethyl)acetamide (5.2 g), which was used directly for the next reaction.

Step 4. 4-(2-aminoethyl)-2-nitroaniline

The crude N-(4-acetamino-3-nitrophenethyl)acetamide (5.2 g) was added to hydrochloric acid (6 M, 60 mL) and then warmed to 100° C. and reacted overnight (16 hours). The reaction solution was evaporated to dry, to which was added saturated sodium bicarbonate, and the mixture was extracted with ethyl acetate. The ethyl acetate phase was washed with saturated saline, dried over anhydrous sodium sulfate, filtered, and the filtrate was evaporated to give crude 4-(2-aminoethyl)-2-nitroaniline (1.5 g), which was used directly for the next reaction. MS: 182.0 [M+H]$^+$.

Step 5. tert-butyl-4-amino-3-nitrophenyl carbamate

The crude 4-(2-aminoethyl)-2-nitroaniline (1.5 g, about 8.3 mmol) was added to sodium hydroxide (1M, 50 mL) and Boc$_2$O (2.2 g, 10.1 mmol) was added with stirring. The mixture was stirred at room temperature overnight. The reaction solution was adjusted to pH 7-8 with dilute hydrochloric acid and extracted with ethyl acetate. The ethyl acetate phases were collected, dried over anhydrous Na$_2$SO$_4$, filtered, and the filtrate was dried by rotary evaporation to give a crude product, which was purified by silica gel column (petroleum ether: ethyl acetate=20:1 to 5:1) to give tert-butyl-4-amino-3-nitrophenylcarbamate (1.8 g, 6.4 mmol). MS: 304.3 [M+Na]$^+$.

Step 6. tert-butyl tort-butyl 3,4-diaminophenethylcarbamate

Tert-butyl-4-amino-3-nitrophenylcarbamate (1.8 g, 6.4 mmol) was dissolved in methanol (100 mL), Pd/C (0.36 g) was added, hydrogen gas was introduced, and the mixture was stirred at 30° C. for 16 hours. Then the mixture was filtered and concentrated to give tert-butyl tert-butyl 3,4-diaminophenethylcarbamate (1.6 g, 6.4 mmol, yield: 100%). MS: 274.3 [M+Na]$^+$.

Step 7. tert-butyl tert-butyl (2-(2-oxo-2,3-dihydro-1H-benzo[d]imidazol-5-yl) ethyl)carbamate Tert-butyl tert-butyl 3,4-diaminophenethylcarbamate (1.6 g, 6.4 mmol) was added to acetonitrile (30 mL) and N,N'-carbonyldiimidazole (CDI) (1.2 g, 7.4 mmol) was added with stirring. The reaction solution was warmed to 60° C. and stirred for 3 hours. The reaction solution was dried by rotary evaporation and the crude product was purified by silica gel column to give tert-butyl tert-butyl (2-(2-oxo-2,3-dihydro-1H-benzo[d]imidazol-5-yl)ethyl)carbamate (1.3 g, 4.7 mmol, yield: 73%).

Step 8. 5-(2-aminoethyl)-1H-benzo[d]imidazol-2 (3H)-one hydrochloride

Tert-butyl tert-butyl (2-(2-oxo-2,3-dihydro-1H-benzo[d]imidazol-5-yl) ethyl)carbamate (1.3 g, 4.7 mmol) was added to methanol (30 mL), 6 M hydrochloric acid in methanol (10 mL) was added dropwise with stirring at room temperature, and the mixture was stirred for another 30 min. The reaction solution was concentrated to dry to give 5-(2-aminoethyl)-1H-benzo[d]imidazol-2(3H)-one hydrochloride (1.3 g). MS: 178.3 [M+H]$^+$.

Step 9. 2-hydroxy-N-(2-(2-oxo-2,3-dihydro-1H-benzo[d] imidazol-5-yl) ethyl)acetamide 5-(2-aminoethyl)-1H-benzo[d] imidazol-2(3H)-one hydrochloride (1.3 g, 4.7 mmol), methyl glycolate (8.5 g, 94.4 mmol), and triethylamine (1.4 g, 13.8 mmol) were dissolved in 20 mL of methanol and heated at reflux for two days. The reaction mixture was cooled to room temperature and concentrated by rotary evaporation. The crude product was purified by silica gel column (petroleum ether: ethyl acetate =1:2, then dichloromethane: methanol =3:1) to give 2-hydroxy-N-(2-(2)-oxo-2,3-dihydro-1H-benzo[d]imidazol-5-yl)ethyl)acetamide (2.0 g).
$^1$H NMR (400 MHz, DMSO-d$_6$) δ 10.54 (s, 2H)), 10.50 (s, 1H), 7.72 (s, 1H), 6.83 (d, J=7.6 Hz, 1H), 6.76 (d, J=7.6 Hz, 1H), 3.77 (s, 2H), 3.28 (m, 2H), 2.70 (m, 2H); MS: 236.2 [M+H]$^+$.

Step 10. 1-(4-bromophenyl)-2-(1-(thiophenne-2-yl) ethylidene)hydrazine 1-(Thiophene-2-yl)ethanone (2.0 g, 15.87 mmol), 1-(4-bromophenyl)hydrazine hydrochloride (3.54 g, 15.87 mmol) and potassium acetate (1.56 g, 15.87 mmol) was added to ethanol (32 mL) and stirred overnight at 80° C. After the reaction mixture was concentrated in vacuo to dry, water was added and the mixture was extracted with ethyl acetate. The ethyl acetate phase was concentrated to give a crude product, which was finally washed with a mixed solvent (petroleum ether: ethyl acetate=50:1, 50 mL) to give 1-(4-bromophenyl)-2-(1-(thiophene-2-yl)ethylidene)hydrazine (3.5 g, 11.9 mmol, yield: 75%).
$^1$H NMR (400 MHz, DMSO-d$_6$) δ 7.64 (d, J=6.8 Hz, 1H), 7.37-7.25 (m, 4H), 7.04 (d, J=8.4 Hz, 2H), 2.22 (s), 3H); MS: 295.2, 297.1 [M+H]$^+$.

Step 11. 1-(4-bromophenyl)-3-(thiophene-2-yl)-1H-pyrazol-4-formaldehyde

Phosphorus oxychloride (3.78 g, 24.6 mmol) was slowly added dropwise to anhydrous DMF (3.3 mL) under cooling in an ice bath, and after stirring for 30 min, 1-(4-bromophenyl)-2-(1-(thiophene-2-yl)ethylidene)hydrazine (3.3 g, 11.18 mmol) dissolved in a small amount of anhydrous DMF was slowly added to the reaction mixture under nitrogen protection, and the mixture was stirred at room temperature for 1 hour, and after the temperature was raised to 70° C., the reaction was continued for 5 hours. The reaction solution was poured into ice water and extracted with ethyl acetate. The ethyl acetate phase was washed three times with saturated saline, dried over anhydrous sodium sulfate, filtered, and the filtrate was evaporated to dry to give 1-(4-bromophenyl)-3-(thiophene-2-yl)-1H-pyrazol-4-formaldehyde (3.5 g, 10.5 mmol, yield: 94%).

$^1$H NMR (400 MHz, DMSO-d$_6$) δ 10.04 (s, 1H), 9.38 (s, 1H), 8.43 (s, 1H), 7.96 (d, J=8.4 Hz, 2H), 7.78 (d, J=8.4 Hz, 2H), 7.72 (m, 2H); MS: 335.1 [M+H]$^+$.

Step 12. 2-(1-(4-bromophenyl)-3-(thiophene-2-yl)-1H-pyrazol-4-yl)-3-(2-(2-oxo-2,3-dihydro-1H-benzo[d]imidazol-5-yl)ethyl)oxazolidin-4-one 1-(4-bromophenyl)-3-(thiophene-2-yl)-1H-pyrazol-4-formaldehyde (500 mg, 1.5 mmol), 2-hydroxy-N-(2-(2-oxo-2,3-dihydro-1H-benzo[d]imidazol-5-yl)ethyl)acetamide (500 mg, 1.5 mmol), and p-toluenesulfonic acid monohydrate (366 mg, 2.1 mmol) were dissolved in 100 mL of toluene and N-methylpyrrolidone (10 mL) and heated at 160° C. overnight with a water separator. The reaction solution was concentrated by rotary evaporation and purified by preparative HPLC to give 2-(1-(4-bromophenyl)-3-(thiophene-2-yl)-1H-pyrazol-4-yl)-3-(2-(2-oxo-2,3-dihydro-1H-benzo[d]imidazol-5-yl)ethyl)oxazolidin-4-one (3.6 mg).

$^1$H NMR (400 MHz, DMSO-d$_6$) δ 10.46 (m, 2H), 8.68 (s, 1H), 7.89 (d, J=8.8 Hz, 2H), 7.72-7.65 (m, 4H), 7.42 (q, J=2.0 Hz, 1H), 6.75 (d, J=8.014, 1H), 6.64-6.61 (m, 2H), 4.33-4.21 (m, 2H), 3.69-3.67 (m, 1H), 2.96-2.93 (m, 1H), 2.71-2.59 (m, 2H); MS: 550.1, 552.0 [M+H]$^+$.

EXAMPLE 21

2-(1-(4-bromophenyl)-3-(furan-3-yl)-1H-pyrazol-4-yl)-3-(2-(2-oxo-2,3-dihydro-1H-benzo[d]imidazol-5-yl)ethyl)oxazolidin-4-one

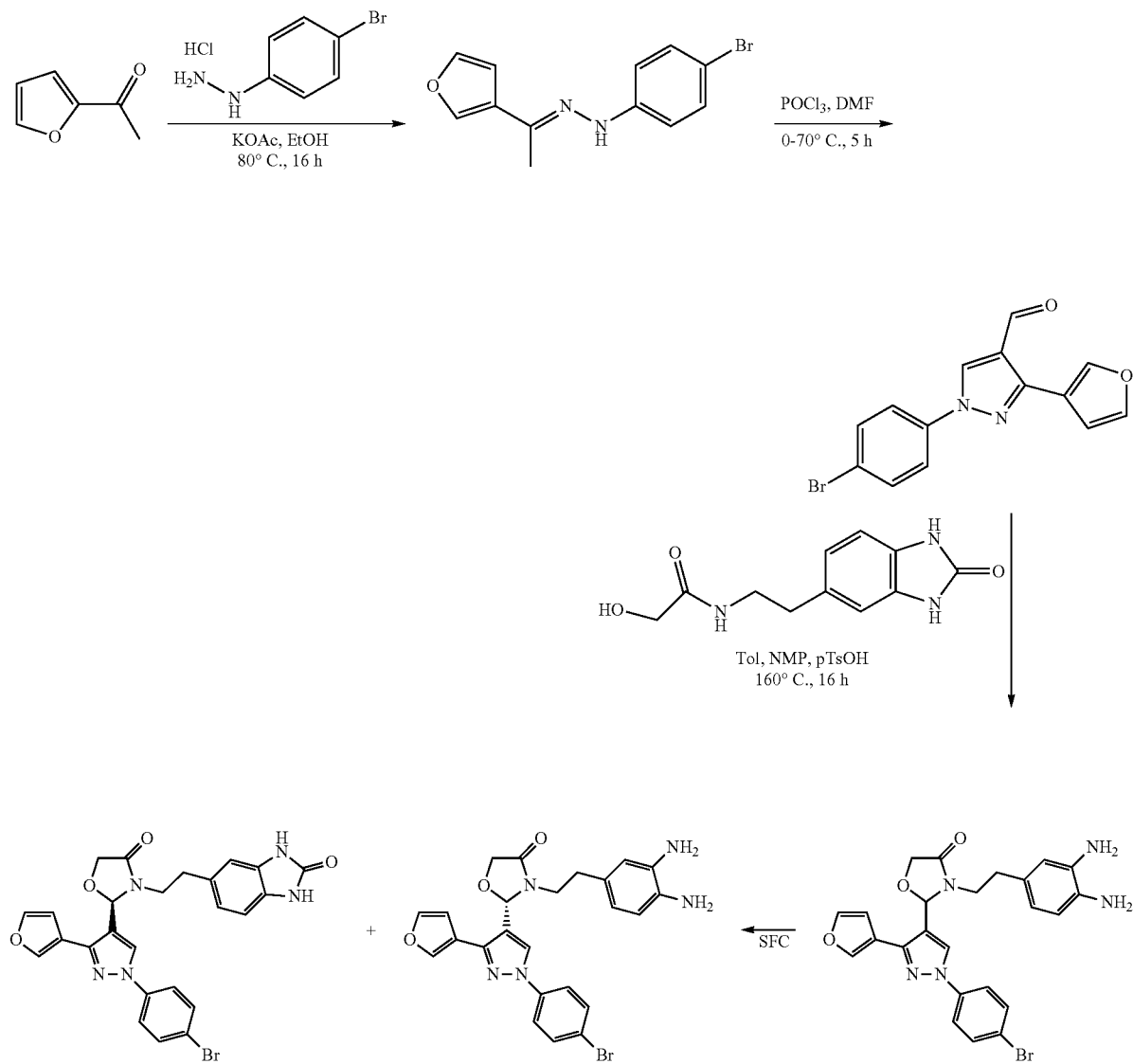

Step 1. 1-(4-bromophenyl)-2-(1-(furan-3-yl)ethylidene)hydrazine 1-(furan-3-yl)ethanone (4.2 g, 38.2 mmol), 1-(4-bromophenyl)hydrazine hydrochloride (8.5 g, 38.2 mmol) and potassium acetate (3.7 g, 38.2 mmol) were added into ethanol (50 mL) and stirred at 80° C. overnight. The reaction mixture was concentrated in vacuo to dry, then water was added, and the mixture was extracted with ethyl acetate. The ethyl acetate phase was concentrated to give a crude product, which was washed with a mixed solvent (petroleum ether: ethyl acetate=50:1, 50 mL) to give 1-(4-bromophenyl)-2-(1-(furan-3-yl)ethylidene)hydrazine (3.8 g, 13.7 mmol, yield: 36%). MS: 279.2, 281.1 [M+H]$^+$.

Step 2. 1-(4-bromophenyl)-3-(furan-3-yl)-1H-pyrazol-4-formaldehyde

Phosphorus oxychloride (1.14 g, 7.46 mmol) was slowly added dropwise to anhydrous DMF (2 mL) under cooling in ice bath, and after stirring for 30 min, 1-(4-bromophenyl)-2-(1-(furan-3-yl)ethylidene)hydrazine (1.0 g, 3.39 mmol) dissolved in a small amount of anhydrous DMF was added slowly under nitrogen protection to the reaction mixture, and the mixture was stirred at room temperature for 1 hour, and after the temperature was raised to 70° C., the reaction was continued for 5 hours. The reaction solution was poured into ice water and extracted with ethyl acetate. The ethyl acetate phase was washed three times with saturated saline, dried over anhydrous sodium sulfate, filtered, and the filtrate was evaporated to dry. The crude product was washed with a mixed solvent (ethyl acetate: petroleum ether =50: 1, 20 mL) and filtered to give 1-(4-bromophenyl)-3-(furan-3-yl)-1H-pyrazol-4-formaldehyde. (1.0 g, 10.5 mmol, yield: 90%). MS: 317, 319.1 [M+H]$^+$.

Step 3. 2-(1-(4-bromophenyl)-3-(furan-3-yl)-1H-pyrazol-4-yl)-3-(2-(2-oxo-2,3-dihydro-1H-benzo[d]imidazol-5-yl)ethyl)oxazolidin-4-one 1-(4-bromophenyl)-3-(furan-3-yl)-1H-pyrazol-4-formaldehyde (500 mg, 1.58 mmol), 2-hydroxy-N-(2-(2-oxo-2,3-dihydro-1H-benzo[d]imidazol-5-yl)ethyl)acetamide (500 mg, 1.5 mmol), and p-toluenesulfonic acid monohydrate (366 mg, 2.1 mmol) were dissolved in 100 mL of toluene and N-methylpyrrolidone (10 mL), and the mixture was heated at 160° C. overnight with a water separator. The reaction solution was concentrated by rotary evaporation and purified by preparative HPLC to give 2-(1-(4-bromophenyl)-3-(furan-3-yl)-1H-pyrazol-4-yl)-3-(2-(2-oxo-2,3-dihydro-1H-benzo[d]imidazol-5-yl)ethyl)oxazolidin-4-one (7.2 mg, yield: 1%).

$^1$H NMR (400 MHz, DMSO-d$_6$) δ 10.47 (s, 2H), 8.68 (s, 1H), 7.90 (s, 1H), 7.86 (d, J=8.8 Hz, 2H), 7.79 (s), 1H), 7.71 (d, J=8.8 Hz, 2H), 6.80 (s, 1H), 6.76 (d, J=7.6 Hz, 1H), 6.64-6.62 (m, 2H), 6.17 (s, 1H), 4.33 (d, J=13.6 Hz, 1H), 4.23 (d, J=13.6 Hz, 1H), 3.68-3.65 (m, 1H), 2.96-2.93 (m, 1H), 2.71-2.60 (m, 2H) MS: 534,536.2 [M+H]$^+$.

2-(1-(4-bromophenyl)-3-(furan -3-yl)-1H-pyrazol-4-yl)-3-(2-(2-oxo-2,3-dihydrogen-1H-benzo[d]imidazol-5-yl)ethyl)oxazolidin-4-one (20 g) was chiral separated via SFC (column: OJ-H; column size: 0.46 cm I.D.×15 cm L; Injection Quantity: 2.0 μl; Mobile phase: HEP/EtOH=60/40 (V/V); Flow rate: 0.5 mL/min; Wavelength: UV 254 nm; Temperature: 25° C.) to give two optical isomers.

(S)-2-(1-(4-bromophenyl)-3-(furan-3-yl)-1H-pyrazol-4-yl)-3-(2-(2-oxo-2,3-dihydro-1H-benzo[d]imidazol-5-yl)ethyl)oxazolidin-4-one, white solid, 8.63 g, yield 43.2%. t$_R$1.766 min, [α]$_D$−43.94° (c 0.5007 g/100 mL, 21.4° C.); purity: 99.64%, ee: 100.0%.

(R)-2-(1-(4-bromophenyl)-3-(furan-3-yl)-1H-pyrazol-4-yl)-3-(2-(2-oxo-2,3-dihydro-1H-benzo[d]imidazol-5-yl)ethyl)oxazolidin-4-one, white solid, 8.26 g, yield 41.3%. t$_R$3.724 min, [α]$_D$+47.00° (c 0.4979 g/1.00 mL, 21.3° C.); purity: 100.00%, ee: 99.03%.

EXAMPLE 22

2-(1-(4-bromophenyl)-3-(furan-2-yl)-1H-pyrazol-4-yl)-3-(2-(2-oxo-2,3-dihydro-1H-benzo[d]imidazol-5-yl)ethyl)oxazolidin-4-one

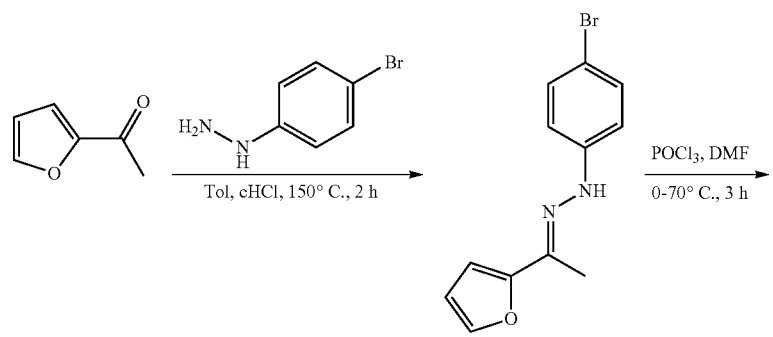

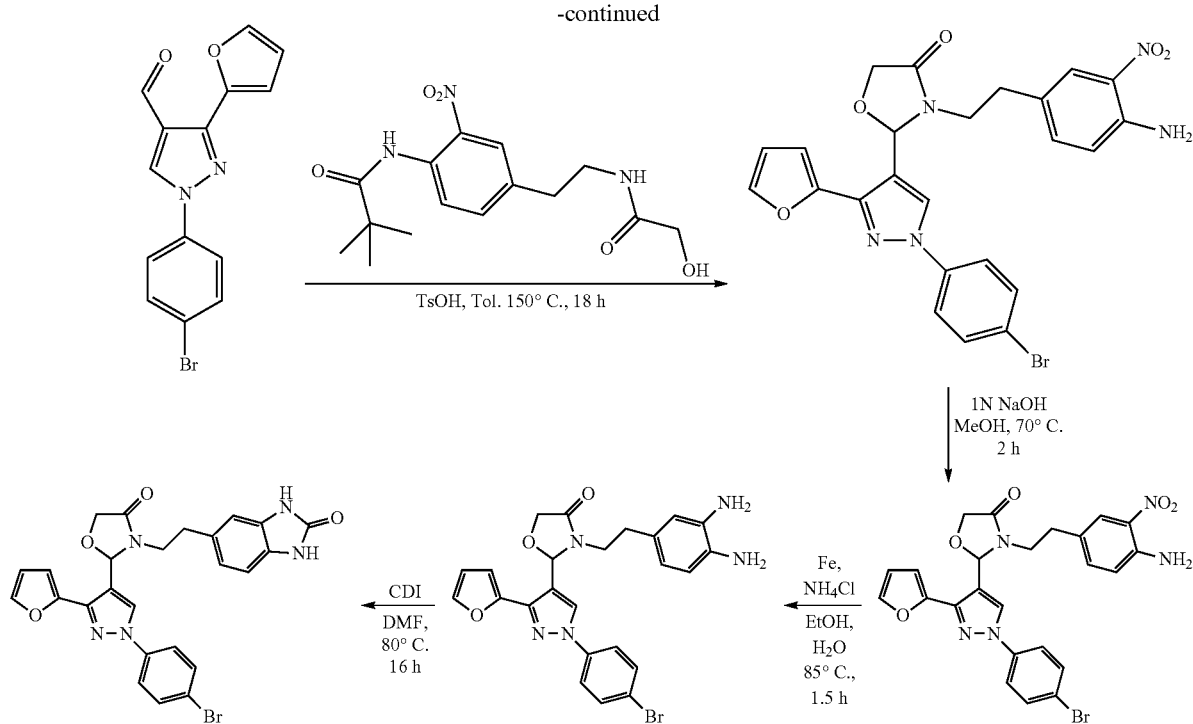

Step 1. (4-bromophenyl)-2-(1-(furan-2-yl)ethyl-idene)hydrazine 1-(furan-2-yl)ethanone (100 g, 0.91 mol) and 1-(4-bromophenyl)hydrazine hydrochloride (162 g, 0.87 mol) were dissolved in toluene (1 L) and 36% hydrochloric acid was added (60 drops). The mixture was heated at 150° C. and stirred for 2 hours with a water separator. The reaction solution was cooled to room temperature. Dichloromethane was added to the reaction solution to dissolve the product and the filtrate was filtered to give a red-black filtrate. The filtrate was dried by rotary evaporation and the crude product was purified by silica gel column chromatography (petroleum ether: dichloromethane =1:1) to give a yellow solid. Petroleum ether was added and the mixture was stirred for 20 min, and filtered to give a pure yellow solid product (68.0 g, yield: 27%).

Step 2. 1-(4-bromophenyl)-3-(furan-2-yl)-1H-pyrazol-4-formaldehyde

Under cooling in ice bath, POCl$_3$ (12.1 g, 78.85 mmol) was slowly added to dry DMF (60 mL). After stirring for 15 min, the mixture was slowly warmed to room temperature and stirred for another 30 min. (4-bromophenyl)-2-(1-(furan-2-yl)ethylidene)hydrazine (10.0 g, 35.84 mmol) was added to the reaction mixture, and the mixture was stirred in incubator for 30 minutes. The temperature was gradually raised to 70° C. and the stirring was continued for 3 hours. The reaction solution was slowly poured into ice water and quenched, stirred at 0° C. for 30 min and filtered. The resulting solid was dissolved in a small amount of ethanol and dichloromethane and then dried by rotary evaporation. The crude product was isolated and purified by silica gel column to give the product as a yellow solid (10.5 g, yield: 92%).

Step 3. 3-(3-nitro-4-tert-butylamidophenethyl)-2-(3-(furan-2-yl)-1-(4-bromophenyl)-1H-pyrazol-4-yl)oxazolidin-4-one Under the protection in nitrogen, 2-hydroxy-N-(3-nitro-4-tert-butylamidophenethyl) acetamide (4.3 g, 13.31 mmol), 1-(4-bromophenyl)-3-(furan-2-yl)-1H-pyrazol-4-formaldehyde (4.22 g, 13.31 mmol) and TsOH (506 mg, 2.66 mmol) were dissolved in toluene (100 mL). The mixture was slowly warm up to 150° C. and refluxed overnight with a water separator. Ethyl acetate (100 mL) was added to the reaction mixture, which was washed with saturated sodium bicarbonate (100 mL) and brine, dried over anhydrous sodium sulfate, and filtered, and the filtrate was concentrated to dry under reduced pressure. The crude product was purified by silica gel column chromatography (petroleum ether: ethyl acetate=5:1) to give the product as a yellow oil (1.8 g, yield: 22%).

Step 4. 3-(3-nitro-4-aminophenethyl)-2-(3-(furan-2-yl))-1-(4-bromophenyl)-1H-pyrazol-4-yl)oxazolidin-4-one Under the protection in nitrogen, 3-(3-nitro-4-tert-butylamidophenethyl)-2-(3-(furan-2-yl))-1-(4-bromophenyl)-1H-pyrazol-4-yl)oxazolidin-4-one (1.42 g, 2.28 mmol) and 1N NaOH (15 mL, 14.27 mmol) were dissolved in methanol (50 mL). The mixture was slowly warmed up to 70° C. and refluxed for 2 hours. Ethyl acetate (100 mL) was added to the reaction solution, which was washed twice with water (100 mL) and saturated saline, dried over anhydrous sodium sulfate, and filtered, and the filtrate was concentrated to dry under reduced pressure by rotary evaporation. After adding silica gel, the crude product was purified by silica gel column chromatography (petroleum ether: ethyl acetate=2:1) to give the product as a yellow oil (720 mg, yield: 60%).

Step 5: 3-(3,4-diaminophenethyl)-2-(3-(furan-2-yl))-1-(4-bromophenyl)-1H-pyrazol-4-yl)oxazolidin-4-one Under the protection in nitrogen, 3-(3-nitro-4-aminophenethyl)-2-(3-(furan-2-yl))-1-(4-bromophenyl)-1H-pyrazol-4-yl)oxazolidin-4-one (500 mg, 0.93 mmol) and reduced iron powder (260 mg, 4.65 mmol) and ammonium chloride (497 mg, 9.3 mmol) were dissolved in ethanol and water (2:1, 30 mL). The temperature was slowly raised to 85° C. and the mixture was refluxed for 1.5 hours. Dichloromethane (50 mL) was added to the reaction solution and iron powder was removed by filtration. After rotary evaporating the solvent ethanol, dichloromethane (50 mL) was added. The mixture was washed once with water (50 mL) and saturated saline, dried over anhydrous sodium sulfate, and filtered, and the filtrate was concentrated to dry under reduced pressure to give the crude product (400 mg), which was used in the next reaction.

Step 6. 2-(1-(4-bromophenyl)-3-(furan-2-yl)-1H-pyrazol-4-yl)-3-(2-(2-oxo-2,3-dihydro-1H-benzo[d]imidazol-5-yl)ethyl)oxazolidin-4-one Under the protection in nitrogen, 3-(3,4-diaminophenethyl)-2-(3-(furan-2-yl))-1-(4-bromophenyl)-1H-pyrazol-4-yl)oxazolidin-4-one (400 mg, 0.8 mmol) and CDI (400 mg, 2.5 mmol) were dissolved in anhydrous DMF (6 mL) and stirred at 80° C. overnight. The reaction solution was extracted with ethyl acetate (2×60 mL), and the organic phase was washed twice with water (100 mL) and saturated saline (150 mL), dried over anhydrous sodium sulfate, and filtered, and the filtrate was concentrated to dry under reduced pressure. After adding silica gel, the crude product was separated and purified by silica gel column (petroleum ether: ethyl acetate =2: 1) to give a pale yellow solid (198 mg, yield: 48%).

$^1$H NMR (400 MHz, DMSO-d$_6$) δ 10.47 (s, 2H)), 8.75 (s, 1H), 7.87 (d, J=8.8 Hz, 2H), 7.78 (s, 1H), 7.73 (d), J=8.8 Hz, 2H), 6.80-6.76 (m, 2H), 6.65-6.63 (m, 3H), 6.31 (s, 1H), 4.34 (d, J=13.2 Hz, 1H), 4.23 (d, J=13.2 Hz, 1H), 3.76-3.64 (m, 1H), 2.98-2.94 (m, 1H), 2.76-2.72 (m, 1H), 2.64-2.61 (m, 1H); MS: 534 [M+H]$^+$.

EXAMPLE 23

Methyl (5-(2-(2-(I -(4-bromophenyl)-3-(4-fluorophenyl)-1H-pyrazol-4-yl)oxazoline-4-one-3-yl)ethyl)-1H-benzo[d] imidazol-2-yl)carbamate

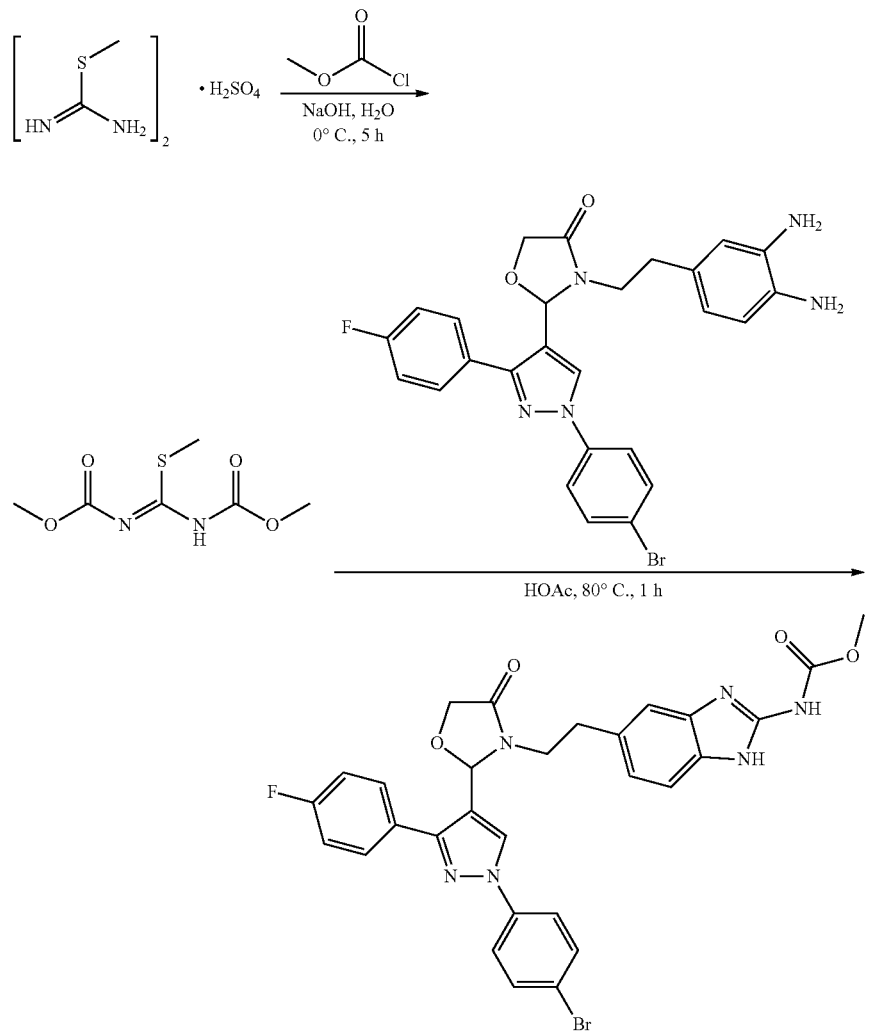

Step 1. 2-methyl-N,N'-dimethoxycarbonylthiourea

2-Methyl-2-thiourea sulfuric acid (1.6 g, 5.75 mmol) was suspended in 15 mL of water and cooled to 0° C. Methyl chloroformate (2.5 g, 26.45 mmol) was added and the mixture was stirred at 0° C. for 5 min. The pH of the reaction solution was maintained at about 9 with a 25% aqueous NaOH solution, and the reaction was stirred for 5 hours, then a large amount of a white solid precipitated. It was filtered and the filter cake was washed with water to give 2-methyl-N,N-dimethoxycarbonylthiourea (1.1 g, yield: 93%).

Step 2. Methyl (5-(2-(2-(1-(4-bromophenyl)-3-(4-fluorophenyl)-1H-pyrazol-4-yl) oxazoline-4-one-3-yl)ethyl)-1H-benzo[d] imidazol-2-yl)carbamate 2-Methyl-N,N'-dimethoxycarbonylthiourea (42 mg, 0.21 mmol) and 2-(1-(4-bromophenyl)-3-(4-fluorobenzene)-1H-pyrazol-4-yl)-3-(3,4-diaminophenethyl)oxazoline-4-one (100 mg, 0.19 mmol) were added into a round bottom flask, and then HOAc (10 mL) was added, the gas in which was replaced with nitrogen. The reaction solution was heated to 80° C. and reacted for 1 hour. The solvent was removed by rotary evaporation and the crude product was washed with methanol to give the product as a white solid (65 mg, yield: 56%).

$^1$H NMR (400 MHz, DMSO-$d_6$) δ 11.48 (br s, 2H), 8.64 (s, 1H), 7.86 (d, J=8.8 Hz, 2H), 7.70 (d, J=8.8 Hz, 2H), 7.61-7.58 (m, 2H), 7.27-7.20 (m, 3H), 7.09 (s, 1H), 6.77 (d, J=8.4 Hz, 1H), 5.99 (s, 1H), 4.29-4.21 (m, 2H), 3.74-3.70 (m, 4H), 2.98-2.93 (m, 1H), 2.78-2.68 (m, 2H); MS: 619 [M+H]$^+$.

EXAMPLE 24

Anti-HBV Activity Experiment In Vitro

Compound Dilution: initial concentrations of all compounds used in the anti-HBV activity experiments in vitro were 1 µM, 3-fold diluted into 8 concentrations; initial concentrations of all compounds used in the cytotoxicity assay were 100 µM, 3-fold diluted into 8 concentrations; and the mother liquor of the compound was diluted with DMSO. The control compound was lamivudine, which had an initial concentration of 100 nM in the anti-HBV activity experiment in vitro and an initial concentration of 100 µM in the cytotoxicity assay, 3-fold diluted into 8 concentrations.

Anti-HBV Activity Experiment In Vitro: HepG2.2.15 cells (4×10$^4$ cells/well) were seeded in 96-well plates and cultured overnight at 37° C. in 5% CO$_2$. The next day, fresh cultures containing compounds in different concentrations were added into the culture wells. On the fifth day, the old culture medium in the culture wells was aspirated and removed. Fresh medium containing compounds in different concentrations was added. On the eighth day, supernatants in the culture wells were collected and used to extract HBV DNA in the supernatant. qPCR assay was used to detect HBV DNA content in the HepG2.2.15 supernatant.

The data analysis and the percentage of inhibition calculation: the percentage of inhibition was calculated by using the following formula:

Inhibition %=[(HBV amount in DMSO control−HBV amount in sample)/HBV amount in DMSO control]×100%.

Using the above test methods, the structures of parts of compounds in the present invention and the corresponding anti-HBV activities are shown in the following table.

| compound | structure | EC$_{50}$ (nM) |
|---|---|---|
| example 1 | 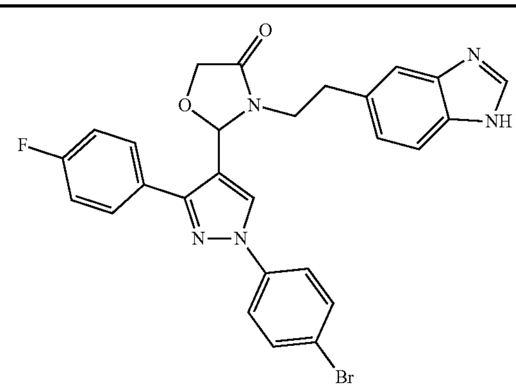 | 50.29 |
| example 1 intermediate | 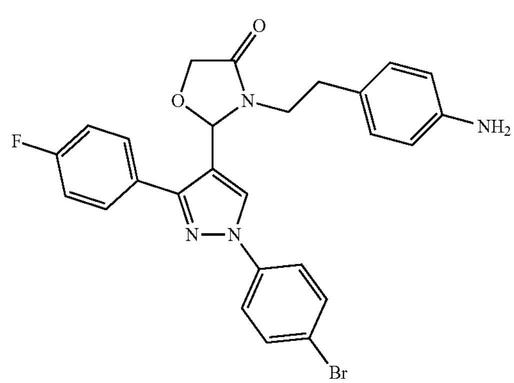 [SMILES: Nc1ccc(CCN2C(=O)COC2c2cn(-c3ccc(Br)cc3)nc2-c2ccc(F)cc2)cc1] | 11.77 |

-continued

| compound | structure | EC$_{50}$ (nM) |
| --- | --- | --- |
| example 2 | 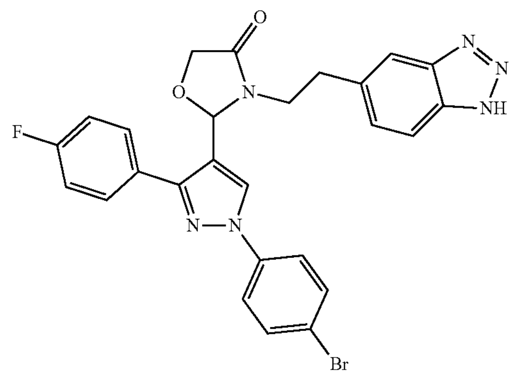 [SMILES: O=C1COC(c2cn(-c3ccc(Br)cc3)nc2-c2ccc(F)cc2)N1CCc1ccc2[nH]nnc2c1] | 68.81 |
| example 3 racemate | 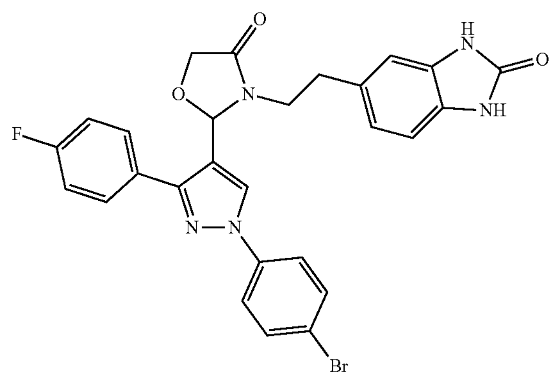 | 31.18 |
| example 3 R isomer | 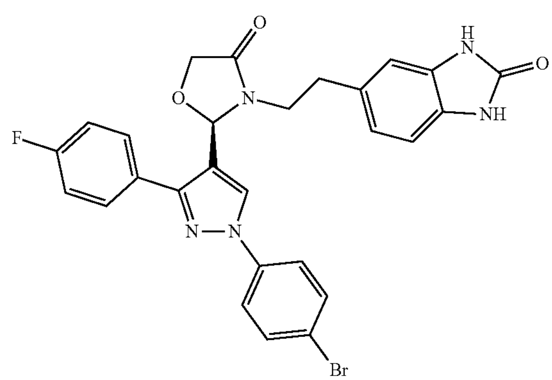 [SMILES: O=C1CO[C@H](c2cn(-c3ccc(Br)cc3)nc2-c2ccc(F)cc2)N1CCc1ccc2[nH]c(=O)[nH]c2c1] | 7.68 |
| example 3 S isomer | 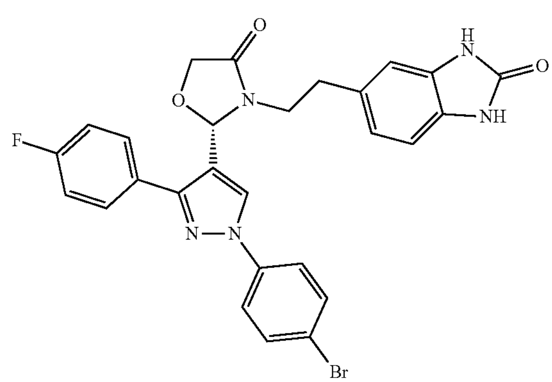 [SMILES: O=C1CO[C@@H](c2cn(-c3ccc(Br)cc3)nc2-c2ccc(F)cc2)N1CCc1ccc2[nH]c(=O)[nH]c2c1] | >1000 |

-continued
| compound | structure | EC$_{50}$ (nM) |
|---|---|---|
| example 4 | 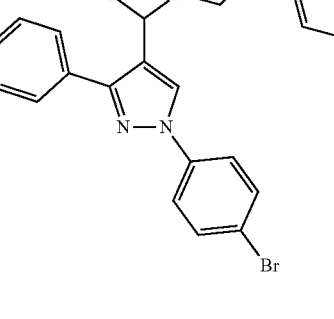 | >1000 |
| example 5 | 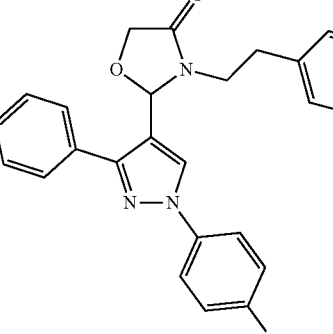 | 45.68 |
| example 6 | 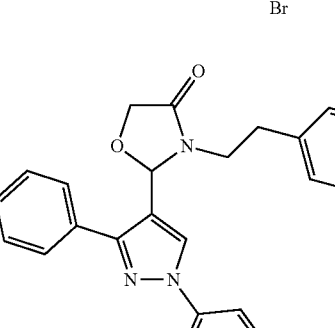 | N/A |
| example 7 | 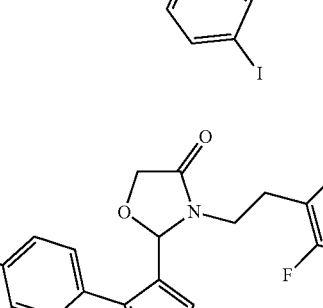 | 67.50 |

-continued

| compound | structure | EC$_{50}$ (nM) |
|---|---|---|
| example 8 racemate | 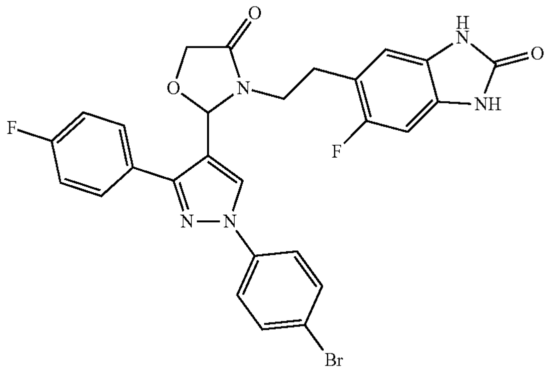 | 35.45 |
| example 8 R isomer | 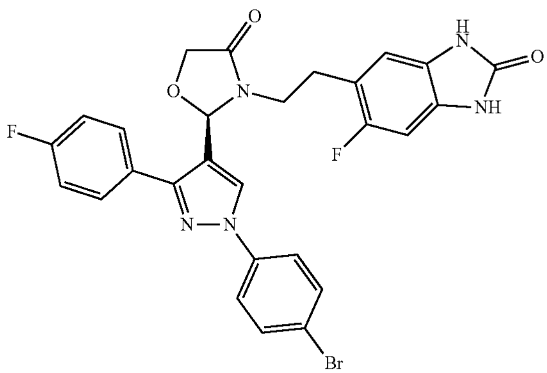 [SMILES: O=C1CO[C@H](c2cn(-c3ccc(Br)cc3)nc2-c2ccc(F)cc2)N1CCc1cc2[nH]c(=O)[nH]c2cc1F] | 15.54 |
| example 8 S isomer | 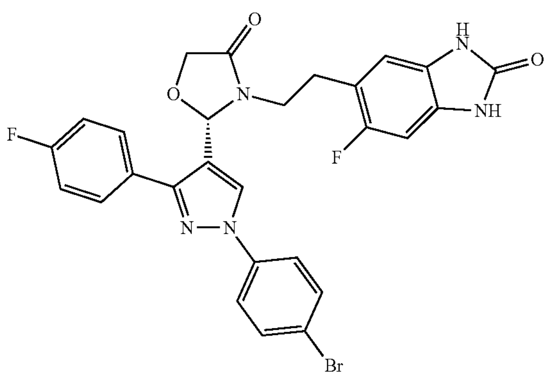 [SMILES: O=C1CO[C@@H](c2cn(-c3ccc(Br)cc3)nc2-c2ccc(F)cc2)N1CCc1cc2[nH]c(=O)[nH]c2cc1F] | >1000 |
| example 9 | 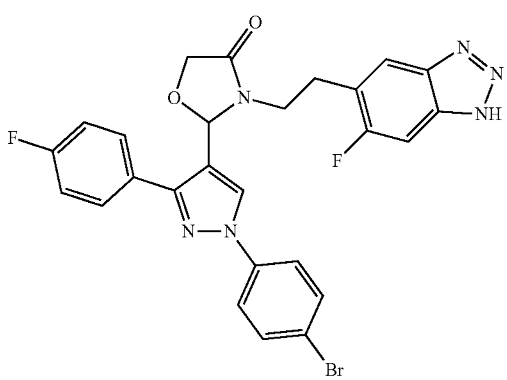 [SMILES: O=C1COC(c2cn(-c3ccc(Br)cc3)nc2-c2ccc(F)cc2)N1CCc1cc2nn[nH]c2cc1F] | 233.80 |

-continued
| compound | structure | EC$_{50}$ (nM) |
|---|---|---|
| example 10 | 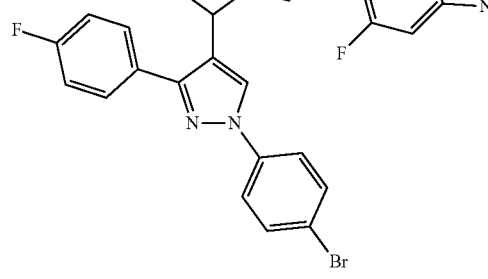 | 134.50 |
| example 11 | 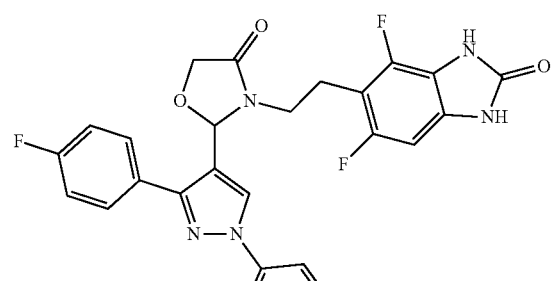 | 101.30 |
| example 12 | 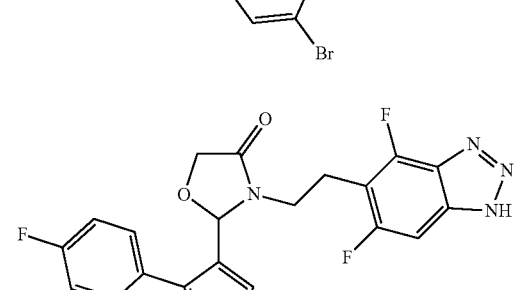 | 223.00 |
| example 13 racemate | 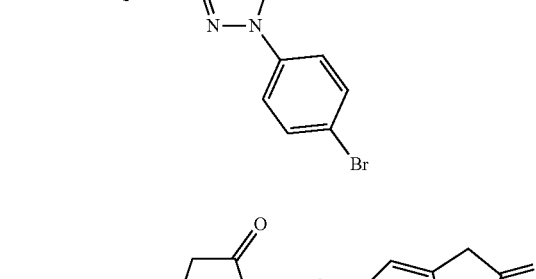 | 21.96 |

-continued
| compound | structure | EC$_{50}$ (nM) |
|---|---|---|
| example 13 R isomer | 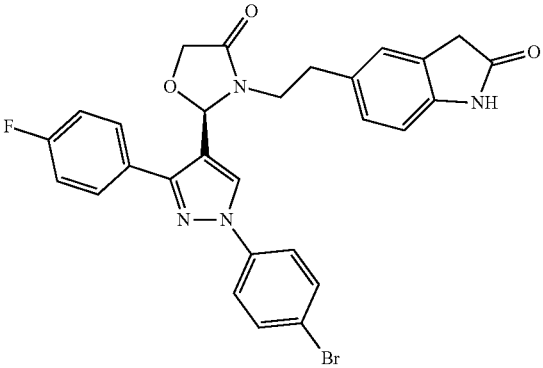 [SMILES: O=C1Cc2cc(CCN3C(=O)CO[C@@H]3c3cn(-c4ccc(Br)cc4)nc3-c3ccc(F)cc3)ccc2N1] | 14.40 |
| example 13 S isomer | 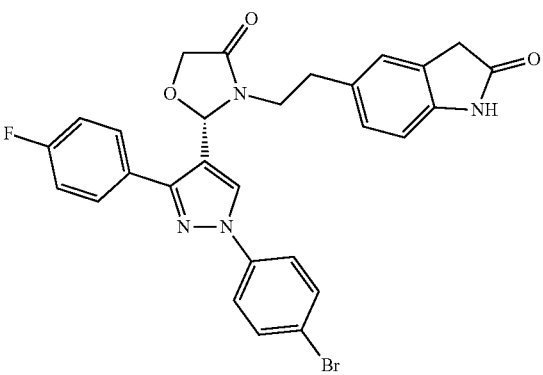 [SMILES: O=C1Cc2cc(CCN3C(=O)CO[C@H]3c3cn(-c4ccc(Br)cc4)nc3-c3ccc(F)cc3)ccc2N1] | >1000 |
| example 14 | 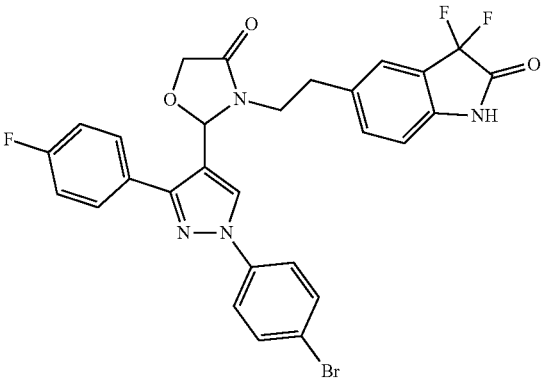 [SMILES: O=C1COC(c2cn(-c3ccc(Br)cc3)nc2-c2ccc(F)cc2)N1CCc1ccc2c(c1)C(F)(F)C(=O)N2] | >1000 |
| example 15 racemate | 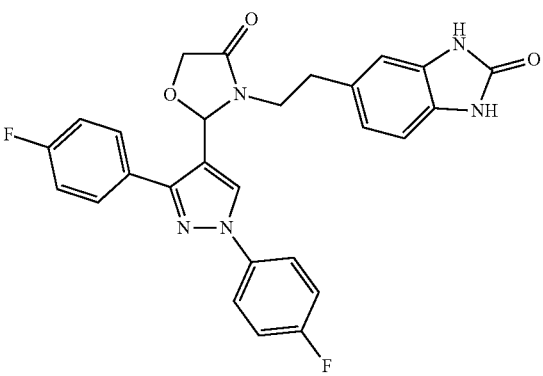 | N/A |

-continued

| compound | structure | EC$_{50}$ (nM) |
|---|---|---|
| example 15 R isomer | 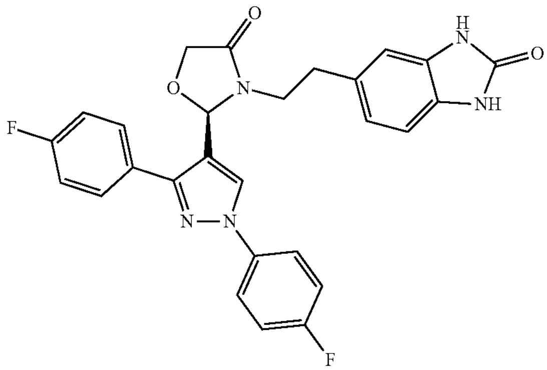 [SMILES: O=C1CO[C@H](c2cn(-c3ccc(F)cc3)nc2-c2ccc(F)cc2)N1CCc1ccc2[nH]c(=O)[nH]c2c1] | 44.46 |
| example 15 S isomer | 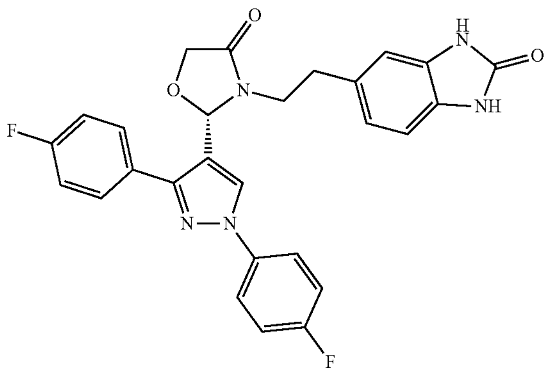 [SMILES: O=C1CO[C@@H](c2cn(-c3ccc(F)cc3)nc2-c2ccc(F)cc2)N1CCc1ccc2[nH]c(=O)[nH]c2c1] | >1000 |
| example 16 | 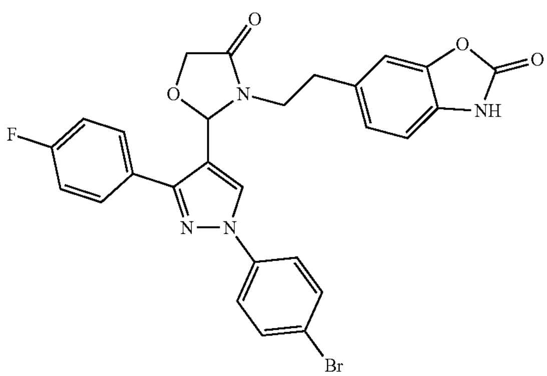 | 80.32 |
| example 17 | 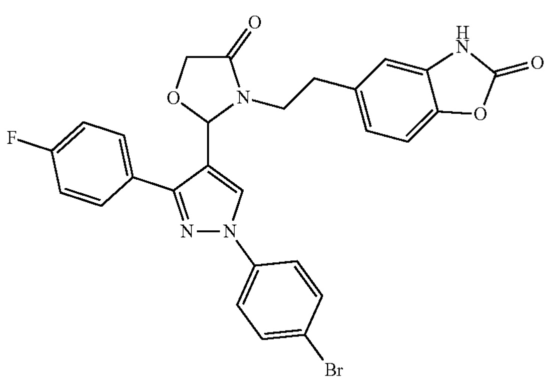 | 150.50 |

-continued

| compound | structure | EC$_{50}$ (nM) |
|---|---|---|
| example 18 | 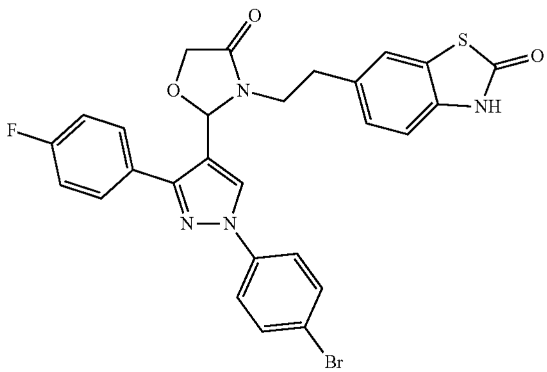 | 60.35 |
| example 19 | 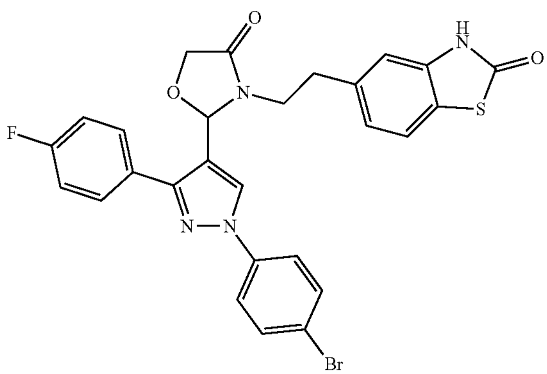 [SMILES: O=C1COC(c2cn(-c3ccc(Br)cc3)nc2-c2ccc(F)cc2)N1CCc1ccc2oc(=O)[nH]c2c1] | 162.00 |
| example 20 | 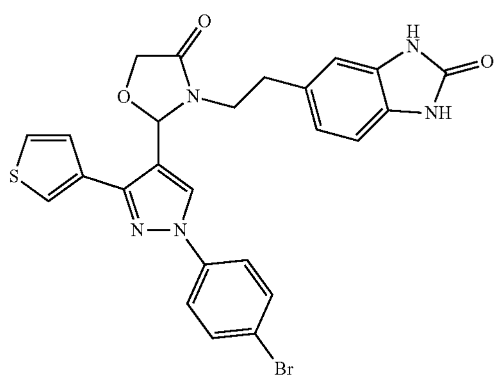 [SMILES: O=C1COC(c2cn(-c3ccc(Br)cc3)nc2-c2ccsc2)N1CCc1ccc2[nH]c(=O)[nH]c2c1] | 20.94 |
| example 21 racemate | 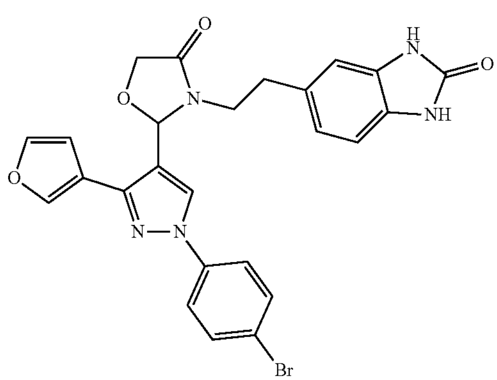 [SMILES: O=C1COC(c2cn(-c3ccc(Br)cc3)nc2-c2ccoc2)N1CCc1ccc2[nH]c(=O)[nH]c2c1] | 30.58 |

-continued
| compound | structure | EC$_{50}$ (nM) |
|---|---|---|
| example 21 R isomer | 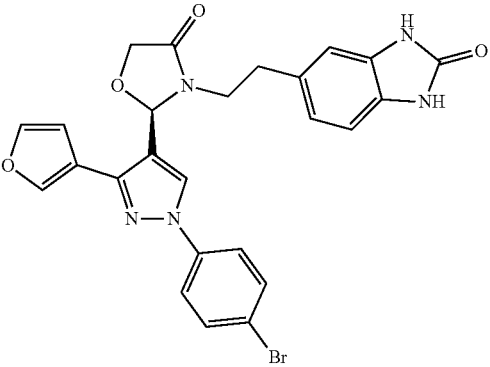 [SMILES: O=C1CO[C@H](c2cn(-c3ccc(Br)cc3)nc2-c2ccoc2)N1CCc1ccc2[nH]c(=O)[nH]c2c1] | 10.97 |
| example 21 S isomer | 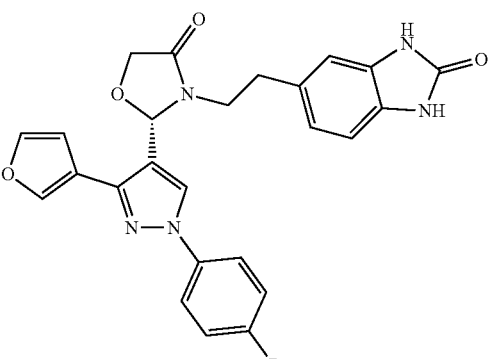 | >1000 |
| example 22 | 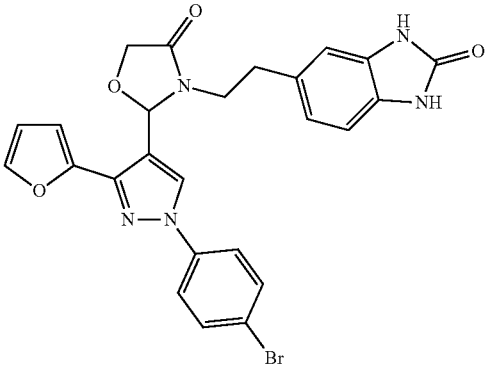 [SMILES: O=C1COC(c2cn(-c3ccc(Br)cc3)nc2-c2ccco2)N1CCc1ccc2[nH]c(=O)[nH]c2c1] | 85.31 |
| example 23 | 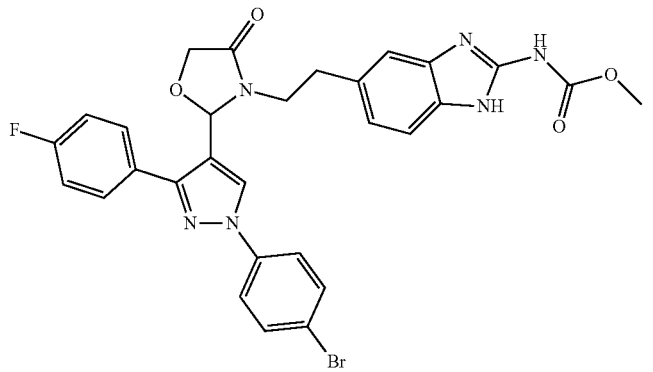 [SMILES: COC(=O)Nc1nc2cc(CCN3C(=O)COC3c3cn(-c4ccc(Br)cc4)nc3-c3ccc(F)cc3)ccc2[nH]1] | 126.80 |

EXAMPLE 25

Anti-Different Genotypic HBV Strain Activity Assay in Vitro

Compounds were tested for in vitro activity against different genotypic HBV strains using a transient transfection cell model. HepG2 cells ($4 \times 10^4$ cells/well) that had been transfected with different HBV genotypic strains were seeded into 96-well plates and cultured overnight at 37° C. in 5% $CO_2$. The next day, fresh cultures containing compounds in different concentrations were added into the culture wells. On the fifth day, the old culture medium in the culture wells was aspirated and removed. The fresh medium containing compounds in different concentrations was added. On the eighth day, supernatants in the culture wells were collected and used to extract HBV DNA in the supernatant. qPCR assay was used to detected HBV DNA content in the HepG2 supernatant. The experimental results are shown in the following table ($EC_{50}$ nM):

|  | compound | | |
| --- | --- | --- | --- |
| HBV genotype | example 3, R isomer | example 13, racemate | Lamivudine |
| AP007263 (A) | 33.89 | 168.30 | 136.10 |
| HE974371 (A2) | 4.67 | 32.46 | 135.70 |
| AB246345 (C) | 6.26 | 30.87 | 97.25 |
| AB246346 (C) | 14.60 | 59.17 | 128.20 |
| JN406371 (B) | 8.69 | 36.05 | 111.80 |
| AB033554 (B) | 13.56 | 47.02 | 155.70 |
| U95551 (D) | 14.39 | 86.81 | 122.60 |

EXAMPLE 26

In Vitro Anti-nucleoside Drug-Resistant HBV Strain Activity Experiment

Compounds were tested for in vitro activity against nucleoside drug-resistant HBV strains using a transient transfection cell model. HepG2 cells ($4 \times 10^4$ cells/well) that had been transfected with nucleoside drug-resistant HBV strains were seeded into 96-well plates and cultured overnight at 37° C. in 5% $CO_2$. The next day, fresh cultures containing compounds in different concentrations were added into the culture wells. On the fifth day, the old culture medium in the culture wells was aspirated and removed. The fresh medium containing compounds in different concentrations was added. On the eighth day, supernatants in the culture wells were collected and used to extract HBV DNA in the supernatant. qPCR assay was used to detect HBV DNA content in the HepG2 supernatant. The experimental results are shown in the following table ($EC_{50}$ nM):

|  | compound | | |
| --- | --- | --- | --- |
| Drug-Resistant Strain | example 3, R isomer | example 13, racemate | Lamivudine |
| M204I | 21.20 | 75.83 | >100000 |
| M204I + V173L | 13.97 | 72.18 | >100000 |
| M204I + S202G | 11.59 | 74.67 | >100000 |
| M204I + S202G + M250V | 13.60 | 87.42 | >100000 |
| L180M + M204V | 18.91 | 102.50 | >100000 |
| U95551 (WT) | 19.13 | 82.02 | 94.93 |

EXAMPLE 27 harmacokinetic Determination

The pharmacokinetics of the compound of Example 3 (racemate) in the present application was determined in rats.

Measurement methods and conditions:

Test compounds were intravenously (IV) and orally (PO) administered to Sprague Dawley rats once. Blood samples were collected at different time points. LC/MS/MS was used to determine the concentration of the test compounds in the rat plasma after the administration of the test compounds and calculate the relating parameters.

Time points for animal blood collection were: before administration, 5 min, 15 min, 30 min, 1 h, 2 h, 4 h, 6 h, 8 h and 24 h after administration. Approximately 0.3 mL of blood via jugular or other appropriate venipuncture was collected from each animal and anticoagulated with heparin sodium. Blood samples were collected and placed on ice, and plasma was centrifuged (centrifugation: 8000 rpm, 6 min, 4° C.). Plasma samples were stored in a −70° C. freezer before analysis.

50 μL of sample was taken into a 1.5 mL centrifuge tube, and 250 μL of internal standard solution was added. After subjected to vortex for 60 seconds and centrifugation for 5 min (14,000 revolutions/min), 200 μL of supernatant was taken into a 96-well sample plate for analysis.

Mass spectrometer: API 4000, Applied Biosystems, Inc., Electrospray Ionization Source (ESI), Tandem quadrupole mass analyzer.

Mass spectrometry conditions: ion source: electrospray ionization source (ESI); auxiliary gas (Gas1): 60 psi; auxiliary gas (Gas2): 60 psi; curtain gas (CUR): 14 psi; collision gas (CAD): 6; ion source voltage (IS): 5500V; ion source temperature (TEM): 550° C.

Liquid phase conditions: chromatography Column: Thermo AQUASIL C18 (50×2.1 mm); chromatographic mobile phase: A is 0.1% formic acid in water, solution B is 0.1% formic acid in methanol (A:B=80%: 20%-10%: 90%); flow rate: 500 μL/min; injection volume: 1 μL.

According to the drug blood concentration data, the pharmacokinetic parameters of the test compound were calculated using the pharmacokinetic calculation software WinNonlin 5.2 non-compartmental model.

The result is as follows.

|  | compound example 3, racemate Administration route | |
| --- | --- | --- |
|  | IV | PO |
| $t_{1/2}$ (h) | 3.52 | 2.07 |
| $T_{max}$ (h) | 0.083 | 0.83 |
| $C_{max}$ (ng/mL) | 5459.25 | 201.02 |
| $AUC_{(0-\infty)}$ (ng/mL*h) | 3884.62 | 773.14 |
| Vz (L/kg) | 6.22 | 3.58 |
| CLz (L/hr/kg) | 1.31 |  |
| F (%) |  | 18.55 |

In addition, the pharmacokinetics of the compound of Example 3 (R isomer) in the present application was determined in mice.

Measurement methods and conditions:

Test compounds were subcutaneously administered to female BALB/c mouse once and blood samples were taken at different time points. LC/MS/MS was used to determine the concentration of the test compounds in the rat plasma after administration of the test compounds and calculate relevant parameters.

Animal blood collection time points were: before administration, 5 min, 15 mM, 30 min, 1 h, 2 h, 4 h, 8 h and 24 h after administration.

Mass Spectrometer: Triple Quad 5500. Mass Spectrometry Conditions: SRM Detection Liquid phase conditions: Column: XSELECT CSHTM XP C18 (2.1×50 mm, 2.5 µm); chromatographic mobile phase: mobile phase A: 0.025% FA & 1 mM NH$_4$OAc in water/CAN solution (v:v, 95: 5), mobile phase B: 0.025% FA & 1 mM NH$_4$OAc in ACN/water solution (v:v, 95: 5) (A:B =65%: 35%-10%: 90%); flow rate: 0.6 mL/min; column temperature: 50° C.

According to the drug blood concentration data, the pharmacokinetic parameters of the test compound were calculated using the pharmacokinetic calculation software WinNonlin 5.2 non-compartmental model.

The result is as follows.

| PK parameters | example 3, R isomer |
|---|---|
| $C_{max}$ (ng/mL) | 643 |
| $T_{max}$ (h) | 1.33 |
| $T_{1/2}$ (h) | 1.19 |
| $AUC_{0\text{-}inf}$ (ng · h/mL) | 2079 |
| $MRT_{0\text{-}inf}$ (h) | 2.40 |

EXAMPLE 28

Determination of Pharmacodynamics in vivo

Measurement methods and conditions:

High pressure injection of HBV DNA in tail vein and administration methods:

HBV plasmid DNA solution was high-pressure injected via the tail veins of the mouse: the plasmid DNA was pre-dissolved in physiological saline (10 µg/1.4 ml, 10 µg/1.5 ml) before injection and stored at 4 until its use. The mice were injected with a plasmid DNA solution at a dosage of 8% of the body weight from the tail vein in 5 seconds. If the injection volume is less than or equal to 1.4 ml, 10 µg/1.4 ml of plasmid solution was used; if the injection volume is greater than or equal to 1.5 ml, 10 µg/1.5 ml of plasmid solution was used.

On $1^{st}$-$7^{th}$ day, the mice were continuously injected intraperitoneally with the test compound or solvent for 7 days. Blood was collected from the submandibular vein on $1^{st}$, $3^{rd}$ and $5^{th}$ days, anticoagulated with heparin sodium, centrifuged at 4° C. in 7,000×g for 10 minutes to prepare plasma. The plasma was divided into two and one was sent to anti-infective groups in the Department of Biology for HBV DNA detection, and the other was ready for use.

On $7^{th}$ day, after all mice were euthanized by $CO_2$, blood was collected from the heart to prepare plasma, and liver tissues were collected. The liver tissue was divided into three sections, wherein two collected from the left lobes were immediately quick-frozen in liquid nitrogen and transferred to be stored at −80 degrees until they were sent to in vitro anti-infective groups in the Department of Biology in WuXi Apptech for HBV DNA detection. The remaining liver tissue was frozen in dry ice and transferred to be stored at -80 degrees for standby application.

Sample Analysis:

Quantitative PCR was used to detect the content of HBV DNA in mouse plasma.

According to the Q1Aamp 96 DNA Blood Kit instructions, DNA from mouse plasma was extracted.

Quantitative PCR detection of HBV DNA content: In order to rule out possible interference with injected HBV plasmid DNA, two sets of primers and probes were used simultaneously for the assay. One set of primers and probes was used to identify the HBV DNA sequence (HBV primers) and could simultaneously detect HBV plasmid DNA and replicated HBV DNA, and the other set of primers and probes was used to recognize the pAAV2 vector sequence (pAAV2 primer) and only HBV plasmid DNA could be detected.

HBV DNA content =DNA content detected by HBV primers - DNA content detected by pAAV2 primers The Result was as Follows:

The dose of the test compound (compound of Example 3, R isomer) was 25 mpk. The HBV DNA content in mouse plasma was significantly reduced on the $1^{st}$ and $3^{rd}$ days, with a decrease of 0.55 log and 1.84 log, respectively, with a statistic difference.

What is claimed:

1. A compound having formula I, or a pharmaceutically acceptable salt or enantiomer or tautomer thereof:

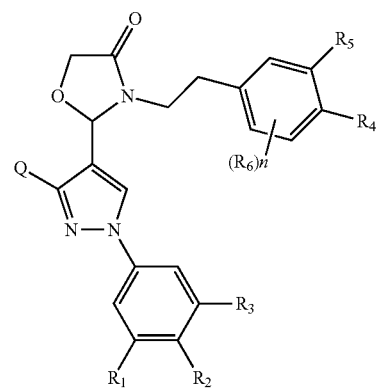

(I)

wherein:

each of $R_1$, $R_2$ and $R_3$ is independently selected from hydrogen, halogen, optionally substituted alkyl, amino and hydroxyl;

$R_4$ and $R_5$, together with the carbon atoms to which they are attached, form an optionally substituted five-membered heterocyclic or heteroaryl group containing at least one nitrogen atom, wherein —CH$_2$— in the heterocyclic group is optionally replaced by —C(═O)—, —C(═S)—, or —C(═NH)—;

$R_6$ is selected from deuterium, halogen, amino and hydroxyl;

n is 0, 1 or 2; and

Q is aryl or heteroaryl, wherein the aryl or heteroaryl is optionally substituted with one or more halogens.

2. The compound of claim 1, being a compound of formula I-R, or a pharmaceutically acceptable salt or enantiomer or tautomer thereof:

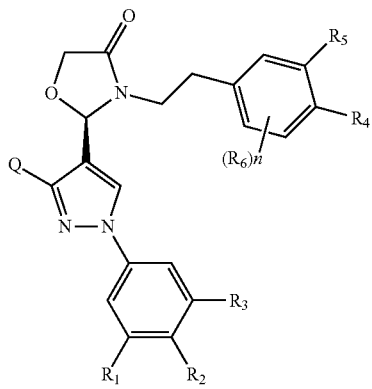

wherein the chiral carbon atom is in R-configuration.

3. The compound of claim 1, wherein:
each of $R_1$, $R_2$ and $R_3$ is independently hydrogen or halogen;
$R_4$ and $R_5$, together with the carbon atoms to which they are attached, form an optionally substituted five-membered heterocyclic or heteroaryl group containing at least one nitrogen atom, wherein —CH$_2$— in the heterocyclic group is optionally replaced by —C(=O)—, —C(=S)—, or —C(=NH)—;
$R_6$ is deuterium or halogen;
Q is aryl or heteroaryl, wherein the aryl or heteroaryl is optionally substituted with one or more halogens, the aryl is phenyl, and the heteroaryl is selected from furyl, pyrrolyl and thienyl.

4. The compound of claim 1, wherein Q is p-fluorophenyl, thienyl or furyl.

5. The compound of claim 1, wherein

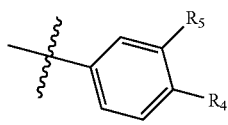

in formula I
is selected from:

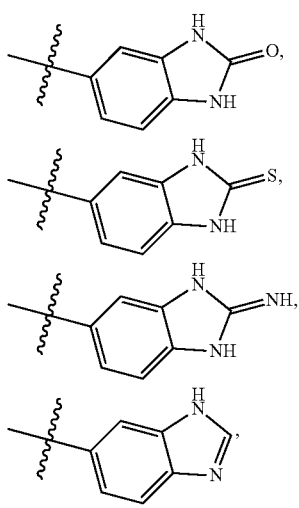

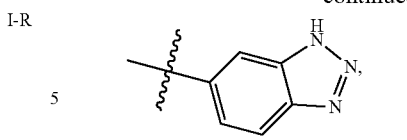

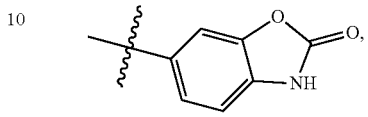

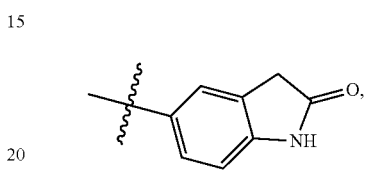

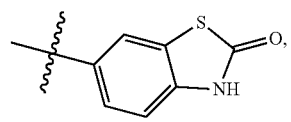

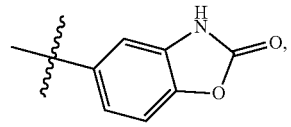

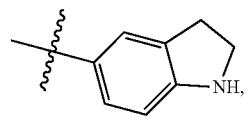

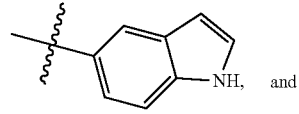, and

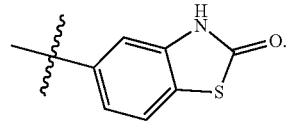

6. A compound selected from:

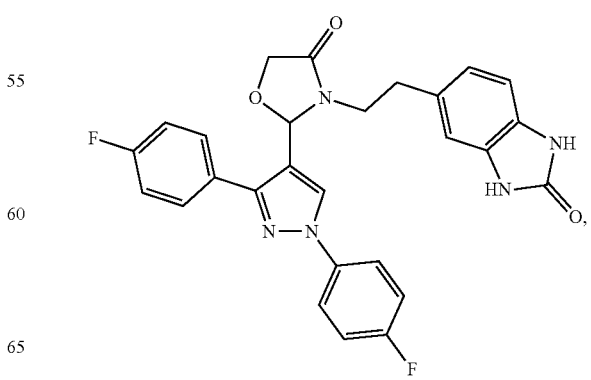

125
-continued
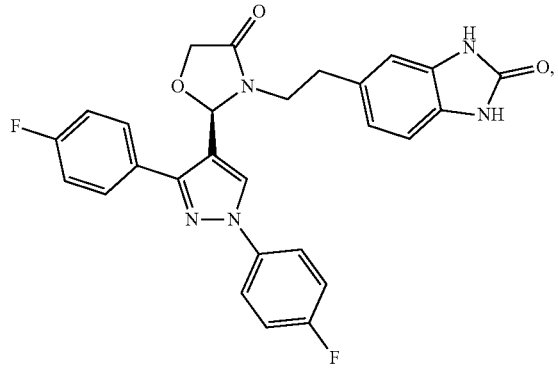
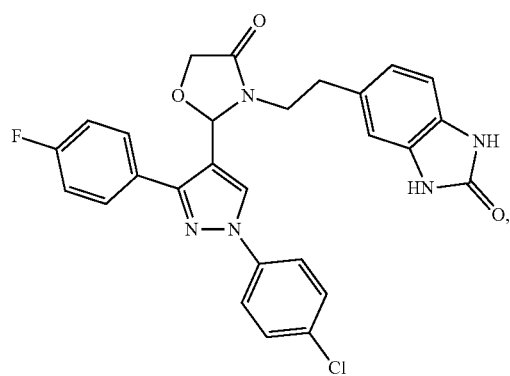
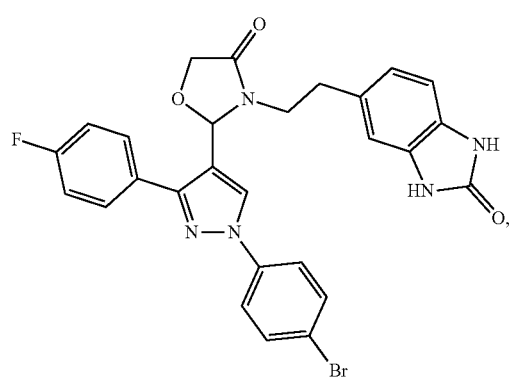
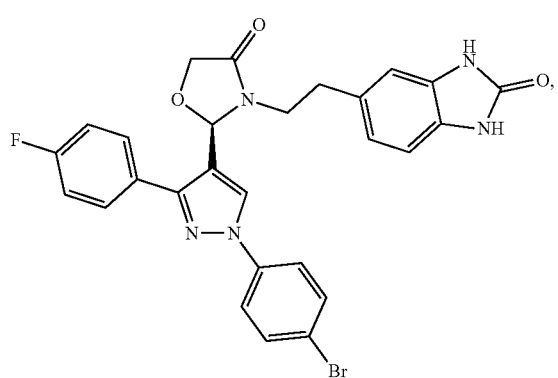
126
-continued
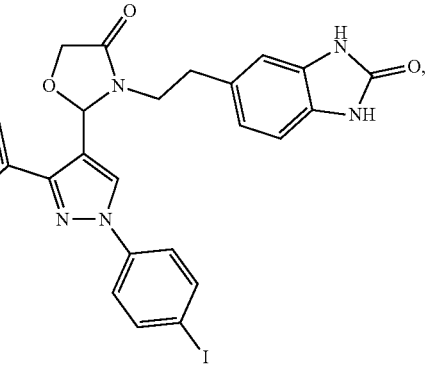
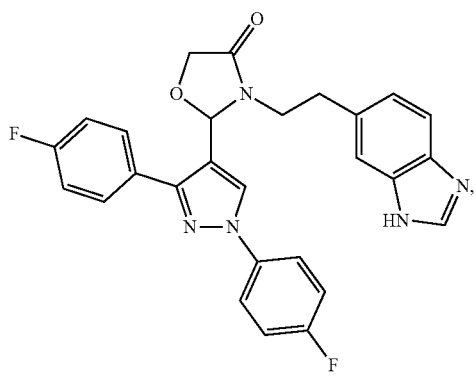
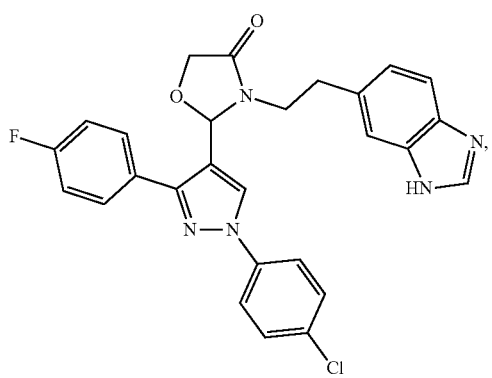
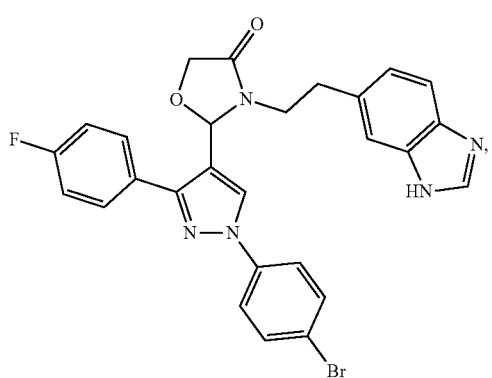

127
-continued

128
-continued

129
-continued
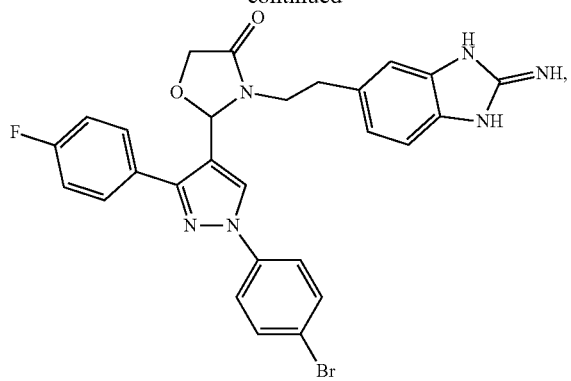
130
-continued
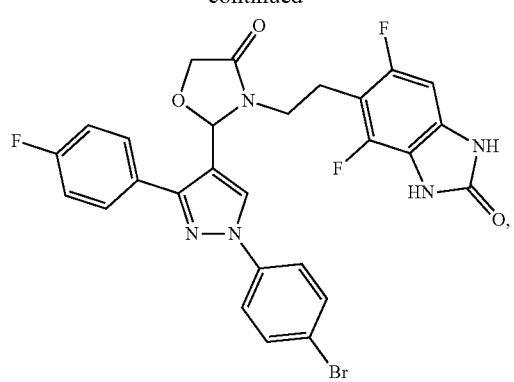
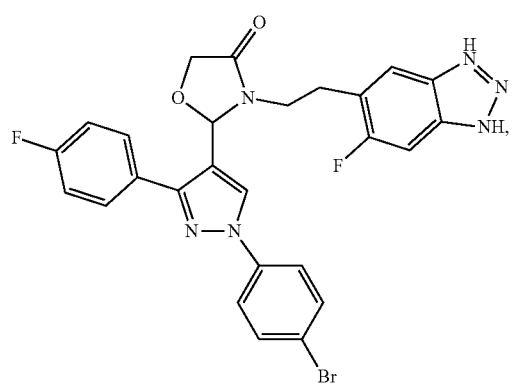
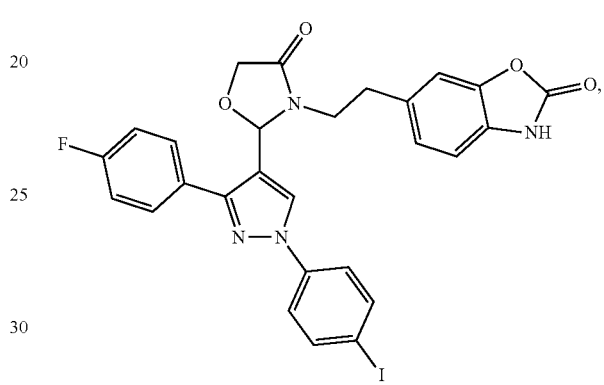
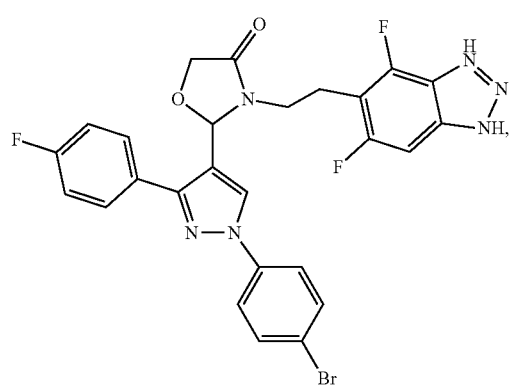
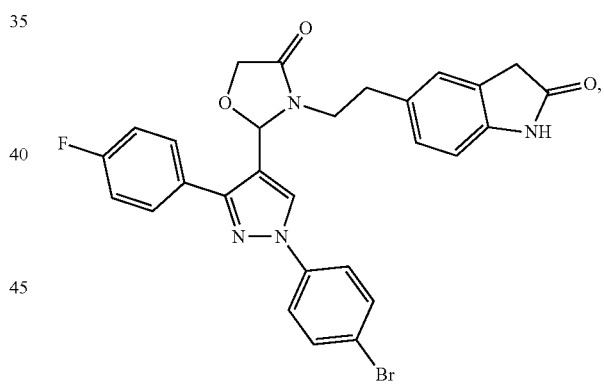
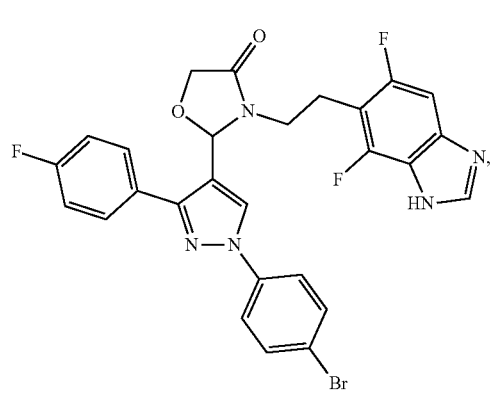
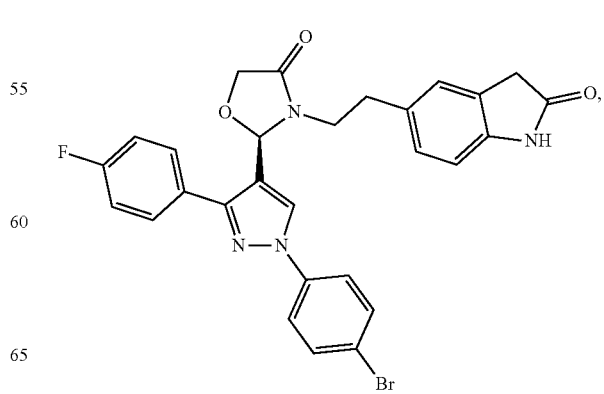

131
-continued
132
-continued

133
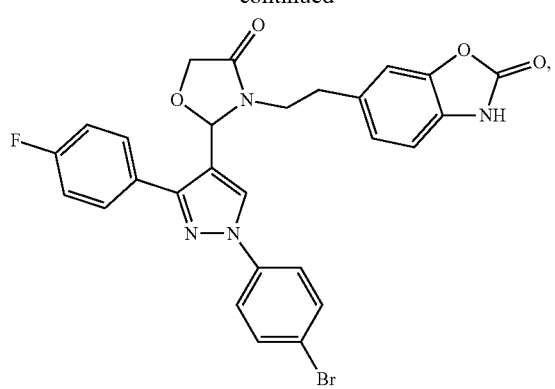
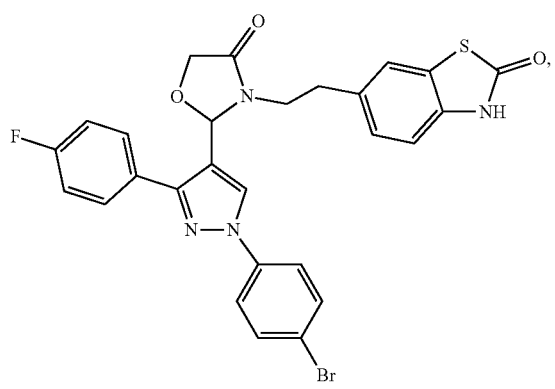
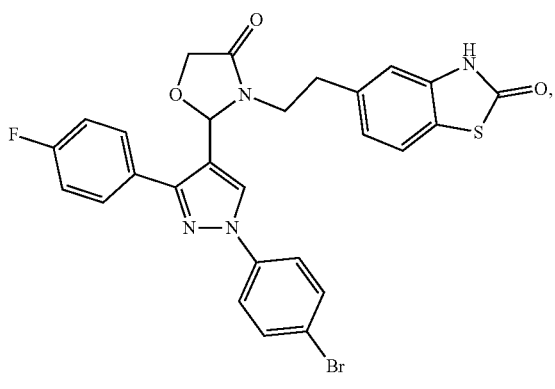
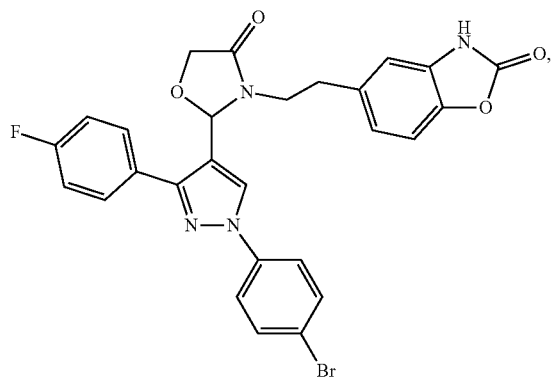
134
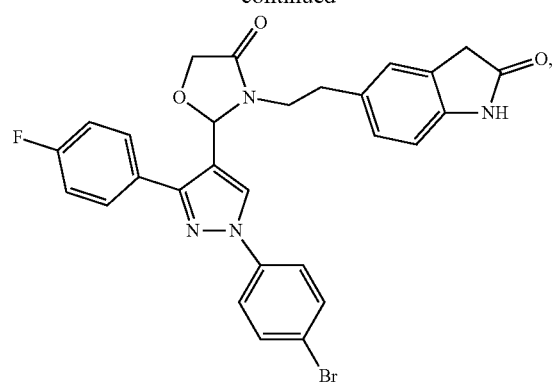
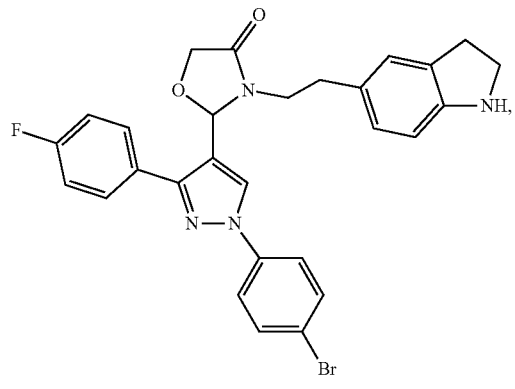
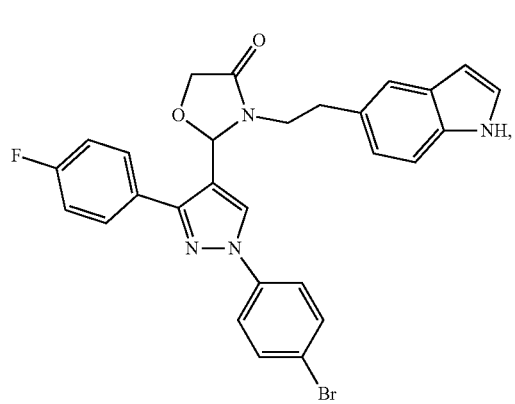
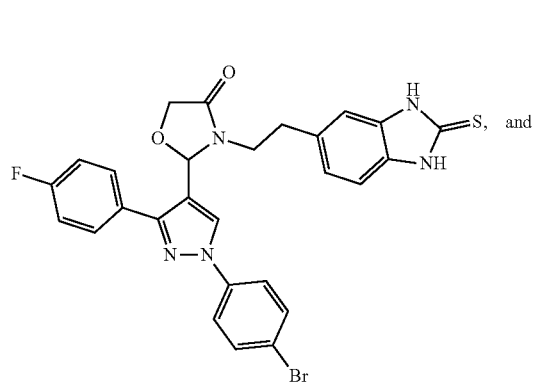

-continued

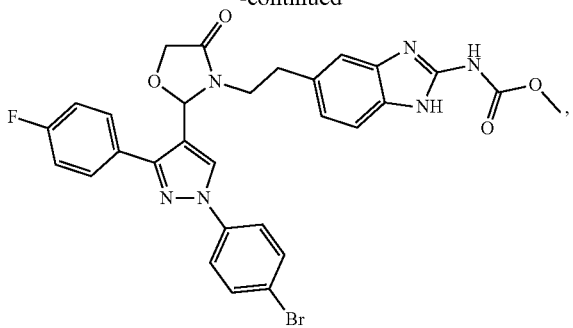

or a pharmaceutically acceptable salt or enantiomer or tautomer thereof.

7. The compound of claim 1, wherein Q is p-fluorophenyl.

8. A pharmaceutical composition comprising the compound of claim 1, and a pharmaceutically acceptable carrier.

9. A method for inhibiting hepatitis B virus in a subject in need thereof, comprising administering to the subject the pharmaceutical composition of claim 8.

10. The method of claim 9, wherein the subject is a mammal.

11. The compound of claim 1, wherein:
each of $R_1$, $R_2$ and $R_3$ is independently selected from hydrogen, halogen, optionally substituted alkyl, amino and hydroxyl;
$R_4$ and $R_5$, together with the carbon atoms to which they are attached, form an unsubstituted five-membered heterocyclic or heteroaryl group containing at least one nitrogen atom, wherein —$CH_2$— in said heterocyclic group is optionally replaced by —C(=O)—, —C(=S)—, or —C(=NH)—;
$R_6$ is selected from deuterium, halogen, amino and hydroxyl;
n is 0, 1 or 2; and
Q is aryl or heteroaryl, wherein the aryl or heteroaryl is optionally substituted with one or more halogens.

12. The compound of claim 1, wherein:
each of $R_1$, $R_2$ and $R_3$ is independently selected from hydrogen, halogen, optionally substituted alkyl, amino and hydroxyl;
$R_4$ and $R_5$, together with the carbon atoms to which they are attached, form an unsubstituted five-membered heterocyclic group containing at least one nitrogen atom, wherein —$CH_2$— in said heterocyclic group is optionally replaced by —C(=O)—, —C(=S)—, or —C(=NH)—;
$R_6$ is selected from deuterium, halogen, amino and hydroxyl;
n is 0, 1 or 2; and
Q is aryl or heteroaryl, wherein the aryl or heteroaryl is optionally substituted with one or more halogens.

13. The compound of claim 1, wherein

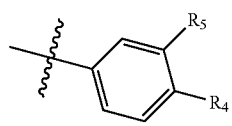

in formula I is selected from:

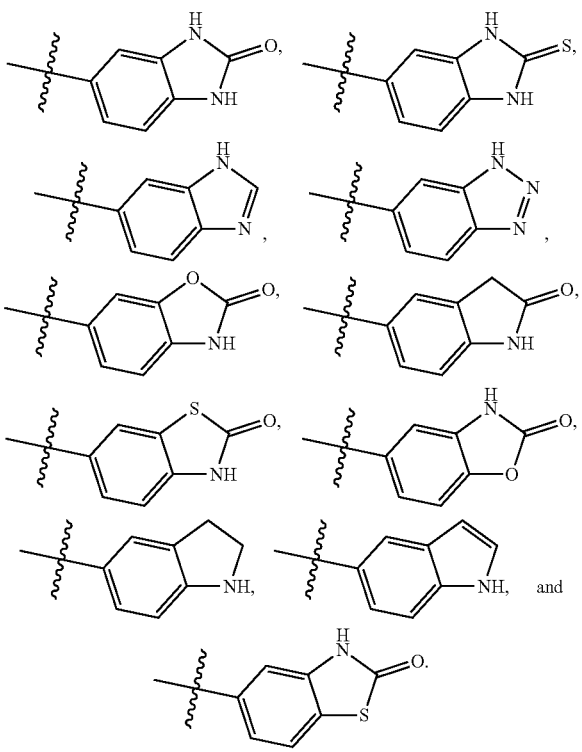

14. The compound of claim 1, wherein

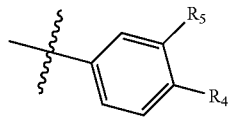

in formula I is selected from:

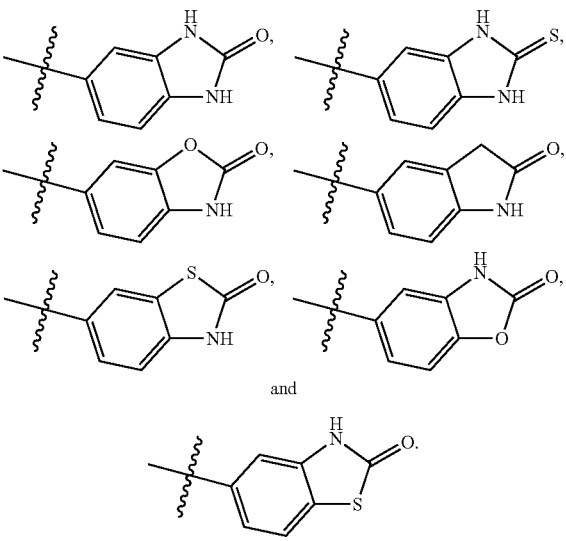

15. The compound of claim 1, wherein

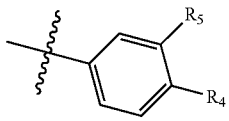

in formula I is selected from:

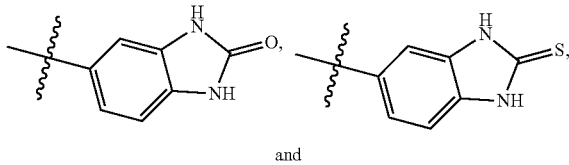

and

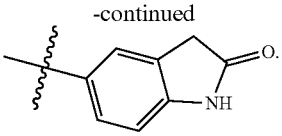

16. A method of treating hepatitis B virus in a subject in need thereof, comprising administering to the subject the pharmaceutical composition of claim 8.

17. A pharmaceutical composition comprising the compound of claim 6, and a pharmaceutically acceptable carrier.

18. A method for inhibiting hepatitis B virus in a subject in need thereof, comprising administering to the subject the pharmaceutical composition of claim 17.

19. The method of claim 18, wherein the subject is a mammal.

20. A method of treating hepatitis B virus in a subject in need thereof, comprising administering to the subject the pharmaceutical composition of claim 17.

* * * * *